US011351039B2

(12) United States Patent
Milella, Jr. et al.

(10) Patent No.: US 11,351,039 B2
(45) Date of Patent: Jun. 7, 2022

(54) BONE GRAFT DELIVERY SYSTEM AND METHOD FOR USING SAME

(71) Applicant: SPINAL SURGICAL STRATEGIES, LLC, Denver, CO (US)

(72) Inventors: Michael J. Milella, Jr., Escondido, CA (US); Jeffrey Kleiner, Denver, CO (US); Edward J. Grimberg, Jr., Golden, CO (US)

(73) Assignee: Spinal Surgical Strategies, Inc., Incline Village, NV (US)

( * ) Notice: Subject to any disclaimer, the term of this patent is extended or adjusted under 35 U.S.C. 154(b) by 0 days.

(21) Appl. No.: 17/419,883

(22) PCT Filed: Mar. 6, 2020

(86) PCT No.: PCT/US2020/021451
§ 371 (c)(1),
(2) Date: Jun. 30, 2021

(87) PCT Pub. No.: WO2020/181211
PCT Pub. Date: Sep. 10, 2020

(65) Prior Publication Data
US 2022/0039969 A1    Feb. 10, 2022

Related U.S. Application Data

(60) Provisional application No. 62/815,245, filed on Mar. 7, 2019.

(51) Int. Cl.
*A61F 2/46* (2006.01)
*A61F 2/44* (2006.01)

(52) U.S. Cl.
CPC ............ *A61F 2/4601* (2013.01); *A61F 2/447* (2013.01); *A61F 2/4611* (2013.01); *A61F 2/4684* (2013.01)

(58) Field of Classification Search
CPC ............... A61B 17/56; A61B 17/7095; A61B 17/320016; A61B 17/8811;
(Continued)

(56) References Cited

U.S. PATENT DOCUMENTS 5,842,786 A * 12/1998 Solomon ............. B01F 11/0054
366/139
6,309,372 B1 * 10/2001 Fischer ................ A61C 9/0026
433/90
(Continued)

FOREIGN PATENT DOCUMENTS

WO    2014/176526 A1    10/2014

OTHER PUBLICATIONS

Orthorebirth Co., Ltd. "Rebossis® A New Option in Bone Grafting", pp. 1-4, Kanagawa, Japan, accessed and printed on Jun. 29, 2021 from https://orthorebirthusa.com/content/ORB_REBOSSIS_BROCHURE_eng_web.pdf.
(Continued)

*Primary Examiner* — Jessica Weiss
(74) *Attorney, Agent, or Firm* — Corner Counsel, LLC

(57) ABSTRACT

The present invention relates to an apparatus, system and method for delivery of bone graft material in a patient's spine. The graft delivery device according to various embodiments delivers and disperses biologic material to a disc space and without withdrawal from the surgical site. In one embodiment, the graft delivery device includes a plunger with a distal end configured to bend relative to a longitudinal axis as bone graft material is delivery to the disc space. The plunger can include two arms that extend generally parallel to the longitudinal axis. The graft delivery device may selectively deliver a fusion cage for deposit to the same disc space.

7 Claims, 14 Drawing Sheets

(58) Field of Classification Search
CPC ............ A61B 17/8816; A61B 17/8822; A61B 17/8825; A61B 17/8833; A61F 2/28; A61F 2/4601; A61F 2/46; A61F 2/4611; A61F 2/4684; A61F 2/447; A61M 3/00; A61M 3/005
USPC ............................................ 606/86 R, 92–95
See application file for complete search history.

(56) References Cited

U.S. PATENT DOCUMENTS

| 7,025,771 | B2* | 4/2006 | Kuslich | A61B 17/8811 606/93 |
|---|---|---|---|---|
| 8,034,034 | B2* | 10/2011 | Hess | A61B 17/8833 604/226 |
| 10,080,671 | B2 | 9/2018 | Dewey et al. | |
| 2008/0208255 | A1 | 8/2008 | Siegal | |
| 2011/0071536 | A1* | 3/2011 | Kleiner | A61F 2/4601 606/94 |
| 2015/0148907 | A1* | 5/2015 | Kleiner | A61F 2/4611 623/17.16 |
| 2015/0320938 | A1* | 11/2015 | King | A61B 10/025 604/28 |
| 2016/0106551 | A1* | 4/2016 | Grimberg, Jr. | A61F 2/4601 623/17.16 |
| 2016/0296344 | A1* | 10/2016 | Greenhalgh | A61B 17/1659 |
| 2017/0238984 | A1* | 8/2017 | Kleiner | A61B 17/8816 |

OTHER PUBLICATIONS

Orthorebirth USA, "ReBOSSIS®: The Only Biosynthetic Scaffold with Electrospun Microfiber Construction", Nov. 28, 2017, pp. 1-2, Georgetown, Texas.

* cited by examiner

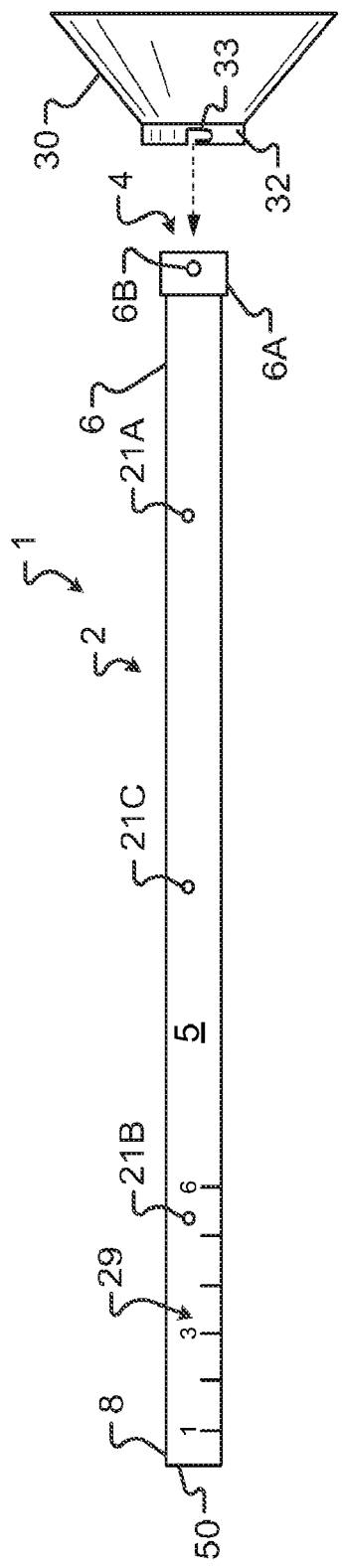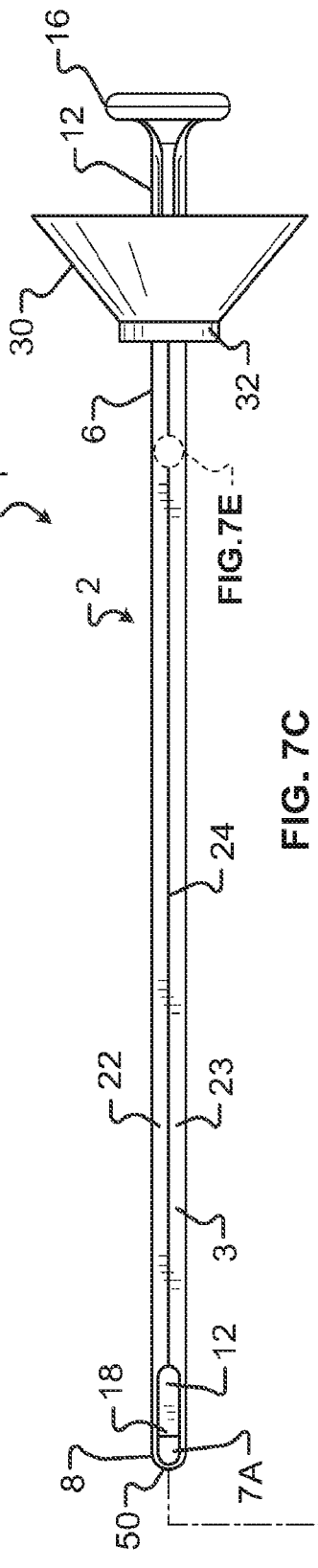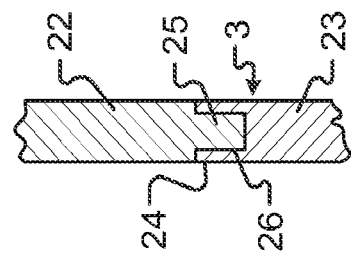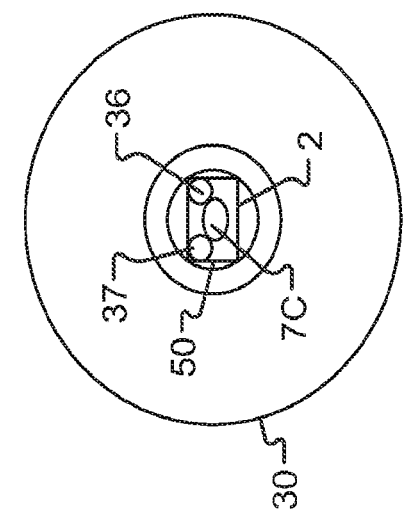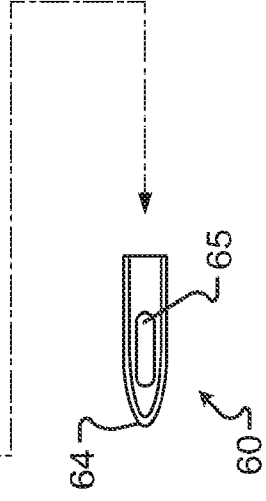

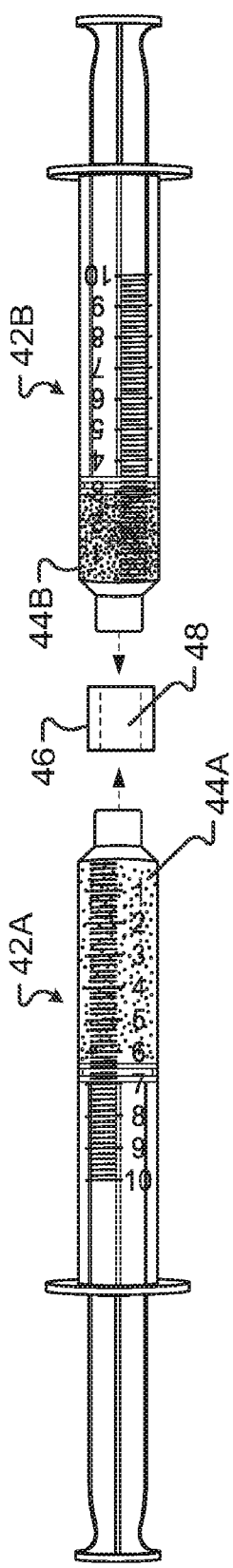
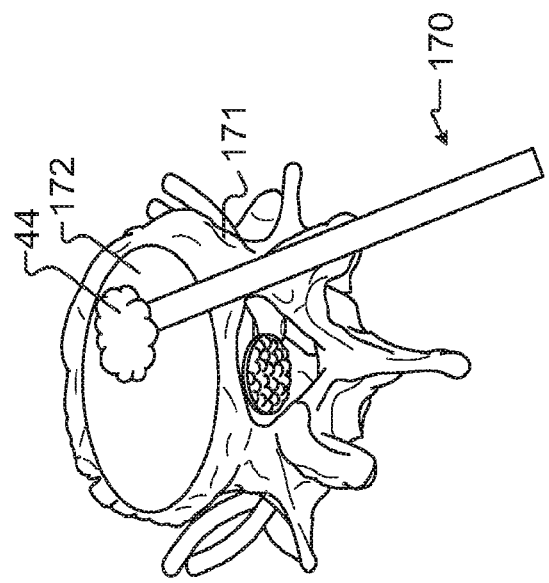
FIG. 7F
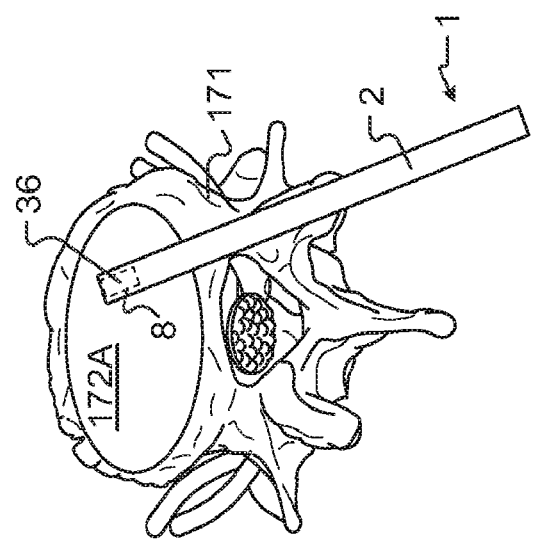
FIG. 8 (Prior Art)
FIG. 7G

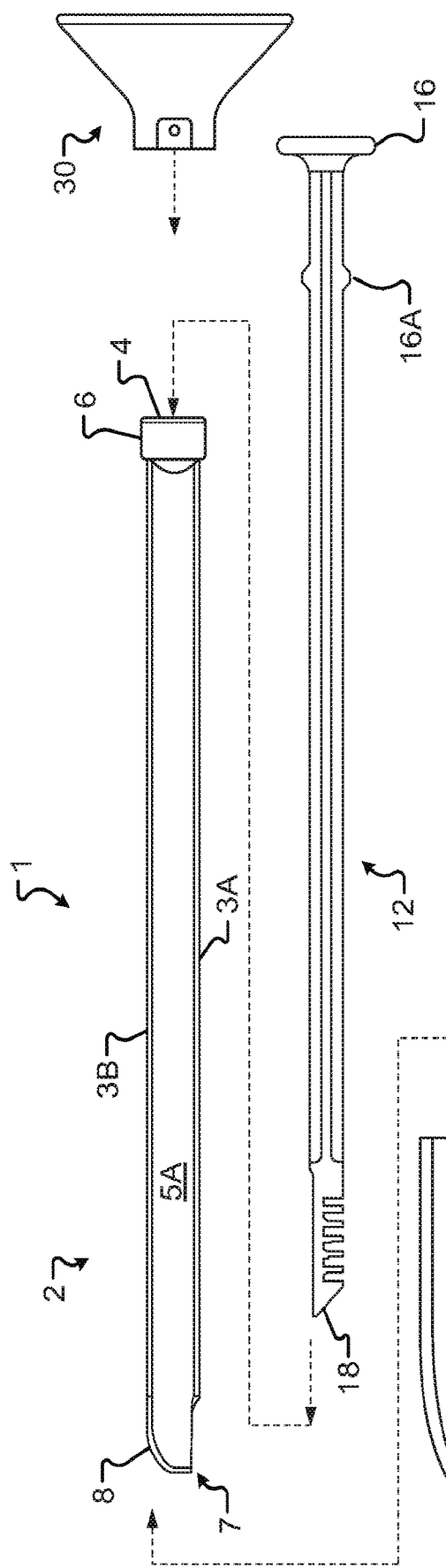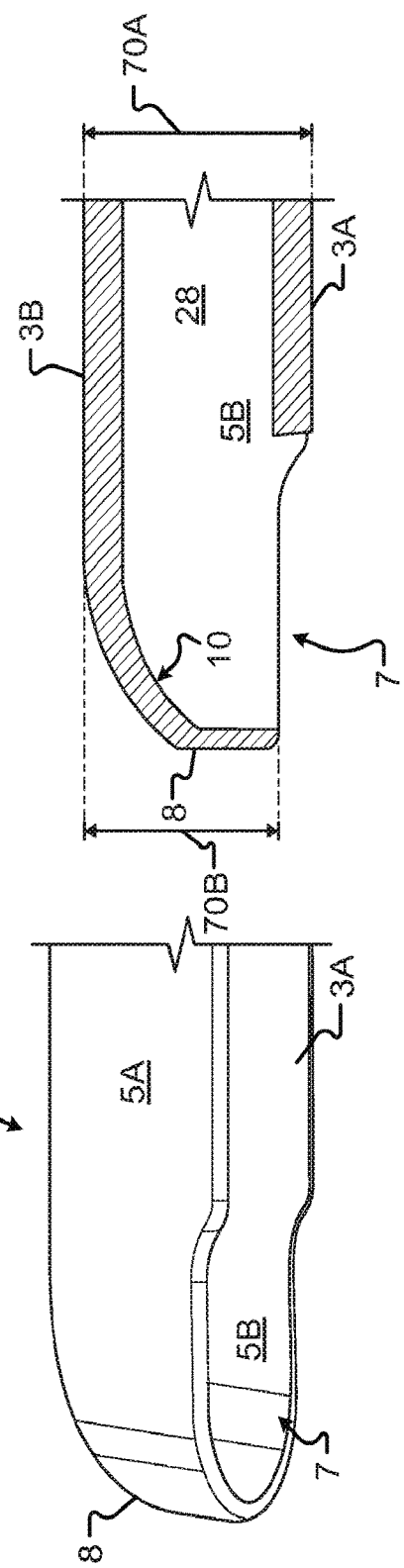
FIG. 10
FIG. 11
FIG. 12

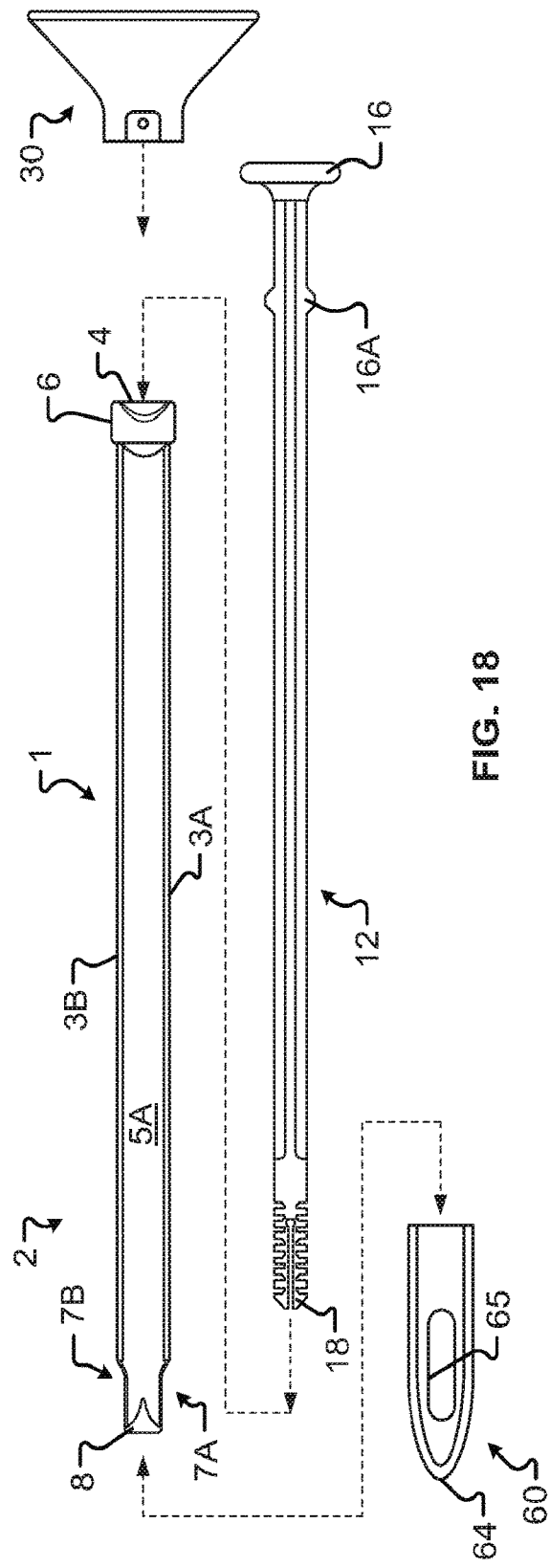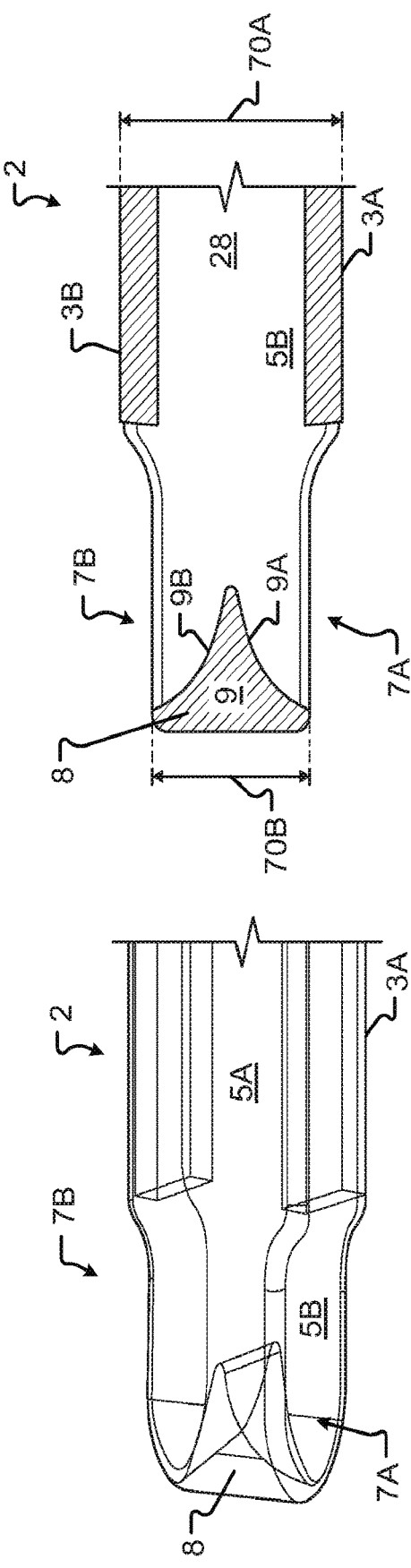
FIG. 18
FIG. 19
FIG. 20

BONE GRAFT DELIVERY SYSTEM AND METHOD FOR USING SAME

CROSS REFERENCE TO RELATED APPLICATIONS

This application claims the benefit of U.S. Provisional Application No. 62/815,245, filed on Mar. 7, 2019, the disclosure of which is incorporated herein by reference in its entirety.

FIELD OF THE INVENTION

This disclosure relates to orthopedic surgery, and more specifically to an apparatus and method for delivery of bone graft material into a patient, for example, during the placement of surgical cages or other medical implants in a patient's spine.

BACKGROUND OF THE INVENTION

According to the American Academy of Orthopedic Surgeons, about 250,000 spinal fusion surgeries are performed every year, mostly on adults between the ages of 45 to 64. Spinal fusion is a process by which two or more of the vertebrae that make up the spinal column are fused together with bone grafts and internal devices (such as rods) that heal into a single solid bone. Spinal fusion can eliminate unnatural motion between the vertebrae and, in turn, reduce pressure on nerve endings. In addition, spinal fusion can be used to treat, for example, injuries to spinal vertebrae caused by trauma; protrusion and degeneration of the cushioning disc between vertebrae (sometimes called slipped disc or herniated disc); abnormal curvatures (such as scoliosis or kyphosis); and weak or unstable spine caused by infections or tumors.

Individuals who suffer from degenerative disc disease, natural spine deformations, a herniated disc, spine injuries or other spine disorders may require surgery on the affected region to relieve the individual from pain and prevent further injury to the spine and nerves. Spinal surgery may involve removal of damaged joint tissue, insertion of a tissue implant and/or fixation of two or more adjacent vertebral bodies. In some instances, a medical implant is also inserted, such as a fusion cage. The surgical procedure will vary depending on the nature and extent of the injury. Generally, there are five main types of lumbar fusion, including: posterior lumbar fusion ("PLF"), posterior lumbar interbody fusion ("PLIF"), anterior lumbar interbody fusion ("ALIF"), circumferential 360 fusion, and transforaminal lumbar interbody fusion ("TLIF"). More recently, direct lateral interbody fusion ("D-LIF") has become available. A posterior approach is one that accesses the surgical site from the patient's back, an anterior approach is one that accesses the surgical site from the patient's front or chest, and a direct lateral approach is one that accesses the surgical site from the patient's side. There are similar approaches for fusion in the interbody or cervical spine regions. For a general background on some of these procedures and the tools and apparatus used in certain procedures, see U.S. Prov. Pat. Appl. No. 61/120,260 filed on Dec. 5, 2008, the entire disclosure of which is incorporated by reference in its entirety. In addition, further background on procedures and tools and apparatus used in spinal procedures is found in U.S. patent application Ser. No. 12/632,720 filed on Dec. 7, 2009, now U.S. Pat. No. 8,366,748, the entire disclosure of which is incorporated by reference in its entirety.

Vertebrectomy, or the removal or excision of a vertebra, is another type of spinal surgery that may be necessary to alleviate pain and/or correct spinal defects, such as when disc material above and below a particular vertebra protrudes from the spine and contacts the spinal cord. Once the problematic vertebra is removed, a specialized fusion cage (also called a vertebrectomy cage) may be inserted into its place to restore structural continuity to the spine.

Some disadvantages of traditional methods of spinal surgery include, for example, the pain associated with the procedure, the length of the procedure, the complexity of implements used to carry out the procedure, the prolonged hospitalization required to manage pain, the risk of infection due to the invasive nature of the procedure, and the possible requirement of a second procedure to harvest autograft bone from the iliac crest or other suitable site on the patient for generating the required quantity of cancellous and/or cortical bone.

A variety of semisolid bone graft materials are available on the market which ostensibly increase spinal fusion rates without the morbidity of autograft bone harvesting. Each of the manufacturers espouses their product as the most advantageous for healing. Many of these products have similar handling characteristics and the literature reveals that they have similar healing prospects. They come in a syringe and it is up to the surgeon to apply the selected material to the target site. The most common site for application is to the disc space after it has been prepared to a bleeding bed and ready to accept a cage and/or the grafting material. This represents a long and narrow channel even in open procedures. The surgeon is left to his or her own devices as to how to get the graft from its container to the active site. The devices which have been used have included a "caulking gun" construct and a variety of barrel shaft with a plunger design.

Bone graft typically includes crushed bone (cancellous bone, cortical bone, or a combination of these (and/or other natural materials)), and may further comprise synthetic biocompatible materials. Bone graft of this type is intended to stimulate growth of healthy bone. Another type of bone graft has a fibrous composition similar in consistency and appearance to a cotton ball. Fibrous bone graft includes interconnected macro- and microporous structures that foster development of new bone and nurture the growth of capillary blood vessels. Although fibrous bone graft provides certain benefits, it can be difficult to deliver to a surgical site due to it compressibility and because its fibers can catch or snag on delivery tools. One example of the fibrous bone graft comprises beta tricalcium phosphate, calcium carbonate and a resorbable scaffold of Poly-L-lactide that form a biodegradable structure. One type of fibrous bone graft is marketed as ReBOSSIS® which is produced by ORTHOReBIRTH Co. Ltd.

As used herein, "bone graft" shall mean materials made up entirely of natural materials, entirely of synthetic biocompatible materials, or any combination of these materials. Bone graft often is provided by the supplier in a gel or slurry form, as opposed to a dry or granule form. Many companies provide various forms of bone graft in varying degrees of liquidity and viscosity, which may cause problems in certain prior art delivery devices using prepackaged bone graft, or where the bone graft is packaged by the surgeon. In addition, the method of delivery of bone graft to a particular location varies depending on the form of the bone graft utilized.

Autogenous bone (bone from the patient) or allograft bone (bone from another human being) are the most commonly used materials to induce bone formation. Generally, small pieces of bone are placed into the space between the vertebrae to be fused. Sometimes larger solid pieces of bone are used to provide immediate structural support. Autogenous bone is generally considered superior at promoting fusion. However, this procedure requires an additional, separate surgery to remove bone from another area of the patient's body such as the pelvis or fibula. Thus, it has been reported that about 30 percent of patients have significant pain and tenderness at the graft harvest site, which may be prolonged, and in some cases outlast the back pain the procedure intended to correct. Similarly, allograft bone and other bone graft substitutes, although eliminating the need for a second surgery, have drawbacks in that they have yet to be proven as cost effective and efficacious substitutes for autogenous bone fusion.

An alternative to autogenous or allograft bone is the use of growth factors that promote bone formation. For example, studies have shown that the use of bone morphogenic proteins ("BMPs") results in better overall fusion, less time in the operating room and, more importantly, fewer complications for patients because it eliminates the need for the second surgery. However, use of BMPs, although efficacious in promoting bone growth, can be prohibitively expensive.

Another alternative is the use of a genetically engineered version of a naturally occurring bone growth factor. This approach also has limitations. Specifically, surgeons have expressed concerns that genetically engineered BMPs can dramatically speed the growth of cancerous cells or cause non-cancerous cells to become more sinister. Another concern is unwanted bone creation. There is a chance that bone generated by genetically engineered BMPs could form over the delicate nerve endings in the spine or, worse, somewhere else in the body.

Regenerative medicine, which harnesses the ability of regenerative cells, e.g., stem cells (i.e., the unspecialized master cells of the body) to renew themselves indefinitely and develop into mature specialized cells, may be a means of circumventing the limitations of the prior-art techniques. Stem cells, i.e., both embryonic and adult stem cells, have been shown to possess the nascent capacity to become many, if not all, of the 200+ cell and tissue types of the body, including bone. Recently, adipose tissue has been shown to be a source of adult stem cells (See e.g. Zuk, Patricia Z. et al., "Multilineage Cells from Human Adipose Tissue: Implication for Cell-Based Therapies," Tissue Engineering, April 2001, 7:211-28; Zuk, Patricia A. et al., "Human Adipose Tissue Is A Source Of Multipotent Stem Cells," Molecular Biology of the Cell, 2002, 13:4279-4295). Adipose tissue (unlike marrow, skin, muscle, liver and brain) is comparably easy to harvest in relatively large amounts with low morbidity (See e.g. Commons, G. W., Halperin, B., and Chang, C. C. (2001) "Large-volume liposuction: a review of 631 consecutive cases over 12 years" Plast. Reconstr. Surg. 108, 1753-63; Katz, B. E., Bruck, M. C. and Coleman, W. P. 3 (2001b) "The benefits of powered liposuction versus traditional liposuction: a paired comparison analysis" Dermatol. Surg. 27, 863-7). Accordingly, given the limitations of the prior art spinal fusion techniques, there exists a need for a device that incorporates regenerative cells, e.g., stem cells that possess the ability to induce bone formation.

Many different methods and approaches have been attempted to induce bone formation or to promote spinal fusion. The traditional devices for inserting bone graft impair the surgeon's visualization of the operative site, which can lead to imprecise insertion of bone graft and possible harm to the patient. The caulking gun and the collection of large barrel/plunger designs typically present components at the top of their structure which block the view of the surgical site. The surgeon must then resort to applying pressure to the surgical site to approximate the location of the device's delivery area. Such rough maneuvering can result in imprecise placement of bone graft, and in some cases, rupture of the surgical area by penetrating the annulus and entering the abdominal cavity. Also, in some surgical procedures, the devices for inserting bone graft material are applied within a cannula inserted or placed in the surgical area, further limiting the size and/or profile of the bone graft insertion device. When a cannula is involved, some traditional devices such as the large barrel/plunger designs and/or some caulking gun designs simply cannot be used as they cannot be inserted within the cannula.

Traditional devices for inserting bone graft deliver the bone graft material at the bottom of the delivery device along the device's longitudinal axis. Such a delivery method causes the bone grafting material to become impacted at the bottom of the delivery device which jams the device and promotes risk of rupture of the surgical area by penetrating the annulus and entering the abdominal cavity. Further, traditional devices that deliver bone graft material along their longitudinal axis may cause rupture of the surgical area or harm to the patient because of the ensuing pressure imparted by the ejected bone graft material from the longitudinal axis of the device. Furthermore, the graft material is distributed only in the longitudinal axis and does not fill in the peripheral areas of the disk.

As mentioned, the method of delivery of bone graft to a particular location varies depending on the form of the bone graft utilized. For example, in the case of slurry type bone graft, various dispensing devices have been developed having applicators designed to accommodate this type of bone graft. One such device is disclosed by U.S. Pat. No. 5,925,051 issued to Mikhail on Jul. 20, 1999 ("Mikhail"), the disclosure of which is incorporated herein by reference in its entirety. Mikhail provides a caulking gun type dispenser for introducing bone graft in an enlarged bone (e.g. femoral) cavity. The device preferably includes a barrel pre-loaded with bone graft and a cannulated ejector positioned over a multi-section guide wire. This arrangement purports to accomplish both ejecting bone graft from the barrel and compacting the bone graft material while being guided on the guide wire. Mikhail, however, is designed solely for use with slurry-type bone graft, and does not accommodate bone graft in granule form, which often varies in size among granules and does not have the same "flow" or viscosity characteristics as slurry-type bone graft. Thus, the applicator of Mikhail is insufficient for introducing most bone graft to a surgical site in a patient.

U.S. Pat. No. 6,019,765 issued to Thornhill et al. on Feb. 1, 2000 ("Thornhill") also teaches a bone graft delivery device and is incorporated herein by reference in its entirety. The bone graft device applicator of Thornhill is used to apply bone graft to an artificial joint without having to remove a previously implanted prosthesis component. The applicator device includes a hollow tube with an actuation mechanism for discharging the bone graft from the device via a nozzle coupled to a distal end of the tube. The bone graft delivery device of Thornhill may include various components for loading the device with the bone graft, and may further include a plurality of nozzles each having a geometry suited for a particular application. Like Mikhail, the Thornhill delivery device is designed for use with bone slurry, and requires much custom instrumentation and different sized parts to achieve success in many bone graft delivery applications, which in turn increases the time to assemble and use the delivery device and may create further problems during the surgical operation.

U.S. Pat. No. 5,697,932 issued to Smith et al. on Dec. 16, 1997 ("Smith") discloses yet another bone graft delivery system and method and is incorporated herein by reference in its entirety. In Smith, a hollow tube of pre-loaded bone graft and a plunger are used to facilitate delivery of the bone graft to a bone graft receiving area. A positioning structure is provided on the plunger to maintain the plunger in a desirable position with respect to the hollow tube. Adjunct positioning means may also be provided to ensure that the plunger remains in the desirable position during the packing of bone graft into the bone graft receiving area. Like the devices of Thornhill and Mikhail, the device disclosed by Smith is clearly designed solely for slurry type bone graft, and does not provide an effective opening for receiving the desired amount of bone graft. Furthermore, the hollow tube shown by Smith is narrow and does not have a footing or other apparatus associated with the delivery device for preventing the device from penetrating, for example, the abdominal region of a patient, which may occur during tamping or packing of the bone graft. This in turn may cause serious injury to a patient if not controlled, and for these reasons the device of Smith is also insufficient for delivery of bone graft to a surgical site.

Traditional devices for inserting a fusion cage or other medical implants into a patient's spine or other surgical area are distinct and separate from traditional devices that deliver bone graft material to the surgical site. For example, once an implant has been positioned, then bone growth material is packed into the internal cavity of the fusion cage. Also, sometimes the process is reversed, i.e., the bone growth is inserted first, and then the implant. These bone growth inducing substances come into immediate contact with the bone from the vertebral bone structures which project into the internal cavity through the apertures. Two devices are thus traditionally used to insert bone graft material into a patient's spine and to position and insert a fusion cage. These devices thus necessitate a disc space preparation followed by introduction of the biologic materials necessary to induce fusion and, in a separate step, application of a structural interbody fusion cage.

The problems associated with separate administration of the biologic material bone graft material and the insertion of a fusion cage include applying the graft material in the path of the cage, restricting and limiting the biologic material dispersed within the disc space, and requiring that the fusion cage be pushed back into the same place that the fusion material delivery device was, which can lead to additional trauma to the delicate nerve structures.

Fusion cages provide a space for inserting a bone graft between adjacent portions of bone. Such cages are often made of titanium and are hollow, threaded, and porous in order to allow a bone graft contained within the interior of the cage of grow through the cage into adjacent vertebral bodies. Such cages are used to treat a variety of spinal disorders, including degenerative disc diseases such as Grade I or II spondylolistheses of the lumbar spine.

Surgically implantable intervertebral fusion cages are well known in the art and have been actively used to perform spinal fusion procedures for many years. Their use became popularized during the mid-1990's with the introduction of the BAK Device from the Zimmer Inc., a specific intervertebral fusion cage that has been implanted worldwide more than any other intervertebral fusion cage system. The BAK system is a fenestrated, threaded, cylindrical, titanium alloy device that is capable of being implanted into a patient as described above through an anterior or posterior approach, and is indicated for cervical and lumbar spinal surgery. The BAK system typifies a spinal fusion cage in that it is a highly fenestrated, hollow structure that will fit between two vertebrae at the location of the intervertebral disc.

Spinal cages are generally inserted through a traditional open operation, though laparoscopic or percutaneous insertion techniques may also be used. Cages may also be placed through a posterior lumbar interbody fusion, or PLIF, technique, involving placement of the cage through a midline incision in the patient's back, or through a direct lateral interbody fusion, or D-LIF, technique, involving placement of the cage through an incision in the patient's side.

A typical procedure for inserting a known/traditional threaded or impacted fusion cage is as follows. First, the disc space between two vertebrae of the lumbar spine is opened using a wedge or other device on a first side of the vertebrae. The disc space is then prepared to receive a fusion cage. Conventionally, a threaded cage is inserted into the bore and the wedge is removed. A disc space at the first side of the vertebrae is then prepared, and a second threaded fusion cage inserted into the bore. Alternatively, the disc space between adjacent vertebrae may simply be cleared and a cage inserted therein. Sometimes only one cage is inserted obliquely into the disc space. Use of a threaded cage may be foregone in favor of a rectangular or pellet-shaped cage that is simply inserted into the disc space. Lastly, bone graft material may be inserted into the surgical area using separate tools and devices.

U.S. Pat. No. 4,743,256 issued to Brantigan ("Brantigan") discloses a traditional spinal surgical method involving the implantation of a spinal fusion cage. The cage surfaces are shaped to fit within prepared endplates of the vertebrae to integrate the implant with the vertebrae and to provide a permanent load-bearing strut for maintaining the disc space. Brantigan teaches that these cages typically consist of a homogeneous nonresorbable material such as carbon-reinforced polymers such as polyether ether ketone (PEEK) or polyether ketone ether ketone ("PEKEKK"). Although these cages have demonstrated an ability to facilitate fusion, a sufficient fusion is sometimes not achieved between the bone chips housed within the cage and the vertebral endplates. In particular, achieving a complete fusion in the middle portion of the cage has been particularly problematic. In any case, Brantigan teaches the separate process and procedure for the insertion of a fusion cage and the insertion of bone graft. Indeed, local bone graft harvested from the channel cuts into the vertebrae to receive the plug supplements the fusion.

U.S. Pat. Appl. Pub. 2007/0043442 of Abernathie et al. ("Abernathie") discloses another traditional spinal surgical method involving the implantation of a spinal fusion cage. Abernathie relates generally to an implantable device for promoting the fusion of adjacent bony structures, and a method of using the same. More specifically, Abernathie relates to an expandable fusion cage that may be inserted into an intervertebral space, and a method of using the same. Abernathie includes an aperture in the fusion cage to allow bone growth therethrough, as a separate procedure to the insertion of the fusion cage.

Traditional fusion cages are available in a variety of designs and composed of a variety of materials. The cages or plugs are commonly made of an inert metal substrate such as stainless steel, cobalt-chromium-molybdenum alloys, titanium or the like having a porous coating of metal particles of similar substrate metal, preferably titanium or the like as disclosed, for example, in the Robert M. Pilliar U.S. Pat. No. 3,855,638 issued Dec. 24, 1974 and U.S. Pat. No. 4,206,516 issued Jun. 10, 1980. These plugs may take the form of flat sided cubical or rectangular slabs, cylindrical rods, cruciform blocks, and the like.

U.S. Pat. No. 5,906,616 issued to Pavlov et al. ("Pavlov") discloses a fusion cage of various cylindrical and conical shapes and a method of insertion. Like Brantigan, Pavlov teaches the separate process and procedure for the insertion of a fusion cage and the insertion of bone graft. U.S. Pat. No. 5,702,449 ("McKay") discloses a spinal implant comprising a cage made of a porous biocompatible material reinforced by an outer sleeve made of a second material which is relatively stronger under the compressive load of the spine than the biocompatible material. U.S. Pat. No. 6,569,201 issued to Moumene et al. ("Moumene") teaches a bone fusion device having a structural bioresorbable layer disposed upon the outer surface of a non-resorbable support. As the bioresorbable structural layer resorbs over time, the load upon the bone graft housed within the non-resorbable support increases. Published PCT Application No. WO 99/08627 ("Gresser") discloses a fully bioresorbable interbody fusion device, as well as homogeneous composite devices containing at least 25% resorbable materials. U.S. Pat. No. 7,867,277 issued to Tohmeh discloses a spinal fusion implant of bullet shaped end.

U.S. Pat. No. 7,846,210 issued to Perez-Cruet et al. ("Perez-Cruet") discloses an interbody device assembly consisting of a fusion device and an insertion device. The insertion device positions the fusion device between two vertebrae, provides bone graft material, and then detaches from the fusion device, leaving the fusion device in place to restore disc space height. However, the Perez-Cruet device is designed to receive bone graft material from its insertion device and distribute the material away from the fusion device. In most embodiments of the fusion device, a center plate is positioned immediately downstream of the received bone graft material and directs the bone graft to opposing sides of the fusion device. (See, for example, FIG. 20 depicting plate 308 directing bone graft material 392 along the exterior sides of the fusion device 302). As such, the Perez-Cruet fusion device is unlikely to completely fill the areas near of its fusion cage and deliver bone graft material to the surrounding bone graft site. Furthermore, none of the Perez-Cruet fusion device embodiments feature a defined interior space or a cage-style design. Indeed, the Perez-Cruet fusion device explicitly teaches away from a contained-interior, fusion-cage-style device, asserting that its fusion device fills all of the disc space as opposed to a cage design, which contains the bone material. Furthermore, the Perez-Cruet does not feature a distal tip that functions to precisely position the fusion device and stabilize the device during delivery of bone graft material.

U.S. Pat. No. 7,985,256 issued to Grotz et al. ("Grotz") discloses an expandable spinal implant for insertion between opposed vertebral end plates. The implant is a cylinder block of slave cylinders; a central cavity between the cylinders receives bone graft material and pistons positioned within the cylinders provide a corrective bone engaging surface for expanding against a first vertebral end plate. The insertion tool used to place the spinal implant includes a handle and hollow interior for housing hydraulic control lines and a bone graft supply line. The Grotz system does not allow precise positioning or delivery of bone graft material without an implant and requires a complex and bulky insertion tool.

U.S. Pat. Appl. Pub. 2010/0198140 to Lawson ("Lawson") discloses a tool comprising a cannula with an open slot at the distal end and a closed tip. Lawson's tool employs tamps to push bone aside and open up a void for filling; solid bone pellets are then rammed down the hollow interior of the cannula by a tamper and delivered to the surgical site. Lawson does not allow precise positioning or delivery of viscous bone graft material and has no capability to interconnect or integrate with an implant such as a bone graft fusion cage.

U.S. Pat. Appl. Pub. 2010/0262245 to Alfaro et al. ("Alfaro") discloses a delivery system for an intervertebral spacer and a bone grafting material comprising a spacer disengagingly attached to a hollow handle. The handle comprises a chamber and bone grafting material-advancing means for introducing bone grafting material from the chamber into the spacer and the intervertebral spaces. The Alfaro system does not allow precise positioning or delivery of bone graft material through a distal tip that precisely positions the fusion device and stabilizes the device during delivery of bone graft material, and does not allow primarily lateral injection of bone graft fusion material.

By way of providing additional background and context, and while known to those skilled in the art, the following references are nonetheless identified to help explain the nature of the surgical procedures in which bone graft is used and to further describe the various tools and other apparatus commonly associated therewith: U.S. Pat. No. 6,309,395 to Smith et al.; U.S. Pat. No. 6,142,998 to Smith et al.; U.S. Pat. No. 7,014,640 to Kemppanien et al.; U.S. Pat. No. 7,406,775 to Funk, et al.; U.S. Pat. No. 7,387,643 to Michelson; U.S. Pat. No. 7,341,590 to Ferree; U.S. Pat. No. 7,288,093 to Michelson; U.S. Pat. No. 7,207,992 to Ritland; U.S. Pat. No. 7,077,864 Byrd III, et al.; U.S. Pat. No. 7,025,769 to Ferree; U.S. Pat. No. 6,719,795 to Cornwall, et al.; U.S. Pat. No. 6,364,880 to Michelson; U.S. Pat. No. 6,328,738 to Suddaby; U.S. Pat. No. 6,290,724 to Marino; U.S. Pat. No. 6,113,602 to Sand; U.S. Pat. No. 6,030,401 to Marino; U.S. Pat. No. 5,865,846 to Bryan, et al.; U.S. Pat. No. 5,569,246 to Ojima, et al.; U.S. Pat. No. 5,527,312 to Ray; and U.S. Pat. Appl. Pub. No. 2008/0255564 to Michelson.

By way of providing additional background and context, and while known to those skilled in the art, the following references are nonetheless identified to help explain the nature of the surgical procedures in which fusion cages are used and to further describe the various tools and other apparatus commonly associated therewith: U.S. Pat. No. 6,569,201 to Moumene et al.; U.S. Pat. No. 6,159,211 to Boriani et al.; U.S. Pat. No. 4,743,256 to Brantigan; U.S. Pat. Appl. 2007/0043442 to Abernathie et al.; U.S. Pat. Nos. 3,855,638 and 4,206,516 to Pilliar; U.S. Pat. No. 5,906,616 issued to Pavlov et al.; U.S. Pat. No. 5,702,449 to McKay; U.S. Pat. No. 6,569,201 to Moumene et al.; PCT Appl. No. WO 99/08627 to Gresser; U.S. Pat. Appl. Pub. 2012/0022651 to Akyuz et al.; U.S. Pat. Appl. Pub. 2011/0015748 to Molz et al.; U.S. Pat. Appl. Pub. 2010/0249934 to Melkent; U.S. Pat. Appl. Pub. 2009/0187194 to Hamada; U.S. Pat. No. 7,867,277 issued to Tohmeh; U.S. Pat. No. 7,846,210 to Perez-Cruet et al.; U.S. Pat. No. 7,985,256 issued to Grotz et al.; U.S. Pat. Appl. Pub. 2010/0198140 to Lawson; and U.S. Pat. Appl. Pub. 2010/0262245 to Alfaro et al.

By way of providing additional background and context, and while known to those skilled in the art, the following references are nonetheless identified to help explain the nature of spinal fusion and devices and methods commonly associated therewith: U.S. Pat. No. 7,595,043 issued to Hedrick et al.; U.S. Pat. No. 6,890,728 to Dolecek et al.; U.S. Pat. No. 7,364,657 to Mandrusov, and U.S. Pat. No. 8,088,163 to Kleiner.

In addition, by way of providing additional background and context, the and while known to those skilled in the art, the following references are nonetheless identified to help explain the nature of spinal fusion and devices and methods commonly associated therewith: U.S. Pat. No. D647,202 entitled "Bone Marrow Harvesting Device" to Scifert issued Oct. 18, 2011; U.S. Pat. No. 7,897,164 entitled "Compositions and Methods for Nucleus Pulposus Regeneration" to Seifert issued Mar. 1, 2011; U.S. Pat. Appl. Pub. No. 2010/0112029 entitled "Compositions and Methods for Nucleus Pulposus Regeneration" to Scifert issued May 6, 2010; U.S. Pat. Appl. Pub. No. 2010/0021518 entitled "Foam Carrier for Bone Grafting" to Scifert issued Jan. 28, 2010; U.S. Pat. No. 7,824,703 entitled "Medical Implants with Reservoir(s), and Materials Preparable From Same" to Scifert, et al., issued Nov. 2, 2010; U.S. Pat. Appl. Pub. No. 2006/0247791 entitled "Multi-Purpose Medical Implant Devices" to McKay, et al., issued Nov. 2, 2006; U.S. Pat. Appl. Pub. No. 2007/0225811 entitled "Conformable Orthopedic Implant" to Scifert, et al., issued Sep. 27, 2007; U.S. Pat. No. 6,746,487 entitled "Intramedullary Trial Fixation Device" to Scifert, et al., issued Jun. 9, 2004; U.S. Pat. Appl. Pub. No. 2013/0073041 entitled "Medical Implants With Reservoir(s), and Materials Preparable From Same" to Scifert et al., issued Mar. 21, 2013; U.S. Pat. Appl. Pub. No. 2010/0266689 entitled "Tissue Augmentation With Active Agent For Wound Healing" to Simonton et al., issued Oct. 21, 2010; U.S. Pat. Appl. Pub. No. 2011/0028393 entitled "Flowable Paste And Putty Bone Void Filler" to Vickers et al., issued Feb. 3, 2011; U.S. Pat. Appl. Pub. No. 2009/0099660 entitled "Instrumentation To Facilitate Access Into The Intervertebral Disc Space And Introduction Of Materials Therein" to Scifert issued Apr. 16, 2009; U.S. Pat. Appl. Pub. No. 2011/0014587 entitled "System And Methods Of Preserving An Oral Socket" to Spagnoli et al., issued Jan. 20, 2011; U.S. Pat. No. 8,148,326 entitled "Flowable Carrier Matrix and Methods for Delivering to a Patient" to Beals et al., issued Apr. 3, 2012; U.S. Pat. Appl. Pub. No. 2008/0260598 entitled "Devices, Methods and Systems for Hydrating a Medical Implant Material" to Gross et al., issued Oct. 23, 2008; U.S. Pat. Appl. Pub. No. 2007/0265632 entitled "Bone Cutting Template and Method of Treating Bone Fractures" to Scifert et al., issued Nov. 15, 2007; U.S. Pat. No. 8,293,232 entitled "Flowable Carrier Matrix and Methods for Delivering to a Patient" to Beals et al., issued Oct. 23, 2012; U.S. Pat. No. 8,198,238 entitled "Flowable Carrier Matrix and Methods for Delivering to a Patient" to Beals et al., issued Jun. 12, 2012; U.S. Pat. No. 7,939,092 entitled "Cohesive Osteogenic Putty and Materials Therefor" to McKay et al., issued May 10, 2011; U.S. Pat. Appl. Pub. No. 2007/0264300 entitled "Therapeutic Agent Carrier and Method of Treating Bone Fractures" to Seifert et al., issued Nov. 15, 2007; U.S. Pat. Appl. Pub. No. 2011/0020768 entitled "Implantable Screw and System for Socket Preservation" to Spagnoli et al., issued Jan. 27, 2011; U.S. Pat. Appl. Pub. No. 2012/0065687 entitled "Multi-Radius Vertebral Rod with a Varying Stiffness" to Ballard et al., issued Mar. 15, 2012; U.S. Pat. Appl. Pub. No. 2007/0225219 entitled "Intramedullary Drug Delivery Device and Method of Treating Bone Fractures" to Boden et al., issued Sep. 27, 2007; U.S. Pat. No. 7,723,291 entitled "Release of BMP, Bioactive Agents and/or Cells Via a Pump into a Carrier Matrix" to Beals et al., issued May 25, 2010; U.S. Pat. No. 7,671,014 entitled "Flowable Carrier Matrix And Methods For Delivering To A Patient" to Beals et al., issued Mar. 2, 1010; U.S. Pat. No. 7,897,564 entitled "Flowable Carrier Matrix and Methods for Delivering to a Patient" to Beals et al., issued Mar. 1, 2011; U.S. Pat. Appl. Pub. No. 2011/0160777 entitled "System and Methods of Maintaining Space for Augmentation of the Alveolar Ridge" to Spagnoli et al., issued Jun. 30, 2011; U.S. Pat. Appl. Pub. No. 2009/0246244 entitled "Malleable Multi-Component Implants and Materials Therefor" to McKay et al., issued Oct. 1, 2009; U.S. Pat. Appl. Pub. No. 2009/0246244 entitled "Malleable Multi-Component Implants and Materials Therefor" to McKay et al., issued Oct. 1, 2009; U.S. Pat. Appl. Pub. No. 2013/0110169 entitled "Vertebral Rod System and Methods of Use" to Hynes, et al., issued May 2, 2013; U.S. Pat. Appl. Pub. No. 2011/0184412 entitled "Pre-Assembled Construct With One Or More Non-Rotating Connectors For Insertion Into a Patient" to Seifert, et al., issued Jul. 28, 2011; U.S. Pat. No. 7,964,208 entitled "System and Methods of Maintaining Space For Augmentation of the Alveolar Ridge" to Spagnoli, et al., issued Jun. 21, 2011; U.S. Pat. No. 8,080,521 entitled "Flowable Carrier Matrix and Methods for Delivering to a Patient" to Beals, et al., issued Dec. 20, 2011; U.S. Pat. Appl. Pub. No. 2009/0142385 entitled "Compositions for Treating Bone Defects" to Gross, et al., issued Jun. 4, 2009; U.S. Pat. No. 7,578,820 entitled "Devices and Techniques for a Minimally Invasive Disc Space Preparation and Implant Insertion" to Moore, et al., issued Aug. 25, 2009; U.S. Pat. Appl. Pub. No. 2010/0305575 entitled "Methods and Apparatus for Performing Knee Arthroplasty" to Wilkinson, et al., issued Dec. 2, 2010; U.S. Pat. Appl. Pub. No. 2011/0021427 entitled "Biphasic Calcium Phosphate Cement for Drug Delivery" to Amsden, et al., issued Jan. 27, 2011; U.S. Pat. Appl. Pub. No. 2012/0259335 entitled "Patello-Femoral Joint Implant and Instrumentation" to Scifert, et al., issued Oct. 11, 2012; U.S. Pat. Appl. No. 2011/0106162 entitled "Composite Connecting Elements for Spinal Stabilization Systems" to Ballard, et al., issued May 5, 2011; U.S. Pat. Appl. No. 2004/0073314 entitled "Vertebral Body and Disc Space Replacement Devices" to White, et al., issued Apr. 15, 2004; U.S. Pat. No. 7,513,901 entitled "Graft Syringe Assembly" to Scifert, et al., issued Apr. 7, 2009; U.S. Pat. Appl. No. 2010/0004752 entitled "Vertebral Body and Disc Space Replacement Devices" to White, et al., issued Jan. 7, 2010; U.S. Pat. No. 7,615,078 entitled "Vertebral Body and Disc Space Replacement Devices" to White, et al., issued Nov. 10, 2009; U.S. Pat. No. 6,991,653 entitled "Vertebral Body and Disc Space Replacement Devices" to White, et al., issued Jan. 31, 2006; U.S. Pat. Appl. Pub. No. 2010/0331847 entitled "Methods and Apparatus for Performing Knee Arthroplasty" to Wilkinson, et al., issued Dec. 30, 2010; U.S. Pat. Appl. Pub. No. 2006/0116770 entitled "Vertebral Body and Disc Space Replacement Devices" to White, et al., issued Jun. 1, 2006; and U.S. Pat. No. 8,246,572 entitled "Bone Graft Applicator" to Cantor, et al., issued Aug. 21, 2012.

The prior art bone graft delivery devices listed above typically must come pre-loaded with bone graft, or alternatively require constant loading (where permissible) in order to constantly have the desired supply of bone graft available. Moreover, these bone graft delivery devices generally cannot handle particulate bone graft of varying or irregular particulate size. Furthermore, the prior art devices for inserting a fusion cage or other medical implant into a patient's spine or other surgical area are commonly distinct and separate from traditional devices that deliver bone graft material to the surgical site. As such, two devices are traditionally used to insert bone graft material into a patient's spine and to position and insert a fusion cage. The problems associated with separate administration of the biologic material bone graft material and the insertion of a fusion cage include applying the graft material in the path of the cage, restricting and limiting the biologic material dispersed within the disk space, and requiring that the fusion cage be pushed back into the same place that the fusion material delivery device was, which can lead to additional trauma to the delicate nerve structures. These problems can be a great inconvenience, cause avoidable trauma to a patient and make these prior art devices unsuitable in many procedures.

Therefore, there is a long-felt need for an apparatus and method for precision delivery of bone graft material into a surgical location such as a patient's spine that does not include the deficiencies of prior art devices. The present invention solves these needs.

SUMMARY OF THE INVENTION

Certain embodiments of the present disclosure relate to an apparatus and method for near-simultaneous and integrated delivery of bone graft material during the placement of surgical cages or other medical implants in a patient's spine. The integrated fusion cage and delivery device (the "device") is comprised generally of a tubular member and a plunger for expelling bone graft from the tubular member, through a surgical fusion cage, and into a bone graft receiving area, then disengaging the fusion cage at the surgical site in a human patient. Thus, the apparatus and method allow the biologic material to flow directly into and through the fusion cage and to be dispersed within the disc space in a single step, and to position the detachable fusion cage in the surgical area. In one embodiment, the integrated fusion cage is an expandable integrated fusion cage. Other embodiments and alternatives to this device are described in greater detail below.

It is one aspect of the present invention to provide a bone graft material delivery system comprising an elongate hollow tube constructed to receive bone graft material, said elongate hollow tube being generally linear and having an extended axis, a generally rectangular cross-section, a proximal end, a distal end with at least one opening, a hollow interior extending from said proximal end to said distal end, and indicia formed on an exterior surface of said elongate hollow tube, wherein said distal end of said elongate hollow tube is at least partially closed; and a plunger adapted to extend in said elongate hollow tube, said plunger having a shaft and a distal portion with an exterior surface contoured to form a substantially congruent fit with said hollow interior of said elongate hollow tube such that said plunger is precluded from rotating within said elongate hollow tube, wherein teeth are formed along a longitudinal axis of said plunger shaft, and wherein said plunger is adapted to urge bone graft material through said elongate hollow tube to deliver bone graft material through said at least one opening of said distal end.

In various embodiments, said indicia may be configured to indicate how far said elongate hollow tube has been inserted into a surgical site.

In various embodiments, said indicia may comprise at least one of a marking, a score, and a groove.

In various embodiments, said indicia may comprise a radiographic marker.

In various embodiments, said at least one opening may comprise two openings.

In various embodiments, the system may further comprise actuating means for applying pressure to said shaft of said plunger.

In various embodiments, the system may further comprise an actuator configured to engage said teeth of said plunger to advance said plunger toward said distal end of said elongate hollow tube. The system may also further comprise a gear to engage said plunger teeth. Rotational motion of said gear may be translated into linear movement of said plunger.

In various embodiments, said distal end of said elongate hollow tube may comprise a wedge or a bullet-shaped distal tip.

In various embodiments, said elongate hollow tube may be rigid.

In various embodiments, the system may further comprise a funnel configured to be coupled to said proximal end of said hollow tube.

It is another aspect of the present invention to provide a bone graft insertion apparatus comprising a hollow tube constructed to receive bone graft, said hollow tube having an extended axis, a proximal end, a distal end that is wedge-shaped, an opening to discharge bone graft, and a generally uniform interior rectangular cross-section from said proximal end to said distal end, wherein said distal end is at least partially closed; a plunger adapted for inserting into said proximal end of said hollow tube along the extended axis, said plunger having a shaft and a distal portion of rectangular cross-section contoured to said interior rectangular cross-section of said hollow tube, said plunger distal portion forming a congruent fit with said hollow tube uniform interior rectangular cross-section, said shaft having a longitudinal axis and teeth that are formed along said shaft longitudinal axis; and an actuator configured to engage said teeth of said plunger shaft to advance said plunger from said proximal end toward said distal end of said hollow tube to urge the bone graft through said hollow tube and to deliver the bone graft through said opening.

In various embodiments, the apparatus may further comprise one or more of indicia on said hollow tube that are configured to indicate how far said hollow tube has been inserted into a surgical site; a gear to engage said plunger teeth, wherein said gear is associated with said actuator and is configured to convert rotational motion of said gear into linear movement of said plunger; and a funnel configured to be coupled to said proximal end of said hollow tube.

In various embodiments, said hollow tube may be generally linear and rigid, and said opening may comprise a first pair of edges and a second pair of edges, wherein the first pair of edges are straight and the second pair of edges are not straight.

It is another aspect of the present invention to provide a bone graft delivery device, comprising an elongate tube including a first side opposite to a second side, the first and second sides connected by opposing third and fourth sides such that the elongate tube has a hollow interior with a generally rectangular cross-section, wherein the elongate tube includes a proximal end, at least one opening to discharge bone graft, and a distal end that is wedge-shaped, wherein the distal end is at least partially closed; a plunger with a distal portion and a shaft, the distal portion configured to urge the bone graft through the hollow interior of the elongate tube, the shaft being generally linear and having a plurality of teeth; and actuating means for applying a force to the plunger to advance the plunger within the elongate tube toward the distal end such that bone graft is delivered through the opening into a surgical site.

In various embodiments, the actuating means may include an actuator configured to engage the plurality of teeth of the plunger shaft.

In various embodiments, the actuating means may include a gear configured to engage the plurality of teeth of the plunger shaft to convert rotational motion of the gear into linear movement of the plunger.

In various embodiments, the at least one opening may include an opening formed through one of the first, second, third, and fourth sides.

In various embodiments, the hollow tube may be generally linear and may be rigid.

In another embodiment of the integrated fusion cage and graft delivery device, the detachable fusion cage is detachable by way of a Luer taper or Luer fitting connection, such as in a Luer-Lok® or Luer-Slip® configuration or any other Luer taper or Luer fitting connection configuration. For purposes of illustration, and without wishing to be held to any one embodiment, the following U.S. patent application is incorporated herein by reference in order to provide an illustrative and enabling disclosure and general description of means to selectably detach the fusion cage of the integrated fusion cage and graft delivery device: U.S. Patent Appl. No. 2009/0124980 to Chen.

In another embodiment of the integrated fusion cage and graft delivery device, the detachable fusion cage is detachable by way of a pedicle dart by threadable rotation to achieve attachment, detachment, and axial movement. Other ways include a quick key insertion, an external snap detent, or magnetic attraction or any other structure. For purposes of illustration, and without wishing to be held to any one embodiment, the following U.S. patent application is incorporated herein by reference in order to provide an illustrative and enabling disclosure and general description of means to selectably detach the fusion cage of the integrated fusion cage and graft delivery device: U.S. Patent Appl. No. 2009/0187194 to Hamada.

In another embodiment of the integrated fusion cage and graft delivery device, the detachable fusion cage is detachable by use of magnetism. More specifically, the detachable fusion cage can be made to feature a magnetic field pattern and a resulting force R that are adjustable and may be of different character than the rest of the integrated fusion cage and graft delivery device. With permanent magnets, such adjustments can be made mechanically by orienting various permanent magnet polar geometries and corresponding shapes relative to one another. U.S. Pat. No. 5,595,563 to Moisdon describes further background regarding such adjustment techniques, which is hereby incorporated by reference in its entirety. Alternatively, or additionally, electromagnets could be used in combination with permanent magnets to provide adjustability. In further embodiments, the magnets and corresponding fields and the resultant magnetic field pattern can include both attraction forces from placement of opposite pole types in proximity to one another and repulsion forces from placement of like pole types in proximity to one another. As used herein, "repulsive magnetic force" or "repulsive force" refers to a force resulting from the placement of like magnetic poles in proximity to one another either with or without attractive forces also being present due to opposite magnetic poles being placed in proximity to one another, and further refers to any one of such forces when multiple instances are present. U.S. Pat. No. 6,387,096 is cited as a source of additional information concerning repulsive forces that are provided together with attractive magnetic forces, which is hereby incorporated by reference. In another alternative embodiment example, one or more of surfaces of the fusion cage are roughened or otherwise include bone-engaging structures to secure purchase with vertebral surfaces. In yet other embodiments, the selectable detachable feature between the detachable fusion cage and the integrated fusion cage and graft delivery device can include one or more tethers, cables, braids, wires, cords, bands, filaments, fibers, and/or sheets; a nonfabric tube comprised of an organic polymer, metal, and/or composite; an accordion or bellows tube type that may or may not include a fabric, filamentous, fibrous, and/or woven structure; a combination of these, or such different arrangement as would occur to one skilled in the art. Alternatively or additionally, the selectable detachable feature between the detachable fusion cage and the integrated fusion cage and graft delivery device can be arranged to present one or more openings between members or portions, where such openings extend between end portions of the fusion cage. For purposes of illustration, and without wishing to be held to any one embodiment, the following U.S. patent application is incorporated herein by reference in order to provide an illustrative and enabling disclosure and general description of means to selectably detach the fusion cage of the integrated fusion cage and graft delivery device: U.S. Patent Appl. No. 2011/0015748 to Molz et al.

In another embodiment of the integrated fusion cage and graft delivery device, the detachable fusion cage is detachable by use of plasma treatment. The term "plasma" in this context is an ionized gas containing excited species such as ions, radicals, electrons and photons. (Lunk and Schmid, Contrib. *Plasma Phys.*, 28: 275 (1998)). The term "plasma treatment" refers to a protocol in which a surface is modified using a plasma generated from process gases including, but not limited to, $O_2$, He, $N_2$, Ar and $N_2O$. To excite the plasma, energy is applied to the system through electrodes. This power may be alternating current (AC), direct current (DC), radiofrequency (RF), or microwave frequency (MW). The plasma may be generated in a vacuum or at atmospheric pressure. The plasma can also be used to deposit polymeric, ceramic or metallic thin films onto surfaces (Ratner, Ultrathin Films (by Plasma deposition), 11 *Polymeric Materials Encyclopedia* 8444-8451, (1996)). Plasma treatment is an effective method to uniformly alter the surface properties of substrates having different or unique size, shape and geometry including but not limited to bone and bone composite materials. Plasma Treatment may be employed to effect magnetic properties on elements of the integrated fusion cage and graft delivery device, or to provide selectable detachment of the fusion cage. For purposes of illustration, and without wishing to be held to any one embodiment, the following U.S. patent is incorporated herein by reference in order to provide an illustrative and enabling disclosure and general description of means to selectably detach the fusion cage of the integrated fusion cage and graft delivery device: U.S. Pat. No. 7,749,555 to Zanella et al.

In one embodiment, the device is not a caulking gun style device, that is the bone graft material and/or the fusion cage are not delivered and/or positioned using a hand-pump and/or hand-squeeze mechanism. Instead, the device delivers graft material and/or a fusion cage using a hollow tube and plunger arrangement which is not a caulking gun style device and further, does not appreciably disrupt or block the user's view of the surgical site and/or enable precision delivery of bone graft material and/or a fusion cage to the surgical site. Indeed, the device of one embodiment of the present disclosure is distinctly unlike the caulking gun device of U.S. Pat. Appl. No. 2004/0215201 to Lieberman ("Lieberman"), which requires an L-shaped base member handle, rack teeth to advance a plunger member, and user action on a lever of the L-shaped base member handle to deploy bone graft material. In one embodiment, the device of this application is not a caulking gun style device and does not comprise rack teeth, a base member handle and at least one component that obscures user viewing of the surgical site. Lieberman is incorporated by reference in its entirety for all purposes.

Similarly, in one embodiment, the device is distinctly unlike the caulking gun device of U.S. Pat. Appl. No. 2002/0049448 to Sand et al ("Sand"), which requires a gun and trigger mechanism in which the user squeezes together a gun-style handle to deploy material into bone. The Sand device obstructs the view of the user of the delivery site. In one embodiment, the device of this application is not a caulking gun style device and does not comprise an opposing-levered, gun-style delivery mechanism and at least one component that obscures user viewing of the surgical site. Sand is incorporated by reference in its entirety for all purposes.

Other caulking gun type devices are described in U.S. Pat. Nos. 8,932,295 and 9,655,748 which are each incorporated herein by reference in their entirety.

However, while in some embodiments the bone graft delivery device of the present invention may not be a caulking gun-style device, it is to be expressly understood that caulking gun-type designs are within the scope of the present invention, and indeed may even be desirable in certain embodiments and applications. By way of non-limiting example, it may be advantageous to provide a caulking gun-type mechanism for the purpose of making it easier for a user to apply pressure against a plunger to facilitate controlled movement of the plunger and/or a hollow tube relative to the plunger. A handle and pivotally mounted trigger attached to a ratchet-type push bar, as are commonly associated with caulking guns and similar devices, may be provided, in these and other embodiments, instead of or in addition to a rack-and-pinion-type linear actuator.

In one embodiment, the device is configured to deliver bone graft material substantially laterally from its delivery end, that is substantially not in the axial direction but rather substantially from the side and/or in a radial direction. This is distinctly different than devices that deliver bone graft material along their vertical axis, that is, along or out their bottom end, and/or obstruct the user view of the bone graft and/or fusion cage delivery site, such as that of U.S. Pat. Appl. No. 2010/0087828 to Krueger et al ("Krueger"), U.S. Pat. Appl. No. 2009/0264892 to Beyar et al ("Beyar"), U.S. Pat. Appl. No. 2007/0185496 to Beckman et al ("Beckman"), U.S. Pat. Appl. No. 2009/0275995 to Truckai et al ("Truckai") and U.S. Pat. Appl. No. 2006/0264964 to Scifert et al ("Scifert"). Krueger, Beyar, Beckman, Truckai and Scifert are incorporated by reference in their entireties for all purposes.

In one embodiment, the device is configured to deliver bone graft material so as to completely fill the defined interior of its fusion cage and subsequently deliver bone graft material to the surrounding bone graft site, rather than, for example, to contain the bone material as are the fusion cage designs of U.S. Pat. No. 7,846,210 to Perez-Cruet ("Perez-Cruet"). Further, the fusion device of this application features a distal tip that functions to precisely position the fusion device and stabilize the device during delivery of bone graft material. Perez-Cruet is incorporated by reference in its entirety for all purposes.

In addition, by way of providing additional background and context, the following references are also incorporated by reference in their entireties for the purpose of explaining the nature of spinal fusion and devices and methods commonly associated therewith, to include, without limitation, expandable fusion cages: U.S. Pat. No. 4,863,476 to Shepperd; U.S. Pat. No. 6,743,255 to Ferree; U.S. Pat. No. 6,773,460 to Jackson; U.S. Pat. No. 6,835,206 to Jackson; U.S. Pat. No. 6,972,035 to Michelson; U.S. Pat. No. 7,771,473 to Thramann; U.S. Pat. No. 7,850,733 to Baynham; U.S. Pat. No. 8,506,635 to Palmatier; U.S. Pat. No. 8,556,979 to Glerum; U.S. Pat. No. 8,628,576 to Triplett; U.S. Pat. No. 8,709,086 to Glerum; U.S. Pat. No. 8,715,351 to Pinto; U.S. Pat. No. 8,753,347 to McCormack; U.S. Pat. No. 8,753,377 to McCormack; U.S. Design Pat. No. D708,323 to Reyes; U.S. Pat. No. 8,771,360 to Jimenez; U.S. Pat. No. 8,778,025 to Ragab; U.S. Pat. No. 8,778,027 to Medina; U.S. Pat. No. 8,808,383 to Kwak; U.S. Pat. No. 8,814,940 to Curran; U.S. Pat. No. 8,821,396 to Miles; U.S. Patent Application Publication No. 2006/0142858 to Colleran; U.S. Patent Application Publication No. 2008/0086142 to Kohm; U.S. Patent Application Publication No. 2010/0286779 to Thibodean; U.S. Patent Application Publication No. 2011/0301712 to Palmatier; U.S. Patent Application Publication No. 2012/0022603 to Kirschman; U.S. Patent Application Publication No. 2012/0035729 to Glerum; U.S. Patent Application Publication No. 2012/0089185 to Gabelberger; U.S. Patent Application Publication No. 2012/0123546 to Medina; U.S. Patent Application Publication No. 2012/0197311 to Kirschman; U.S. Patent Application Publication No. 2012/0215316 to Mohr; U.S. Patent Application Publication No. 2013/0158664 to Palmatier; U.S. Patent Application Publication No. 2013/0178940; U.S. Patent Application Publication No. 2014/0012383 to Triplett; U.S. Patent Application Publication No. 2014/0156006; U.S. Patent Application Publication No. 2014/0172103 to O'Neil; U.S. Patent Application Publication No. 2014/0172106 to; U.S. Patent Application Publication No. 2014/0207239 to Barreiro; U.S. Patent Application Publication No. 2014/0228955 to Weiman; U.S. Patent Application Publication No. 2014/0236296 to Wagner; U.S. Patent Application Publication No. 2014/0236297 to Iott; U.S. Patent Application Publication No. 2014/0236298 to Pinto.

Furthermore, by way of providing additional background and context, the following references are also incorporated by reference in their entireties for the purpose of explaining the nature of spinal fusion and devices and methods commonly associated therewith, to include, without limitation, expandable fusion cages: U.S. Pat. No. 7,803,159 to Perez-Cruet et al.; U.S. Pat. No. 8,852,282 to Farley et al.; U.S. Pat. No. 8,858,598 to Seifert et al.; U.S. Pat. No. D714,933 to Kawamura; U.S. Pat. No. 8,795,366 to Varela; U.S. Pat. No. 8,852,244 to Simonson; U.S. Patent Application Publication No. 2012/0158146 to Glerum et al.; U.S. Pat. No. 8,852,242 to Morgenstern Lopez et al.; U.S. Pat. No. 8,852,281 to Phelps; U.S. Pat. No. 8,840,668 to Donahoe et al.; U.S. Pat. No. 8,840,622 to Vellido et al.; U.S. Patent Application Publication No. 2014/0257405; U.S. Patent Application Publication No. 2014/0257490 to Himmelberger et al.; U.S. Pat. No. 8,828,019 to Raymond et al.; U.S. Patent Application Publication No. 2014/0288652 to Boehm et al.; U.S. Patent Application Publication No. 2014/0287055 to Kunjachan; U.S. Patent Application Publication No. 2014/0276896 to Harper; U.S. Patent Application Publication No. 2014/0277497 to Bennett et al.; U.S. Patent Application Publication No. 2012/0029635 to Schoenhoeffer et al.; U.S. Patent Application Publication No. 2014/0303675 to Mishra; U.S. Patent Application Publication No. 2014/0303731 to Glerum; U.S. Patent Application Publication No. 2014/0303732 to Rhoda et al.; U.S. Pat. No. 8,852,279 to Weiman; PCT Pub. WO 2012/031267 to Weiman; U.S. Pat. No. 8,845,731 to Weiman; U.S. Pat. No. 8,845,732 to Weiman; U.S. Pat. No. 8,845,734 to Weiman; U.S. Patent Application Publication No. 2014/0296985 to Balasubramanian et al.; U.S. Patent Application Publication No. 2014/0309268 to Arnou; U.S. Patent Application Publication No. 2014/0309548 to Merz et al.; U.S. Patent Application Publication No. 2014/0309697 to Iott et al.; U.S. Patent Application Publication No. 2014/0309714 to Mercanzini et al.; U.S. Pat. No. 8,282,683 to McLaughlin et al.; U.S. Pat. No. 8,591,585 to McLaughlin et al; U.S. Pat. No. 8,394,129 to Morgenstern Lopez et al.; U.S. Patent Application Publication No. 2011/0208226 to Fatone et al.; U.S. Patent Application Publication No. 2010/0114147 to Biyani; U.S. Patent Application Publication No. 2011/0144687 to Kleiner; U.S. Pat. No. 8,852,243 to Morgenstern Lopez et al.; U.S. Pat. No. 8,597,333 to Morgenstern Lopez et al.; U.S. Pat. No. 8,518,087 to Lopez et al.; U.S. Patent Application Publication No. 2012/0071981 to Farley et al.; U.S. Patent Application Publication No. 2013/0006366 to Farley et al.; U.S. Patent Application Publication No. 2012/0065613 to Pepper et al.; U.S. Patent Application Publication No. 2013/0006365 to Pepper et al.; U.S. Patent Application Publication No. 2011/0257478 to Kleiner et al.; U.S. Patent Application Publication No. 2009/0182429 to Humphreys et al.; U.S. Patent Application Publication No. 2005/0118550 to Turri; U.S. Patent Application Publication No. 2009/0292361 to Lopez; U.S. Patent Application Publication No. 2011/0054538 to Zehavi et al.; U.S. Patent Application Publication No. 2005/0080443 to Fallin et al.; U.S. Pat. No. 8,778,025 to Ragab et al.; U.S. Pat. No. 8,628,576 to Triplett et al; U.S. Pat. No. 8,808,304 to Weiman, and U.S. Pat. No. 8,828,019 to Raymond.

All of the following U.S. patents are also incorporated herein by reference in their entirety: U.S. Pat. Nos. 6,595,998; 6,997,929; 7,311,713; 7,749,255; 7,753,912; 7,780,734; 7,799,034; 7,875,078; 7,931,688; 7,967,867; 8,075,623; 8,123,755; 8,142,437; 8,162,990; 8,167,887; 8,197,544; 8,202,274; 8,206,395; 8,206,398; 8,317,802; 8,337,531; 8,337,532; 8,337,562; 8,343,193; 8,349,014; 8,372,120; 8,394,108; 8,414,622; 8,430,885; 8,439,929; 8,454,664; 8,475,500; 8,512,383; 8,523,906; 8,529,627; 8,535,353; 8,562,654; 8,574,299; 8,641,739; 8,657,826; 8,663,281; 8,715,351; 8,727,975; 8,828,019; 8,845,640; 8,864,830; 8,900,313; 8,920,507; 8,974,464; 9,039,767; 9,084,686; 9,095,446; 9,095,447; 9,101,488; 9,107,766; 9,113,962; 9,114,026; 9,149,302; 9,174,147; 9,216,094; 9,226,777; 9,295,500; 9,358,134; 9,381,094; 9,439,692; 9,439,783; 9,445,921; 9,456,830; 9,480,578; 9,498,200; 9,498,347; 9,498,351; 9,517,140; 9,517,141; 9,517,142; 9,545,250; 9,545,279; 9,545,313; 9,545,318; 9,610,175; 9,629,668; 9,655,660; 9,655,743; 9,681,889; 9,687,360; 9,707,094; 9,763,700; 9,861,395; 9,980,737; 9,993,353; U.S. Pat. Pub. 2014/0088712; U.S. Pat. Pub. 2014/0276581; U.S. Pat. Pub. 2014/0371721; U.S. Pat. Pub. 2016/0296344; U.S. Pat. Pub. 2017/0367846; U.S. Pat. Pub. 2017/0354514.

This Summary of the Invention is neither intended nor should it be construed as being representative of the full extent and scope of the present disclosure. The present disclosure is set forth in various levels of detail in the Summary of the Invention as well as in the attached drawings and the Detailed Description, and no limitation as to the scope of the present disclosure is intended by either the inclusion or non-inclusion of elements, components, etc. in this Summary of the Invention. Additional aspects of the present disclosure will become more readily apparent from the Detailed Description, particularly when taken together with the drawings.

The above-described benefits, embodiments, and/or characterizations are not necessarily complete or exhaustive, and in particular, as to the patentable subject matter disclosed herein. Other benefits, embodiments, and/or characterizations of the present disclosure are possible utilizing, alone or in combination, as set forth above and/or described in the accompanying figures and/or in the description herein below. However, the Detailed Description, the drawing figures, and the exemplary claim set forth herein, taken in conjunction with this Summary of the Invention, define the invention.

BRIEF DESCRIPTION OF THE DRAWINGS

The accompanying drawings, which are incorporated in and constitute a part of the specification, illustrate embodiments of the disclosure and together with the general description of the disclosure given above and the detailed description of the drawings given below, serve to explain the principles of the disclosures.

It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

FIG. 7B is a top plan view of the hollow tubular member of FIG. 7A and a detachable funnel;

FIG. 7C is a side elevation view of the hollow tubular member of FIG. 7A interconnected to the funnel and including a plunger inserted into a lumen of the hollow tubular member;

FIG. 7D is a front elevation view of the hollow tubular member of FIG. 7A and illustrating an optional opening at the distal end;

FIG. 7E is an expanded cross-sectional view of a portion of the hollow tubular member;

FIG. 7F illustrates devices used to prepare bone graft material according to one embodiment of the present disclosure;

FIG. 7G is an environmental view of a surgical site and a bone graft delivery device according to one embodiment of the present disclosure;

FIG. 8 is an environmental view of an intervertebral disc space and a prior art bone graft delivery device;

FIG. 10 is an exploded view of a graft delivery device of another embodiment of the present disclosure;

FIG. 11 is an expanded partial perspective view illustrating a distal portion of a hollow tube of the graft delivery device of FIG. 10;

FIG. 12 is a cross-sectional view of the distal portion of the hollow tube;

FIG. 18 is and exploded view of a graft delivery device of yet another embodiment of the present disclosure;

FIG. 19 is an expanded partial perspective view illustrating a distal portion of a hollow tube of the graft delivery device of FIG. 18;

FIG. 20 is a cross-sectional view of the distal portion of the hollow tube;

Figure 1A:
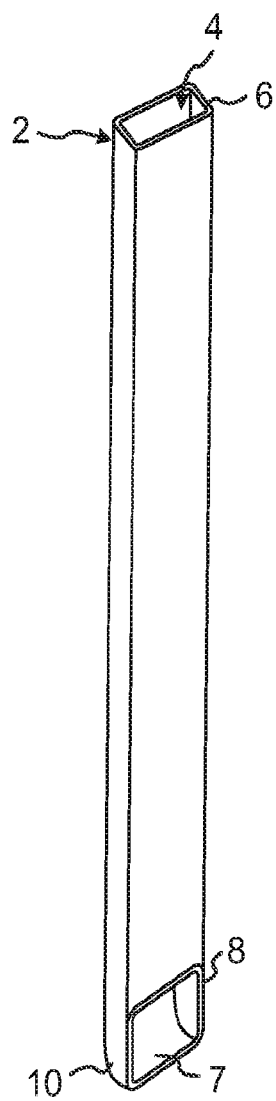
FIG. 1A is a front perspective view of a hollow tubular member of the device for delivering bone graft according to one embodiment of the present invention.

To provide further clarity to the Detailed Description provided herein in the associated drawings, the following list of components and associated numbering are provided as follows:

| Reference No. | Component |
|---|---|
| 1 | Integrated fusion cage and graft delivery device |
| 2 | Hollow tube |
| 3 | Hollow tube first (side) surface |
| 3A | First side |
| 3B | Second side |
| 4 | Opening (of Hollow tube) |
| 5 | Hollow tube second (top and bottom) surface |
| 6 | First (or proximal) end (of Hollow tube) |
| 6A | Knob |
| 6B | Pin |
| 7 | Hollow tube first distal opening |
| 8 | Second (or distal) end (of Hollow tube) |
| 9 | Ramp |
| 9A | Ramp surface |
| 9B | Ramp surface |
| 10 | Curved surface (of Hollow tube) |
| 12 | Plunger |
| 16 | Handle (of Plunger) |
| 16A | Plunger stop |
| 17 | Plunger medial portion |
| 18 | Second (or distal) end (of Plunger) |
| 18A | Pusher |
| 19 | Horizontal surface (of Plunger) |
| 20 | Curved surface (of Plunger) |
| 21 | Vent port |
| 22 | First portion |
| 23 | Second portion |
| 24 | Joint or plane |
| 25 | Peg or pin |
| 26 | Recess |
| 27 | Teeth or notches of plunger |
| 28 | Lumen |
| 29 | Indicia to indicate depth of insertion of distal end |
| 30 | Funnel |
| 32 | Sleeve (of Funnel) |
| 33 | Slot for pin of bayonet mount |
| 35 | Vent channel in plunger pusher |
| 36 | Endoscope, camera, or image sensing device |
| 37 | Lighting element |
| 42 | Syringe |
| 44 | Bone graft material |
| 46 | Luer lock device |
| 48 | Bore |
| 50 | Wedge-shaped Second end (of Hollow tube) |
| 52 | Wedge-shaped Second end (of Plunger) |
| 60 | Fusion Cage |
| 64 | Fusion Cage Second (or Distal) End |
| 65 | Fusion Cage First Opening Pair |
| 70 | Width of hollow tube |
| 74 | Blunt surfaces of plunger distal end |
| 78 | Opposing surfaces of the plunger |
| 80 | Area of flexibility of the plunger |
| 82 | Relief areas |
| 84 | Ends of notches |
| 86 | Rabbet |
| 88 | Width of plunger |
| 90 | Gap |
| 92 | Groove |
| 94A | First arm |
| 94B | Second arm |
| 170 | Bone graft deliver device |
| 171 | Spine |
| 172 | Surgical site |
| 174 | Path for fusion cage |
| 304 | Grip |
| 306 | Trigger |
| 308 | Handle |
| 310 | Knob |
| 312 | Switch or button |

-continued

| Reference No. | Component |
| --- | --- |
| 314 | Loading port |
| 316 | Capsule or package of bone graft material |
| 318 | Knob of grip |
| 320 | Flange |
| 322 | Slot |
| 324 | Channel |
| 326 | Proximal opening of channel |
| A | Height of Opening (in Hollow tube) |
| B | Width of Opening (in Hollow tube) |

DETAILED DESCRIPTION

The present invention relates to a system, device/apparatus and method for integrated and near-simultaneous delivery of bone graft material and a fusion cage to any portion of a patient which requires bone graft material and/or a fusion cage. Thus, for example, the foregoing description of the various embodiments contemplates delivery to, for example, a window cut in a bone, where access to such window for bone grafting is difficult to obtain because of orientation of such window, presence of muscle tissue, risk of injury or infection, etc. The integrated fusion cage and graft delivery device is formed such that the one or more hollow tubes and/or plungers may be helpful in selectively and controllably placing bone graft material and a fusion cage in or adjacent to such window. The integrated fusion cage and graft delivery device is formed to allow delivery of bone graft material and/or a fusion cage in a direction other than solely along the longitudinal axis of the device, and in some embodiments transverse to the primary axis used by the surgeon or operator of the device when inserting the device into a cannula or other conduit to access the surgical site. This same concept applies to other areas of a patient, whether or not a window has been cut in a bone, for example in a vertebral disc space, and may be used whether this is a first surgery to the area or a follow-up surgery. The present invention also contemplates the delivery of bone graft material and/or a fusion cage with or without the use of a plunger, and with or without the use of various other tools described in greater detail herein. The present invention also contemplates the delivery of a spinal fusion implant into a collapsed vertebra, and filling it with filler material.

Referring now to FIG. 1A, an integrated fusion cage 60 and graft delivery system, or device 1 is shown, which is comprised of a hollow tubular member or hollow tube 2 or contains at least one inner lumen, which has a first proximate end 6 (which is referred to elsewhere in this specification as the "graspable end" of hollow tube 2), and a second distal end 8 having an opening 7, with a general hollow structure therebetween. Thus, as shown in FIG. 1, the hollow tube 2 allows bone graft material to be inserted into the opening 4 at the graspable end 6 of the hollow tube 2, and ultimately exited from the hollow tube 2 through the opening 7 of the distal end 8. According to a preferred embodiment, the hollow tube 2 also comprises at least one sloped or curved surface 10 at or near the distal end 8 of the hollow tube 2. Although the distal end 8 and its opening 7 are shown as having a generally rectangular cross-section, the cross-section need not be limited to a generally rectangular shape. For example, in various embodiments, the distal end 8 and opening 7 have cross-sections of an oval shape or those with at least one defined angle to include obtuse, acute, and right angles. The cross-section of the distal end 8 and opening 7 can be provided in a shape that is more congruent with the size or shape of the annulotomy of a patient's particular disc space.

Figure 1B:
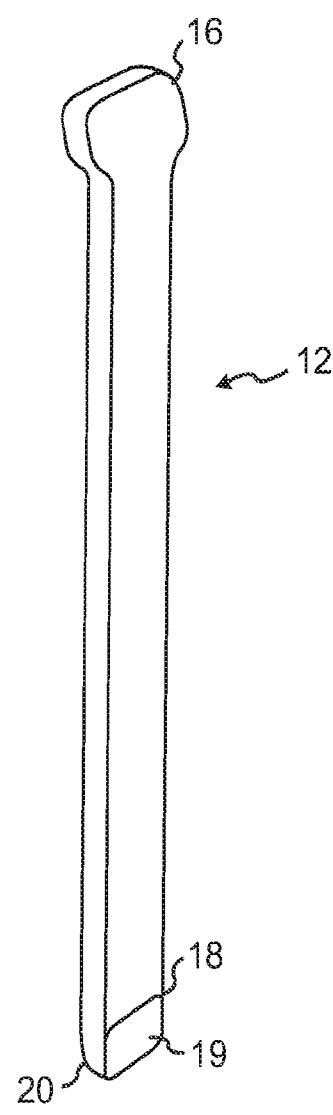
FIG. 1B is a front perspective view of the plunger of the device.

Referring now in detail to FIG. 1B, a plunger 12 according to one embodiment is shown for use with the hollow tube 2 of FIG. 1A. The plunger 12 is generally of the same geometry and dimensions as the hollow portion of the hollow tube 2, extending at least the same length of hollow tube 2. The plunger 12 may include, as depicted in FIG. 1B, at least one knob or handle 16 for grasping by a user of the plunger 12. As with the interior of the hollow tube 2 at its second end 8, the plunger 12 also comprises at least one sloped or curved surface 20 at or adjacent to a second end 18 of the plunger 12. The plunger 12 terminates in a generally flat surface 19, which corresponds to the opening 7 of the second end 8 of the hollow tube 2 shown in FIG. 1A. Thus, in cooperation, the plunger 12 may be inserted into the opening 4 of the hollow tube 2 shown in FIG. 1A, and extended the entire length of the hollow tube 2, at least to a point where the flat surface 19 of plunger 12 is in communication with the opening 7 of the second end 8 of the hollow tube 2. This configuration permits a user to eject substantially all of the bone graft material that is placed into the hollow tube 2 during a surgical procedure. One skilled in the art will appreciate that the plunger need not terminate in a generally flatsurface to affect the substantial removal of all of the bone graft material placed into the hollow tube; more specifically, any shape that allows conformance between the internal contour of the distal end of the hollow tube and the distal end of the plunger will affect the substantial removal of the bone graft material.

Figure 1C:
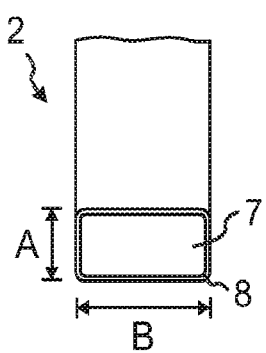
FIG. 1C is a cross sectional view of a portion of the device shown in FIG. 1A.

In the embodiment of FIGS. 1A-C, a contoured leading edge 20 is provided on the plunger 12 to correspond with the internal contour of distal end 8 of the hollow tube 2 of the delivery device. This contoured plunger 12 serves several purposes: First, it maintains the plunger 12 in a desirable rotational position with respect to the hollow tube 2 (i.e., prevents the plunger 12 from inadvertently or intentionally being manipulated to rotate about the longitudinal axis of the hollow tube 2). Second, it ensures that when the plunger 12 is fully inserted, the plunger 12 removes substantially all of the bone graft material from the hollow tube 2. Also, the contour of the plunger 12, corresponding to the contour of the hollow tube 2, allows immediate identification of the orientation of the device, and more specifically, the direction of the bone graft material ejection into the surgical area (e.g., the patient's intervertebral area). Alternative positioning means may also be provided to ensure that the plunger 12 remains in the desirable position during delivery of bone graft into the hollow tube 2, for example by a machined bevel or edge on the outer surface of the plunger 12, and a corresponding groove in the interior surface of the hollow tube 2 (not shown), which must be aligned when inserting the plunger 12 in the hollow tube 2.

Referring now to FIG. 1C, an elevation view of the hollow tube 2 shown in FIG. 1A is shown in detail. The opening 7 of the second end 8 of the hollow tube 2 has a height A and width B. The height A and width B are selected based on various factors, including, but not limited to, the needs of the surgeon, the location of the bone graft receiving area, the nature of the surgical operation to be performed, and the quantity and type of bone graft that is being inserted in (and ultimately ejected from) this integrated fusion cage and graft delivery device. According to a preferred embodiment, the height A of the opening 7 is in the range of 4 mm to 9 mm, and in a most preferred embodiment is about 7 mm. According to a preferred embodiment, the width B of the opening 7 is in the range of 7 mm to 14 mm, and in a most preferred embodiment is about 10 mm.

Although FIGS. 1A-C show an embodiment where the second end 8 of the hollow tube 2, and the second end 18 of the plunger 12 comprise a curved or sloped surface which extends at least a certain distance laterally away from the generally longitudinal axis of the hollow tube 2/plunger 12, it is to be understood that in other embodiments, the second end 8 of the hollow tube 2 (and thus, the second end 18 of the plunger 12) do not extend a lateral distance away, but rather terminate along the longitudinal wall of the hollow tube 2. In this embodiment, the hollow tube 2 may have a second end 8 which has an opening 7 that is carved out of the side of the wall of the hollow tube 2, such that it appears as a window in the tubular body of hollow tube 2. According to this embodiment, the plunger 12 would still retain the curved or sloped surface 20 at the opposite end of the flat surface 19 (see FIG. 1B) and similarly the hollow tube 2 would still comprise a sloped or curved surface 10 opposite the opening 7 at the second end 8. It is to be expressly understood that other variations which deviate from the drawing FIGS. 1A-C are also contemplated with the present invention, so long as that the opening 7 at the second end 8 of hollow tube 2 is oriented to permit bone graft to be ejected from the hollow tube 2 in a generally lateral direction (in relation to the longitudinal direction of the axis of the hollow tube 2).

According to another embodiment, the plunger 12 shown in FIG. 1B may further comprise a secondary handle (not shown), which includes an opening about at least one end of secondary handle such that it is permitted to couple with handle 16 of plunger 12. In this fashion, the secondary handle may be larger, contain one or more rings or apertures for placing a user's hand and/or fingers, or may simply be of a more ergonomic design, for accommodating use of the plunger 12 during a surgical operation. The secondary handle, according to this embodiment, is selectively removable, which permits a surgeon to use the secondary handle for inserting the plunger 12, and then at a later point remove the secondary handle, for instance, to improve visibility through the incision or through the hollow tube 2, and/or to determine whether substantially all of the bone graft material has been ejected from the hollow tube 2.

Figure 2:
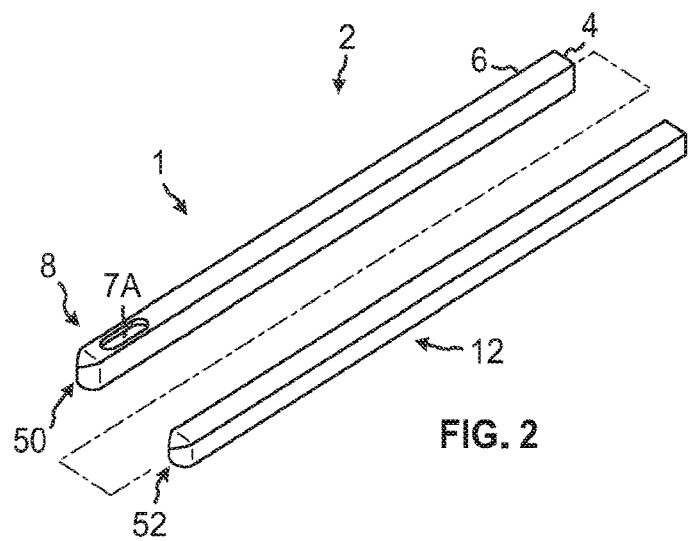
FIG. 2 is a front perspective view of one embodiment of the device, showing the relationship between the tubular and plunger portions where the tubular portion includes two lateral facing openings at the distal end of the tubular portion and a wedge-shaped distal end of the tubular member.

Referring now to FIGS. 2-6, a preferred embodiment of the device is shown. In regard to FIG. 2, an integrated fusion cage and graft delivery device portion is shown, comprised of a hollow tube 2, which has a first proximate end 6 and a second distal end 8, with a general hollow structure therebetween. The hollow tube 2 is shown with one of two lateral openings, 7A, at the distal end 8 of the tubular member 2 viewable (the other of the openings, 7B, is viewable in FIG. 3). The plunger 12 is also shown in FIG. 2. The manner of insertion of the plunger 12 into the hollow tube 2 is also shown in FIG. 2. The hollow tube 2 allows bone graft material to be inserted into the opening 4 at the proximal end 6 of the hollow tube 2, and ultimately ejected from the hollow tube 2 through the lateral openings 7A, 7B at the distal end 8.

FIG. 2 shows a preferred embodiment of the distal end 8 of the tubular member 2 and the distal end 18 of the plunger member 12. The configuration provided, a wedge-shaped end 50 of the hollow tube 2 and a wedge-shaped end 52 of the plunger 12, allows substantially all of the bone graft material to be removed and thus inserted into the surgical area when the plunger 12 is fully inserted into the hollow tube 2. The wedge-shape 50 of the distal end 8 of the tubular member 2 and the wedge-shaped end 52 of the plunger 12 is discussed in additional detail with respect to FIGS. 4 and 5 below. The ability to remove substantially all of the bone graft material is an important feature of the invention because bone graft material is traditionally expensive and may require surgery to obtain.

Figure 3:
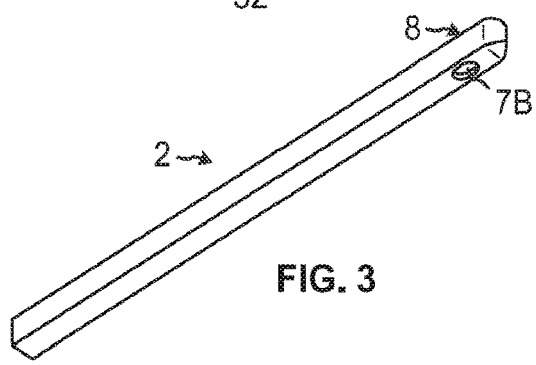
FIG. 3 is another front perspective view of the tubular portion of the device of FIG. 2 showing the second of two lateral openings at the distal end of the tubular portion and a wedge-shaped distal end of the tubular member.

Referring now to FIG. 3, a perspective view of a preferred embodiment of the hollow tube 2 is provided. Consistent with FIG. 2, the hollow tube 2 is shown with one of two lateral openings, 7B, at the distal end 8 of the hollow tube 2 viewable (the other lateral opening, 7A, is viewable in FIG. 2). Thus, in operation the hollow tube 2 allows bone graft material to be inserted into the opening 4 at the proximal end 6 of the hollow tube 2, and ultimately ejected from the hollow tube 2 through the lateral openings 7A, 7B at the distal end 8 of the hollow tube 2. In this configuration, bone graft material is ejected into the surgical area in two lateral directions. One skilled in the art will appreciate that the openings 7A, 7B at the distal end 8 of the hollow tube 2 need not be positioned exclusively on one or more lateral sides of the distal end 8 of the tube 2 to allow bone graft material to be provided to the surgical site in other than a purely axial or longitudinal direction. Further, one skilled in the art will appreciate that the specific absolute and relative geometries and numbers of lateral openings may vary, for example the distal end 8 of the hollow tube 2 may have more than two openings that are of different shape (e.g. oval, rectangular), and/or one or more lateral openings may comprise a first pair of edges and a second pair of edges, wherein the first pair of edges are straight and the second pair of edges are not straight.

Figure 4:
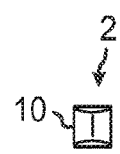
FIG. 4 is a front elevation view of the distal end of the tubular portion of the device of FIG. 2.

Referring now to FIG. 4, an elevation view of the wedge-shaped distal end 50 of the hollow tube 2 is provided. In this embodiment, the distal end 52 of the plunger 12 conforms to the same wedge shape as the distal end 50, to allow close fitting of the plunger 12 and the hollow tube 2. This contoured plunger 12, corresponding to the contoured hollow tube 2, serves several purposes: First, it maintains the plunger 12 in a desirable rotational position with respect to the hollow tube 2 (i.e., prevent the plunger 12 from inadvertently or intentionally being manipulated to rotate about the longitudinal axis of the hollow tube 2); Second, it ensures that when the plunger 12 is fully inserted, the plunger 12 removes substantially all of the bone graft material from the hollow tube 2. Also, the contoured plunger 12, corresponding to the contoured hollow tube 2, allows immediate identification of the orientation of the device, and more specifically the direction of the bone graft material ejection into the surgical area. One skilled in the art will appreciate that the plunger 12 need not terminate in a wedge-shape surface 52 to affect the substantial removal of all of the bone graft material placed into the hollow tube 2; more specifically, any shape that allows conformance between the internal contour of the distal end 50 of the hollow tube 12 and the distal end 52 of the plunger 12 will affect the substantial removal of the bone graft material.

Figure 5:
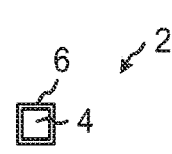
FIG. 5 is a bottom elevation view of the proximal end of the tubular device of FIG. 2.

Referring now to FIG. 5, an elevation view of the opening 4 of the proximal end 6 of the hollow tube 2 is provided. As shown in FIG. 5, the opening 4 at the proximal end 6 of the hollow tube 2 allows deposit of bone graft material. In this configuration, the cross-section of the opening 4 at the proximal end 6 of the hollow tube 2 is generally square. Although a generally square cross-section is depicted, the cross-section need not be limited to a generally square shape. For example, in various embodiments, the proximal end 6 and opening 4 have cross-sections of an oval shape or those with at least one defined angle to include obtuse, acute, and right angles. The cross-section of the proximal end 6 and opening 7 can be provided in a shape that is more congruent with the size or shape of the annulotomy of a patient's particular disc space.

Figure 6A:
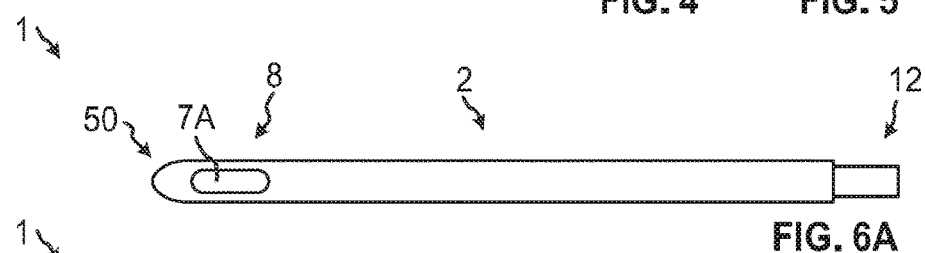
FIG. 6A is a top plan view of the device of FIG. 2 with the plunger portion fully inserted into the tubular portion.
Figure 6B:
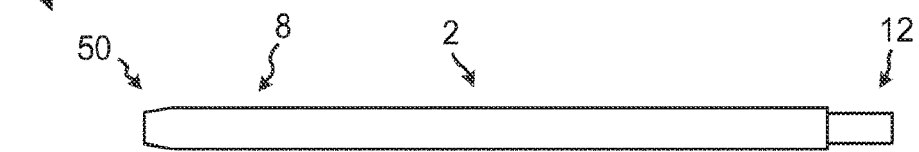
FIG. 6B is a left elevation view of the device of FIG. 2 with the plunger portion fully inserted into the tubular portion.
Figure 6C:
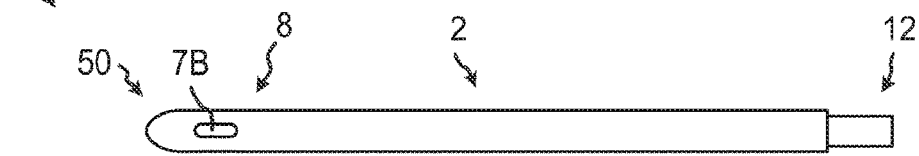
FIG. 6C is a bottom plan view of the device of FIG. 2 with the plunger portion fully inserted into the tubular portion.
Figure 6D:
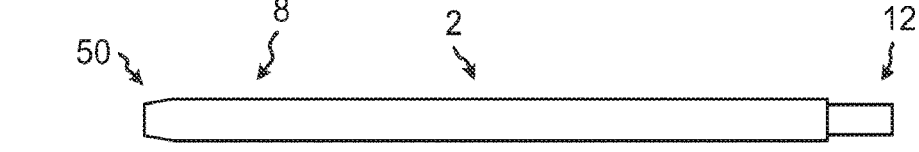
FIG. 6D is a right elevation view of the device of FIG. 2 with the plunger portion fully inserted into the tubular portion.

Referring now to FIGS. 6A-D, sequential elevation views of one embodiment of the integrated fusion cage and graft delivery device 1 are provided, depicting the complete insertion of the plunger 12 into the hollow tube 2. In each of FIGS. 6A-D, the wedge-shaped distal end 50 of the hollow tube 2 is depicted. Also, each of FIGS. 6A-D depict the additional length of the plunger 12 when inserted into the tubular member 2 (i.e., the portion of the plunger 12 that extends outside of the hollow tube 2). FIG. 6A shows one of two lateral openings 7A at the distal end 8 of the hollow tube 2. FIG. 6C shows another of the two lateral openings 7B at the distal end 8 of the hollow tube 2. One skilled in the art will appreciate that the openings 7A, 7B at the distal end 8 of the hollow tube 2 need not be positioned exclusively on one or more lateral sides of the distal end 8 of the hollow tube 2 to allow bone graft material to be provided to the surgical site in other than a purely axial or longitudinal direction. Further, one skilled in the art will appreciate that the specific absolute and relative geometries and numbers of lateral openings 7A, 7B may vary, for example the distal end 8 of the hollow tube 2 may have more than two openings that are of different shape (e.g. oval, rectangular). In various embodiments, the sizes and dimensions of lateral openings 7A and 7B are different from one another, as shown in FIGS. 2, 3, 6A and 6C. In other embodiments, the sizes and dimensions of lateral openings 7A and 7B are the same.

Referring now to FIGS. 7A to 7F, an embodiment of an integrated fusion cage and graft delivery device 1 of the present disclosure is illustrated. The graft delivery device generally includes a cannular or hollow tube 2, a plunger 12, and a detachable funnel 30.

The hollow tube 2 is the same as, or similar to, other embodiments of hollow tubes described herein. Accordingly, the hollow tube 2 generally includes an opening 4 at a proximal end 6. At least one discharge opening 7 is associated with a distal end 8 of the hollow tube. The hollow tube 2 has a pair of first, exterior side surfaces 3 that extend between the proximal and distal ends 6, 8 (see FIG. 7C), as well as a pair of second, exterior top and bottom surfaces 5 that also extend between the proximal and distal ends 6, 8 (see FIG. 7B). In one embodiment, the discharge opening 7 is positioned transverse to a longitudinal axis of the hollow tube 2. Accordingly, in one embodiment, the distal end 8 is at least partially closed opposite to the proximal opening 4. Alternatively, the distal end 8 may be completely closed. Optionally, a discharge opening 7 may be formed through at least a portion of the distal end. Specifically, in one embodiment, the hollow tube 2 can include a discharge opening 7 aligned with a longitudinal axis of the hollow tube.

In one embodiment, the distal end 8 is rounded or smooth with a wedge shape 50. Specifically, the distal end 8 can have a shape configured to facilitate easy entry into a disc space. In this manner, the shape of the distal end 8 minimizes soft tissue damage or irritation. The wedge shape 50 enables insertion of the distal end 8 into a collapsed disc space without damaging the endplates or skating off to an unintended location. In contrast, some prior art devices with an open distal end can injure bony end plates of the disc space of a patient.

In an embodiment, the hollow tube 2 includes two discharge openings 7A, 7B. The two discharge openings 7A, 7B can be arranged on opposite sides of the hollow tube 2 to eject graft material therefrom. Accordingly, in one embodiment, the hollow tube 2 is operable to dispense bone graft material laterally away from a longitudinal axis of the graft delivery device 1. In one embodiment, the two discharge openings 7A, 7B are of substantially the same size and shape. In one embodiment, the discharge openings 7A, 7B have a generally oval shape. In various other embodiments, the discharge openings 7A, 7B do not have the same size or shape as each other. In various embodiments, the discharge openings 7A, 7B have rectangular, rhomboid, circular or other shapes.

In another embodiment, at least one opening 7C (illustrated in FIG. 7D) is formed in the distal end 8. Thus, the graft delivery device 1 may discharge bone graft material through the distal end 8 in line with the longitudinal axis of the graft delivery device 1. The opening 7C may have any predetermined shape. In various embodiments, the opening 7C has a rectangular, round, or ovoid shape. In an embodiment, the distal end 8 includes a taper or wedge shape 50 with the end opening 7C formed therethrough.

The hollow tube 2 is substantial hollow between the proximal end 6 and the distal end 8. Specifically, a lumen 28 extends through the hollow tube 2 (see FIG. 7A). The lumen 28 has a predetermined cross-sectional shape. In various embodiments, the cross-sectional shape of the lumen is round, ovoid, square, or rectangular. In another embodiment, the interior of the lumen 28 is not round and is, for example, rectangular. In one embodiment the cross-sectional shape of the lumen 28 is substantially uniform along the length of the hollow tube 2. In one embodiment, the lumen 28 has a uniform cross-sectional size along its length. In various embodiments, the exterior of the hollow tube 2 has a shape that is one of round, ovoid, square, and rectangular.

In various embodiments, a ramp 9 is formed within the hollow tube 12, proximate to the opening 7. As described herein, the ramp 9 includes surfaces configured to direct the bone graft material away from the opening 7 into a surgical site, such as a disc space. More specifically, the ramp 9 functions as a reverse funnel to disperse bone graft material ejected from the opening 7 as generally illustrated in FIG. 7A.

In one embodiment, surfaces of the ramp 9 are linear in shape, that is, forming a triangle in cross-section. In other configurations, surfaces of the ramp 9 are of any shape that urges egress of bone graft material contained in the hollow tube to exit the lumen 28 of the hollow tube 2 through the at least one opening 7 of the device 1.

Figure 7A:
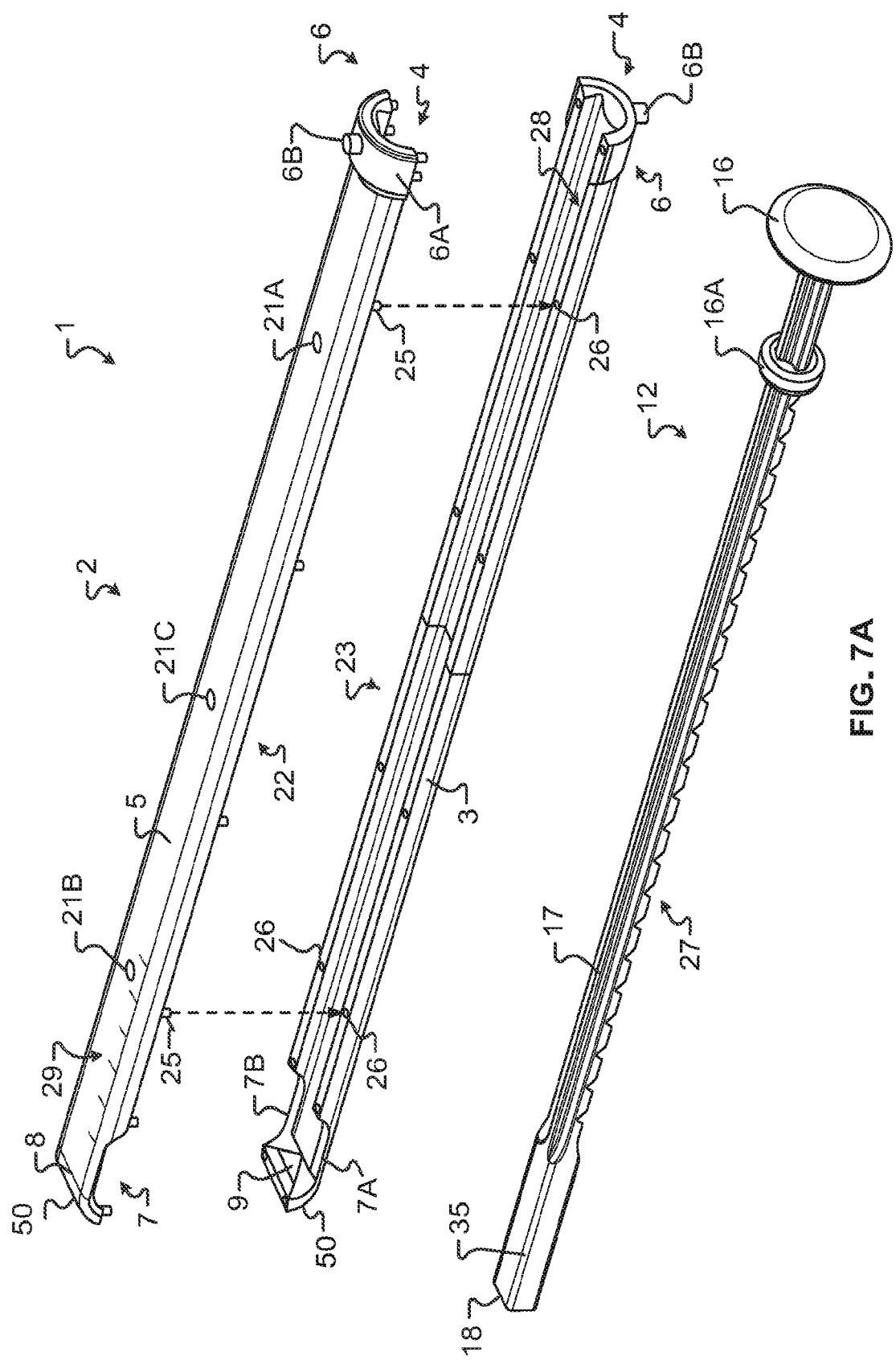
FIG. 7A is a perspective view of a device for delivering bone graft of another embodiment illustrating a hollow tubular member including a plurality of vent ports and a plunger of an embodiment of the present disclosure.

With continued reference to FIG. 7A, the hollow tube 2 is configured to receive the plunger 12 of the present disclosure within the lumen 28. Any plunger 12 of the present disclosure may be used with the hollow tube 2. The plunger 12 is used to push bone graft material positioned in the lumen 28 out of the opening 7 at the distal end 8. In one embodiment, a stop 16A can be formed on the plunger 12 to engage the proximal end 6 of the hollow tube. In this manner, the stop 16A prevents over insertion of the plunger within the lumen.

In various embodiments, the plunger 12 includes a plurality of teeth separated by notches 27. The notches 27 can be engaged by a means for advancing bone graft material, as described herein. In one embodiment, the advancing means comprises a ratchet configured to engage the notches 27. In operation, the ratchet can engage successive notches to advance or withdraw the plunger within the hollow tube 12.

Additionally, or alternatively, the means for advancing can include a gear with teeth. The gear is aligned with the plunger 12 and operable to convert rotational movement of the rear to linear movement of the plunger 12. As the gear rotates, the gear teeth engage the plunger notches 27 to move the plunger toward or away from the hollow tube distal end.

In still another embodiment, the advancing means comprises a worm gear with at least one helical thread. As the worm gear rotates, the helical thread engages the plunger notches 27. In this manner, the worm gear can advance or retract the plunger 12 within the hollow tube 2.

The plunger 12 includes a distal end 18. The distal end 18 substantially conforms to inner walls of the lumen 28. Specifically, in one embodiment, the distal end 18 has a cross-sectional shape which corresponds to the interior shape of the lumen 28. In various embodiments, the plunger distal end 18 is round, ovoid, square, or rectangular. In one embodiment, the distal end 18 is not round. In another embodiment, the distal end 18 of the plunger 12 is configured to contact the inner walls of the lumen 28 about an entire outer periphery of the plunger distal end 18. Additionally, or alternatively, the plunger 12 (or a portion thereof) may be made of rubber silicone to improve the seal with interior surfaces of the lumen 28. In various embodiments, at least the distal end 18 is made of a plastic or an elastomeric rubber.

In one embodiment, the plunger 12 has a length sufficient for the distal end 18 of the plunger 12 to extend beyond the opening 7 as generally illustrated in FIG. 7C. In one embodiment, the handle 16 of the plunger 12 is a planar disk shape, as depicted in FIG. 7C. In another embodiment, handle 16 is not planar. For example, handle 16 can be angled so as to conform to interior of funnel 30 when the plunger 12 is fully inserted into hollow tube 2.

In various embodiments, at least one vent port 21 can be formed through the hollow tube 2 to the lumen 28. The vent port 21 is configured to release air from the interior of the hollow tube 2 as bone graft material is delivered to the distal end 8 for discharge out of the opening 7. As one of skill in the art will appreciate, air trapped within the lumen 28 of the hollow tube 2 between the distal end 8 and bone graft material may increase the amount of axial force required by the plunger 12 to move the bone graft material to the discharge opening 7 or may cause the plunger 12 to jam or bind in the lumen 28. Applying excessive force to the plunger 12 to eject the bone graft material can cause soft tissue inflammation or damage. By allowing air to escape from within the lumen 28 of the hollow tube 2 as the plunger 12 is pressed toward the distal end 8, the vent port 21 may decrease the amount of force required to deliver the bone graft material to the discharge opening 7. The possibility of the plunger 12 jamming within the hollow tube 2 is also reduced. Specifically, the vent port 21 eliminates or reduces the risk of jamming the plunger and also reduces the possibility of trapped air being forced into the disc space and into the patient's vascular system causing an air embolism.

The vent ports 21 also prevent introduction of air or other fluids into the surgical site. For example, air may be introduced into, and trapped within, bone graft material as the bone graft material is loaded into the hollow tube 2. As the plunger 12 is pressed against the bone graft material, the air may be released from the bone graft material. The air can escape from the lumen 28 through the vent ports 21.

Vent ports 21 can be formed through the hollow tubes 2 of all embodiments of the present disclosure. Vent ports 21 may be formed at any location along the length of the hollow tube 2 between the proximal end 6 and the distal end 8. In one embodiment, a vent port 21 is formed on at least one of the first surface 3 and the second surface 5. In one embodiment, vent ports 21 can be formed on more than one surface 3, 5 of the hollow tube.

The at least one vent port 21 is configured to prevent discharge of bone graft material from the lumen 28. Accordingly, the vent port 21 has one or more of a size and a shape selected to prevent passage of bone graft material therethrough. In one embodiment, a width or a diameter of the vent port is less than approximately 2 mm. In one embodiment, the vent port 21 includes a mesh or screen with apertures which allow passage of air therethrough.

As illustrated in FIG. 7B, the vent port 21 can optionally have a generally circular shape, such as a bore. Although the vent port 21 illustrated in FIG. 7B is generally circular, other shapes are contemplated. In one embodiment, the vent port is a slit or slot. The slot may be generally linear. In another embodiment, the vent port 21 has a shape that is generally triangular or rectangular. Specifically, the vent port 21 may have any size or shape which allows the passage of air but prevents passage of bone graft material therethrough.

Any number of vent ports 21 may be formed through the hollow tube 2. In one embodiment, the hollow tube 2 includes at least three vent ports 21. A first vent port 21A can be proximate to the proximal end 6 of the hollow tube 2. A second vent port 21B can be proximate to the distal end 8. A third vent port 21C can be formed between the first and second vent ports 21A, 21B.

In some embodiments, the plunger 12 includes a channel 35 (such as generally illustrated in FIG. 7A) that is configured to release air from the distal end 8 of hollow tube 2 (e.g., the lumen 28) to the proximal end 6 of the hollow tube 2. In this manner, as the plunger 12 is advanced to eject bone graft material from the discharge opening 7, air trapped in the bone graft material and/or the distal end 8 (e.g., the portion of the lumen 28 that is distal to the distal end 18 of the plunger 12) can pass through the channel 35 into the proximal portion of the lumen 28.

In some embodiments, indicia 29 can be formed on one or more surface of the hollow tube 2 (see FIG. 7B). The indicia are configured to indicate a depth of insertion of the distal end 8 of the hollow tube 2 into a surgical site. The indicia 29 can include marking and numerals. In various embodiments, one or more of the indicia 29 is radiopaque. In various embodiments, the indicia 29 extends along the entire length of the hollow tube 2, or along a predetermined portion of the length.

In one embodiment, the hollow tube 2 may comprise a first portion 22 and a second portion 23 which are configured to be interconnected. The hollow tube 2 thus includes a joint 24, illustrated in FIG. 7C, along which the first and second portions 22, 23 are connected. The joint 24 may substantially bisect the hollow tube 2.

The first and second portions 22, 23 can be interconnected by any suitable means. In one preferred embodiment, an ultraviolet activated adhesive is used to interconnect the first and second portions 22, 23. This forms a particularly strong bond in combination with optional alignment features 25, 26 (best seen in FIG. 7E) and the material of the hollow tube 2.

In another embodiment, the first and second portions 22, 23 are sonically welded together. Additionally, or alternatively, one or more glues or adhesives can be used to join the first and second portions 22, 23.

In one embodiment, the first and second portions 22, 23 can include the alignment features 25, 26. In addition to ensuring alignment of the first portion 22 with respect to the second portion 23 when the hollow tube 2 is assembled, the alignment features 25, 26 can also provide support to the hollow tube 2. In one embodiment, the alignment features 25, 26 have a shape selected to increase rigidity of the hollow tube 2, such as to prevent unintended or inadvertent bending or movement.

The alignment features 25, 26 may comprise a projection 25 formed on one of the first and second portions 22, 23 that is at least partially received in a bore or aperture 26 of another of the first and second portions 22, 23. In one embodiment, the alignment feature 25 comprises a peg or pin. In one embodiment, alignment feature 26 comprises a recess configured to receive the peg 25. In one embodiment, one of the alignment features 25, 26 comprises a flange. The flange may extend along some or all of the joint 24. The other one of the alignment features 26, 25 may comprise a groove configured to receive the flange. Similar to the flange, the groove may extend along some or all of the joint 24. Other shapes and features of the alignment features 25, 26 are contemplated.

The alignment features 25, 26 can also be configured to lock the first and second portion 22, 23 together. Specifically, in one embodiment, alignment feature 25 comprises a projection configured to engage a corresponding recess in alignment feature 26. Feature 26 can frictionally engage feature 25.

In various embodiments, the hollow tube 2 is made of a flexible, semi-rigid, or rigid material including, but not limited to, one or more of a plastic, a composite, a metal. In one embodiment, the hollow tube 2 is formed of polycarbonate resin thermoplastic. In one embodiment, at least a portion of the hollow tube 2 is radiopaque. In one embodiment, at least the distal end 8 is radiopaque or includes radiopaque markers, such as indicia 29. In one embodiment, the hollow tube 2 is substantially rigid. In one embodiment, at least a portion of the hollow tube 2 is flexible. For example, in one embodiment, at least about one-half of the hollow tube 2 comprising the distal end 8 is flexible.

In one embodiment, the hollow tube 2 is generally linear. Alternatively, the hollow tube 2 can include a portion that is not linear. More specifically, in one embodiment, the hollow tube 2 can have a permanent (or temporary) curve or bend.

In another embodiment, the proximal end 6 of the hollow tube extends along a first longitudinal axis. At least the distal end 8 of the hollow tube 2 may extend along a second longitudinal axis that is transverse to the first longitudinal axis of the proximal end. The distal end 8 can extend at a predetermined angle from the proximal end 6. In various embodiments, the angle can be between about 0° and about 75°. In one embodiment, the distal end 8 intersects the proximal end 6 at a joint. The joint may be adjustable such that a user can alter the angle between the proximal end 6 and the distal end 8. Alternatively, the joint is not adjustable. The proximal end 6 and the distal end 8 may each extend generally linearly to the joint. Alternatively, the hollow tube 2 may include a transition portion between the proximal end 6 and the distal end 8. The transition portion can have a shape that is curved, such as an elbow joint.

In one embodiment, the hollow tube 2 is made of a substantially transparent or translucent material, and the hollow tube 2 is not opaque. In one embodiment, at least a portion of the hollow tube 2 is transparent or translucent. In one embodiment, the hollow tube 2 includes windows of a transparent or translucent material. Accordingly, in some embodiments, the plunger 12 is at least partially visible within the lumen 28 of the hollow tube.

Referring now to FIG. 7D, in various embodiments, the hollow tube 2 includes one or more image sensing devices 36. In various embodiments, the image sensing device(s) 36 includes, without limitation, one or more of an endoscope, a camera and/or an image sensor that is/are operably coupled to the hollow tube 2. Other types of image sensing devices known to one skilled in the art are also contemplated. In various embodiments, the image sensing device(s) 36 is removably or permanently coupled to the hollow tube 2. In one embodiment, the image sensing device(s) 36 extends through a portion of the hollow tube 2 (see FIG. 7G). In another embodiment, the image sensing device 36 is interconnected to an exterior surface (i.e., side surface 3 and/or top/bottom surface 5) of the hollow tube 2. Additionally, or alternatively, the image sensing device 36 extends within at least a portion of the lumen 28. In various alternate embodiments, the image sensing device(s) 36 is positioned on the plunger 12.

In one embodiment, the image sensing device(s) 36 is oriented to view at least the distal end 8 of the hollow tube 2. Optionally, the image sensing device(s) 36 is repositionable with respect to the distal end 8. In this manner, the image sensing device 36 can be manipulated to view one or more openings 7 of the hollow tube 2, or view the internal aspect of the disc space 172A (see FIG. 7G), or a debrided portion of the disc space 172A, prior to administration of bone graft.

In another embodiment, the hollow tube 2 can include one or more lighting elements 37 (see FIG. 7D). In various embodiments, the lighting element(s) 37 is operably associated with the image sensing device 36. Additionally, or alternatively, one or more lighting elements 37 can be fixed to, or integrally formed with, the hollow tube 2. Suitable lighting elements, cameras, and displays that may be used with the integrated fusion cage and graft delivery device 1 of the present disclosure are described in U.S. Pat. Nos. 8,864,654, 9,717,403, and PCT Pub. WO 2012/145048, which are each incorporated herein by reference in their entirety. Other types of lighting elements known to one skilled in the art are also contemplated As illustrated in FIGS. 7B and 7C, the funnel 30 can be releasably interconnected to the hollow tube 2. The funnel 30 facilitates loading of bone graft material into the opening 4 at the proximal end 6 of the hollow tube 2. Once the lumen 28 is loaded with bone graft material, the funnel may be removed to improve visualization of the distal end 8 and opening 7 in a surgical site, such as a disc space. In contrast to prior devices which include a fixed funnel which cannot be removed, the releasable funnel 30 of the present disclosure does not obstruct visualizing the distal end 8 of the hollow tube 2 as it is placed in a disc space or other surgical site. In one embodiment, if additional bone graft material is required, the funnel 30 is interconnected to the hollow tube 2 during the surgical procedure without having to remove the hollow tube 2 from the surgical site, decreasing the potential trauma to adjacent nerve tissue.

The funnel 30 is releasably interconnected to the hollow tube 2. In one embodiment, the funnel 30 is retained on the hollow tube 2 by a friction fit. Alternatively, the funnel 30 can snap onto the hollow tube. In one embodiment, the hollow tube 2 includes a collar 6A with one or more projection 6B (see FIG. 7B), and the funnel 30 has a sleeve 32 that fits over the collar 6A and engages the projection 6B. In one embodiment, the sleeve 32 includes a slot 33 to engage the projection 6B. The slot 33 and projection 6B form a bayonet mount in one embodiment. Other connection mechanisms are contemplated, as known in the art.

In various embodiments, the hollow tube 2 is configured to receive a fusion cage 60 of one or more of the embodiments described herein. In one embodiment, the fusion cage 60 has a fixed height. Alternatively, the fusion cage 60 is expandable after placement in a disc space.

In one embodiment, the fusion cage 60 includes an opening 65 to discharge bone graft material therethrough (see FIG. 7C). The opening 65 is alignable with the opening 7 of the hollow tube 2. In one embodiment, the fusion cage 60 includes two or more openings 65 which each correspond to openings 7A, 7B of the hollow tube 2. Accordingly, as bone graft material is advanced through the lumen 28 and through the opening 7 of the hollow tube 2, the bone graft material will be discharged through opening(s) 65 of the fusion cage 60 into a surgical site, such as a disc space.

In one embodiment, a distal end 64 of the fusion cage 60 is closed. The distal end 64 may have a blunt or tapered shape similar to the wedge-shaped end 50 of the hollow tube 2.

In one embodiment of the device 1, the width of the hollow tube 2's first, exterior side surfaces 3 is between 5 and 11 mm. In another embodiment, the width of these exterior side surfaces 3 is between 7 and 9 mm. In another embodiment, the width of these exterior side surfaces 3 is between 7.5 mm and 8.5 mm. In yet another embodiment, the width of these exterior side surfaces 3 is 8 mm. In one embodiment of the device 1, the width of the hollow tube 2's second, exterior top and bottom surfaces 5 is between 9 and 15 mm. In a preferred embodiment, the width of these exterior top and bottom surfaces 5 is between 11 and 13 mm. In another embodiment, the width of these exterior top and bottom surfaces 5 is between 11.5 mm and 12.5 mm. In yet another embodiment, the width of these exterior top and bottom surfaces 5 is 12 mm.

In one embodiment of the device, the ratio of the width of the hollow tube 2's second, exterior top and bottom surfaces 5 to the width of the hollow tube 2's first, exterior side surfaces 3 is between approximately 1.7 and 1.3. In another embodiment, this ratio is between 1.6 and 1.4. In still another embodiment, this ratio is between 1.55 and 1.45. In another embodiment, this ratio is 1.5.

In one embodiment of the device 1, a first interior width of the hollow tube 2 along a minor axis between the two first, side exterior surfaces 3) is between 5 and 9 mm. In another embodiment, the first interior width is between 6 and 8 mm. In yet another embodiment, the first interior width is between 6.5 mm and 7.5 mm. In still another embodiment, the first interior width is 7 mm. In one embodiment of the device 1, a second interior width of the hollow tube 2 along a major axis between the second exterior top and bottom surfaces 5 is between 9 and 13 mm. In another embodiment, the second interior width is between 10 and 12 mm. In yet another embodiment, the second interior width is between 10.5 mm and 11.5 mm. In still another embodiment, the second interior width is 11 mm.

In one embodiment of the device 1, the ratio of the second interior width to the first interior width is between approximately 1.7 and 1.3. In another embodiment, this ratio is between 1.6 and 1.4. In another embodiment, this ratio is between 1.55 and 1.45. In yet another embodiment, this ratio is 1.5.

In one embodiment, one or more edges of the device 1 are rounded. For example, exterior edges of the hollow tube 2 are rounded, and/or interior edges of the hollow tube 2 are rounded. In this embodiment, edges of the plunger 12 (at least at the plunger's distal end 18), are identically rounded to ensure a congruous or conformal fit between edges of the plunger 12 and the interior of the hollow tube 2 so as to, among other things, urge the majority of bone graft material to move through the hollow tube 2.

In various embodiments, the device 1 is formed using a three-dimensional printing process. More specifically, one or more of the hollow tube 2, the plunger 12, the funnel 30, and/or the fusion cage 60 are manufactured by one or more three-dimensional printing processes. A variety of materials, including metals, PEEK, other plastics and/or combinations of such materials, are used in a three-dimensional printer to form the device 1 in various embodiments.

Referring now to FIG. 7F, devices 42A and 42B for preparing a bone graft material 44 according to one embodiment of the present disclosure are illustrated. Specifically, in one embodiment, bone graft material 44 is prepared within one or more devices 42, such as, for example, graduated syringes. The bone graft material 44 is compressed or compacted to form a desired and measured amount of bone graft material. In various embodiments, the bone graft material 44 comprises two components, such as, for example an activating agent or a liquid 44A and a dry material or a granular material 44B. The bone graft material components 44A, 44B include other substances in other embodiments. In various other embodiments, the bone graft material 44 includes more than two components, for example, three, four, five or ten components.

Referring again to FIG. 7F, the bone graft components 44A, 44B are mixed together by interconnecting the devices 42A, 42B. In one embodiment, the devices 42A, 42B are interconnected with a bayonet mount. In one embodiment, a connecting device 46 is provided to interconnect device 42B to device 42A. Connecting device 46 may include luer locks. The luer locks may include a locking or slip style connector. A bore 48 through the connecting device 46 enables bone graft material components 44A and/or 44B to be injected from one syringe 42A/42B to the other syringe 42B/42A. In one embodiment, component 44B is injected from device 42B into device 42A to be mixed with bone graft component 44A.

Once mixed, the bone graft material 44 (i.e., mixed components 44A, 44B) are subsequently be discharged from device 42A into the hollow tube 2. In one embodiment, the device 42A can be interconnected to the proximal end 6 of the hollow tube 2. Additionally, or alternatively, the bone graft material 44 can be ejected from the device 42A into the funnel 30. Suitable devices 42 that can be used to prepare bone graft material for use with the integrated fusion cage and graft deliver device 1 of the present disclosure are known and described in U.S. Pat. Pub. 2009/0124980, U.S. Pat. Pub. 2014/0088712, U.S. Pat. Pub. 2014/0276581, U.S. Pat. Pub. 2014/0371721, U.S. Pat. Nos. 8,439,929, and 9,174,147 which are each incorporated herein by reference in their entirety.

The integrated fusion cage 60 and graft delivery device 1 of the present invention provides many benefits over other devices. For example, the rectangular lumen 28 of embodiments of the hollow tube 2 affords several advantages over conventional circular configurations. For a surgical area with a smallest dimension set at a width of 8 mm and a thickness dimension 0.5 mm, a conventional circular device (with resulting interior diameter of 7 mm or a radius of 3.5 mm) would realize a surface area of 38.48 $mm^2$. In contrast, the device of the present invention would carry interior dimensions of 7 mm by 11 mm for a surface area of 77 mm, an increased surface area factor of nearly 2.0, thereby resulting in more bone graft material delivery. This is at least in because, among other things, a given volume of bone graft encounters less surface area of the interior of a larger device which results in, among other things, a reduced likelihood of bone graft material becoming jammed within the device.

Referring now to FIG. 8, a conventional prior art bone graft delivery device 170 provided in combination with a surgical work site 172 is illustrated. Specifically, a bone graft delivery device 170 is shown as providing a bone graft material 44 to an intervertebral space 172 within a human spine. The tool 170 is generally inserted into a patient from a transforaminal or lateral access site, and a second end of the delivery device 170 is provided within the intervertebral space to which bone graft material 44 is to be provided. The device 170 includes a conventional end-dispensing lumen 170a that ejects and injects the bone graft material 44 directly into the intended path of a fusion cage. The device and method of FIG. 8 does not distribute bone graft delivery material into the periphery of the prepared disc space and generally fails to achieve appropriate distribution of bone graft delivery material within the disc space 172. Additionally, the small diameter tube necessitates injecting the bone graft material 44 in a more liquid (less viscous) state. In some cases, the pressure required to push bone graft material through the bore of device 170 is relatively high, increasing the risk of the device jamming. Generally, the risk of injury to the patient increases as the pressure required to eject the bone graft material from the delivery device 170 increases. Furthermore, if the device jams, then it needs to be removed, increasing the cumulative trauma to the surrounding nerve tissue as the device is removed and reinserted.

Figure 9B:
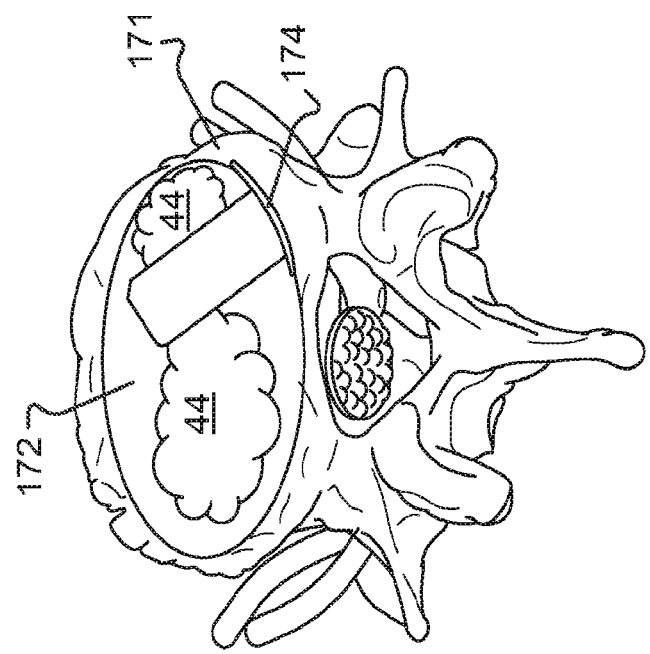
FIG. 9B is another environmental view of the surgical site of FIG. 9A after the bone graft delivery device has been removed therefrom.
Figure 9A:
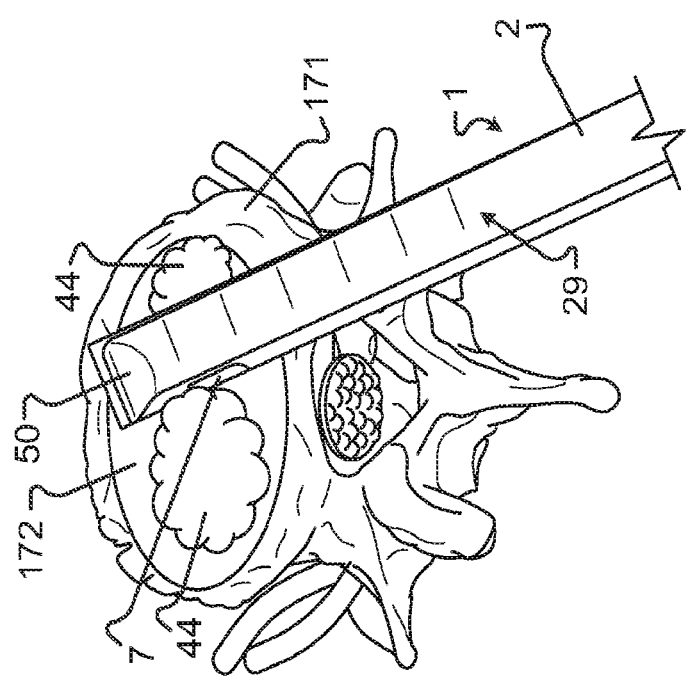
FIG. 9A is an environmental view of a surgical site and a bone graft delivery device according to one embodiment of the present disclosure.

Referring now to FIG. 9A, an integrated fusion cage and graft delivery device 1 according to embodiments of the present disclosure is illustrated delivering bone graft material 44 to a disc space 172 within a patient's spine 171. As shown, the hollow tube 2 of the device 1 is provided with at least one side opening 7. Bone graft material 44 is provided to the intervertebral space 172 by ejecting the material from the side opening 7. In some embodiments, the hollow tube 2 has two side openings 7 such that bone graft material 44 is ejected on opposing sides of the device 1. In this manner, the device 1 provides enhanced distribution of bone graft material 44 and a greater quantity of bone graft material into a surgical site compared to the device 170 described in conjunction with FIG. 8. Further, the larger cross-sectional shape of the hollow tube 2 of the delivery device 1 of the present invention allows injection of bone graft material in a thicker, more controllable viscous state and with less force than required by the device 170.

An additional benefit of some embodiments of the graft delivery device 1 of the present disclosure is that they avoid injection of bone graft material 44 directly into the path or intended path of a cage, such as done by the device 170 illustrated in FIG. 8. For example, FIG. 9B provides a top view of the surgical workspace 172 according to FIG. 9A, after the integrated fusion cage and graft delivery device 1 has been removed after insertion or injection of the bone graft material 44. As shown in FIG. 9B, removal of the bone graft delivery device 1 provides an unobstructed path 174 and void space for subsequent insertion of a fusion cage (not shown in FIG. 9B). In this manner, the graft delivery device 1 of the present disclosure provides for a sufficient amount of bone graft material 44 within the surgical site 172 and provides an area 174 that is operable to receive a fusion cage.

In various embodiments, the graft delivery device 1 of the present disclosure is used in the surgical treatment of a collapsed/injured vertebra. For example, in one embodiment, a surgeon introduces the graft delivery device 1 (e.g., the hollow tube 2 thereof) into a collapsed/injured vertebra to create a cavity in the vertebra. The surgeon then fills the cavity with bone cement, to repair the collapsed/injured vertebra.

In one embodiment of the foregoing surgical technique, the surgeon uses a pedicle screw to create an opening that functions as an opening or pathway to the collapsed/injured vertebral body, and then removes the pedicle screw. The surgeon then inserts the hollow tube 2 of the graft delivery device 1 through the opening/passageway created by the pedicle screw. In various other embodiments, a surgeon may make and use any or all other commonly known surgical pathways to the interior of a collapsed/injured vertebrae, including, but not limited to, an anterior approach and a lateral approach.

In other embodiments, the fusion cage may be inserted into the collapsed vertebra, filled with bone cement and/or other materials, and left in place.

Referring now to FIGS. 10-17, another embodiment of a graft delivery device 1 of the present disclosure is generally illustrated. The graft delivery device 1 includes features that are the same as or similar to other graft delivery devices described herein, including those described in conjunction with FIGS. 1-9. Notably, the graft delivery device 1 generally includes a cannular or hollow tube 2, a plunger 12, and a detachable funnel 30.

The hollow tube 2 is the same as, or similar to, other embodiments of hollow tubes of the present disclosure. Accordingly, the hollow tube 2 generally includes an opening 4 at a proximal end 6. The opening 4 provides access to a substantially hollow interior formed between the proximal end 6 and the distal end 8. The hollow interior defines a lumen 28 that extends through the hollow tube 2.

The lumen 28 has a predetermined cross-sectional shape. In various embodiments, the cross-sectional shape of the lumen 28 is round, ovoid, square, or rectangular. In another embodiment, the interior of the lumen 28 is not round and is, for example, rectangular. In one embodiment the cross-sectional shape of the lumen 28 is substantially uniform along the length of the hollow tube 2. In one embodiment, the lumen 28 has a uniform cross-sectional size along its length. In various embodiments, the exterior of the hollow tube 2 has a shape that is one of round, ovoid, square, and rectangular. In one embodiment, the distal end 8 of the hollow tube 2 is rounded or smooth. The distal end can have a wedge-shape. At least one discharge opening 7 is formed in the distal end 8 of the hollow tube 2. In one embodiment, the discharge opening 7 is positioned transverse to a longitudinal axis of the hollow tube 2. More specifically, in one embodiment the discharge opening 7 can be formed in a first side surface 3A proximate to the distal end 8. Optionally, the opening 7 can extend to top and bottom surfaces 5A, 5B of the hollow tube 2 as generally illustrated in FIGS. 11-12. As shown in FIGS. 11 and 12, because the opening 7 of one embodiment extends to the top and bottom surfaces 5A, 5B the distal end 8 can have a width 70B that is less than a width 70A of a proximal portion of the hollow tube 2.

Expanding the opening 7 in this manner facilitates the movement of bone graft material laterally out of the hollow tube 2. More specifically, by extending the opening 7 in the inferior and superior directions to the top and bottom surfaces 5A, 5B, the size of the opening 7 is increased. This feature minimizes the amount of horizontal travel (or turning) of bone graft as it moves from the lumen 28 and is discharged out of the opening 7. Further bone graft material flowing in the lumen 28 to the opening 7 does not have to change direction or move vertically around an edge of the opening 7 such as would occur if the opening 7 were only formed in the first side 3A. For example, the opening 7 of the embodiment generally illustrated in FIGS. 11-12 does not include any obstructions formed by portions of the first side 3A extending inwardly from at least one of the top surface 5A and/or the bottom surface 5B. In one embodiment, the first side 3A of the hollow tube 2 ends at the proximal portion of the opening 7. Because of this, the opening 7 extends the entire height of the lumen 28 from the top surface 5A to the bottom surface 5B. Accordingly, there are no obstructions extending from the top and bottom surfaces 5A, 5B around which the bone graft material must flow or against which the bone graft material could become compacted or compressed such as to impede the flow of bone graft material from the opening. The applicant has found that in this manner, less dense bone graft material, such as bone graft that has a fibrous composition similar to the consistency of a cotton ball, can be discharged laterally out of opening 7. In contrast, some prior art bone graft delivery devices cannot be used to discharge fibrous bone graft laterally because the fibrous bone graft will compact and does not move out of the prior art delivery devices. Additionally, the fibrous bone graft can catch on edges of openings of some prior art delivery devices.

The hollow tube 2 is configured to receive the plunger 12 of the present disclosure within the lumen 28. The plunger 12 can be used to push bone graft material positioned in the lumen 28 out of the opening 7 at the distal end 8. Optionally, a stop 16A can be formed on the plunger 12 to engage the proximal end 6 of the hollow tube. In this manner, the stop 16A prevents over insertion of the plunger within the lumen.

The plunger 12 is generally configured to substantially conform to inner walls of the lumen 28. Specifically, in one embodiment, at least a portion of plunger 12 has a cross-sectional shape which generally corresponds to the interior shape of the lumen 28. In various embodiments, the plunger 12 has a cross section that is round, ovoid, square, or rectangular. In one embodiment, a cross section of the plunger 12 is not round. In another embodiment, at least a portion of the plunger 12 is configured to contact the inner walls of the lumen 28 about an entire outer periphery of the plunger 12.

The plunger 12 includes a distal end 18. The distal end 18 can include one or more blunt surfaces 74. In one embodiment, the blunt surfaces 74 are generally planar at least before the distal end 18 contacts a curved surface 10 of the hollow tube 2. In one embodiment, the blunt surfaces 74 can be angled transverse to the longitudinal axis of the plunger 12. For example, in one embodiment, one or more of the blunt surfaces 74 are oriented at an angle of between approximately 30° and 60° relative to the longitudinal axis of the plunger 12. In one embodiment, and referring now to FIG. 15, the distal end 18 can include a first blunt surface 74A and a second blunt surface 74B. In one embodiment, the first blunt surface 74A has a greater surface area than the second blunt surface 74B. Additionally, or alternatively, the first blunt surface 74A can be oriented toward the opening 7 of the hollow tube 2. In one embodiment, the blunt surfaces 74 can be substantially orthogonally arranged to one other.

Figure 14:
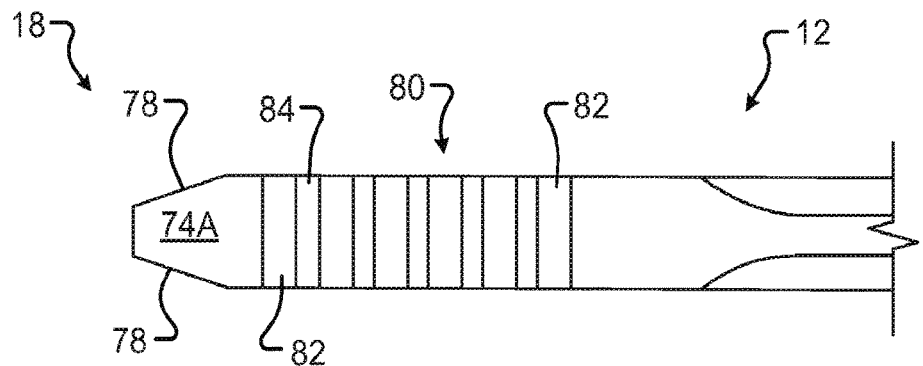
FIG. 14 is a side elevation view of the distal portion of the plunger.
Figure 17:
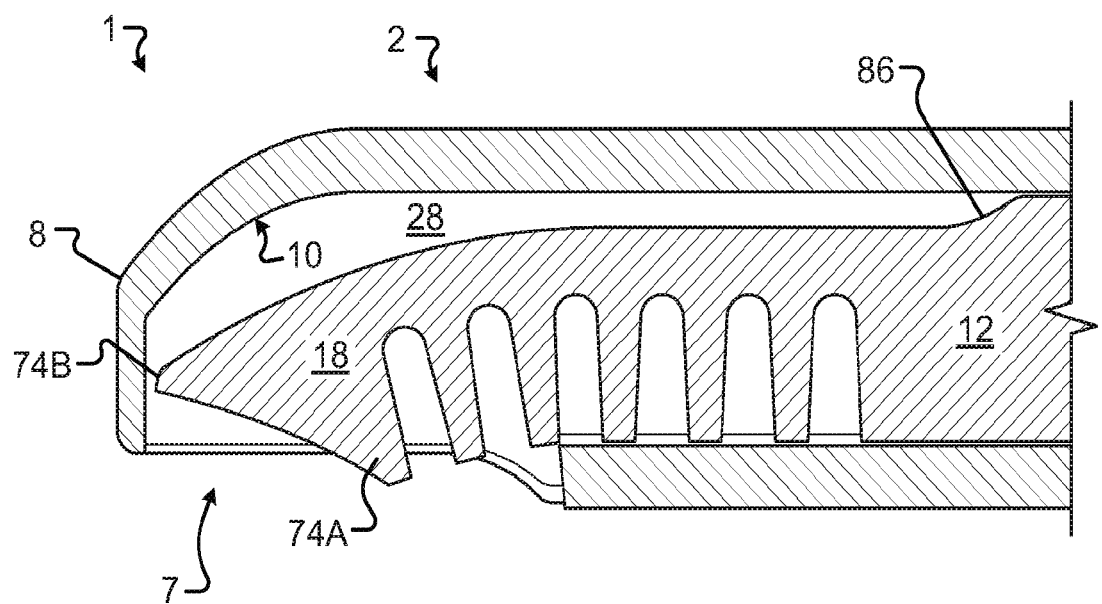
FIG. 17 is another cross-section view of the distal portion of the graft delivery device illustrating the distal end of the plunger in a second state after bending transverse to the longitudinal axis.

Referring now to FIG. 14, opposing surfaces 78 of the distal end 18 can be tapered to be rounded or bullet-shaped. In one embodiment, the opposing surfaces 78 are substantially symmetric. The opposing surfaces 78 facilitate movement of bone graft material out of the lumen 28 of the hollow tube 2. Additionally, the opposing surfaces 78 allow the distal end 18 to move at least partially out of the opening 7 of the hollow tube 2, as generally illustrated in FIG. 17 during bone graft delivery to a surgical site.

In one embodiment, the distal end 18 of the plunger 12 (or a portion of the plunger 12) can be adapted to bend or flex as the plunger 12 is advanced proximate to the distal end 8 of the hollow tube 2. More specifically, in one embodiment, the plunger distal end 18 is configured to bend relative to a longitudinal axis of the plunger 12, as generally illustrated in FIG. 17. In this manner, the distal end 18 of the plunger is configured to push substantially all of the bone graft out of the opening 7 of the hollow tube 2.

Figure 16:
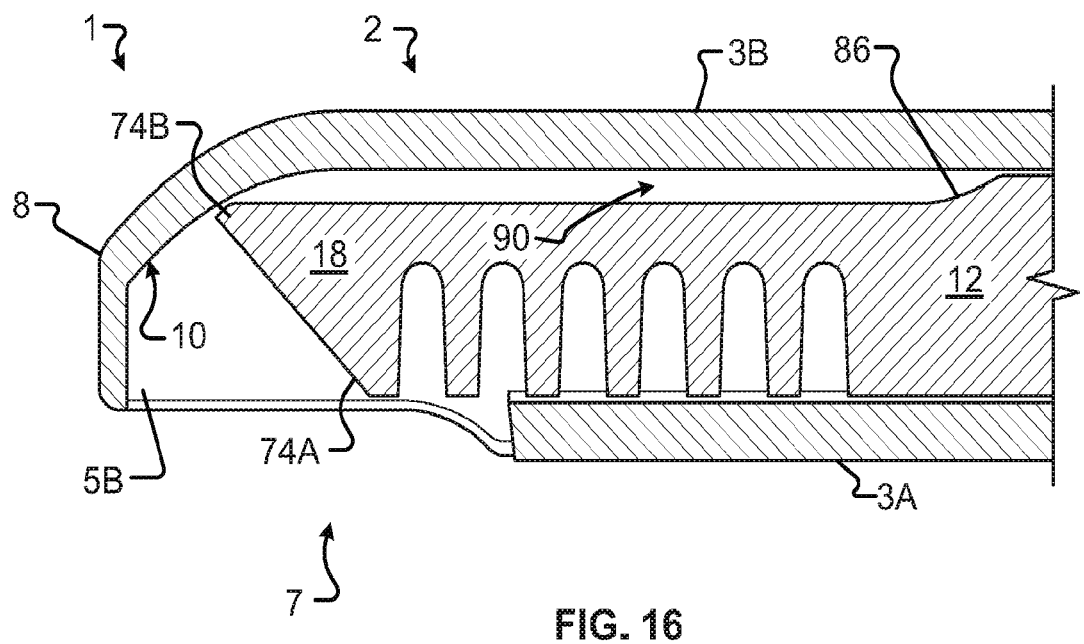
FIG. 16 is a cross-sectional view of a distal portion of the graft delivery device of FIG. 10 illustrating the distal end of the plunger in a first state generally parallel to a longitudinal axis of the plunger.

In one embodiment, the plunger's distal end 18 is configured to bend in response to contact with an interior surface of the hollow tube 2. For example, the hollow tube 2 can have a geometry configured to bend at least the distal end 18 of the plunger 12 toward the opening 7 of the hollow tube 2. In one embodiment, the hollow tube 2 includes a curved surface 10. The curved surface 10 is configured to deflect or bend the plunger distal end 18 from an alignment generally parallel to a longitudinal axis of the plunger 18 (as generally illustrated in FIG. 16) to a bent position generally transverse to the longitudinal axis and toward the opening 7 (as generally illustrated in FIG. 17). The blunt surface 74 of the plunger 12 is configured to advance along the curved surface 10 without catching or sticking. In one embodiment, the second blunt surface 74B is configured to contact the curved surface 10. Accordingly, the second blunt surface 74B can be oriented to slide along the curved surface 10. Additionally, or alternatively, the first blunt surface 74A may not contact the curved surface 10. In contrast, a plunger 12 with a distal end 18 perpendicular to the plunger 12's longitudinal axis would be expected to bind or catch on the curved surface 10 and prevent efficient discharge of bone graft from the hollow tube 2.

The curved surface 10 can be similar to a ramp or arch. Optionally, the curved surface 10 includes surfaces generally opposite the opening 7. More specifically, the curved surface can be formed on side of the lumen longitudinal axis opposite to the opening 7. In one embodiment, the curved surface 10 has a length generally parallel to the longitudinal axis of the hollow tube 2 that is approximately one-half of the maximum length of the opening 7 parallel to the longitudinal axis.

The curved surface 10 is configured to interface with the distal end 18 of the plunger 12 to alter the path of the plunger distal end. Additionally, the curved surface 10 can direct the bone graft material away from the opening 7 into a surgical site, such as a disc space. More specifically, the curved surface 10 can be configured to function as a reverse funnel to disperse bone graft material ejected from the opening 7 as generally illustrated in FIG. 9A.

In various embodiments, the plunger 12 is made of a flexible material, including, but not limited to. a rubber, an elastomeric material, other suitable flexible materials and/or a combination of such materials. The distal end 18 can be made of a material different than the rest of the plunger 12. In one embodiment at least the distal end 18 of the plunger 18 is made of the flexible material.

Figure 13:
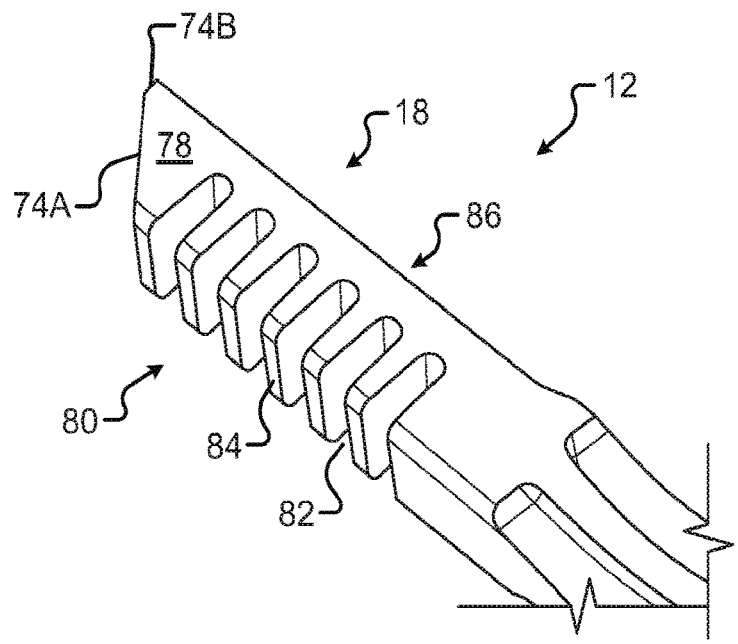
FIG. 13 is a perspective view of a distal portion of a plunger of the graft delivery device of FIG. 10.
Figure 15:
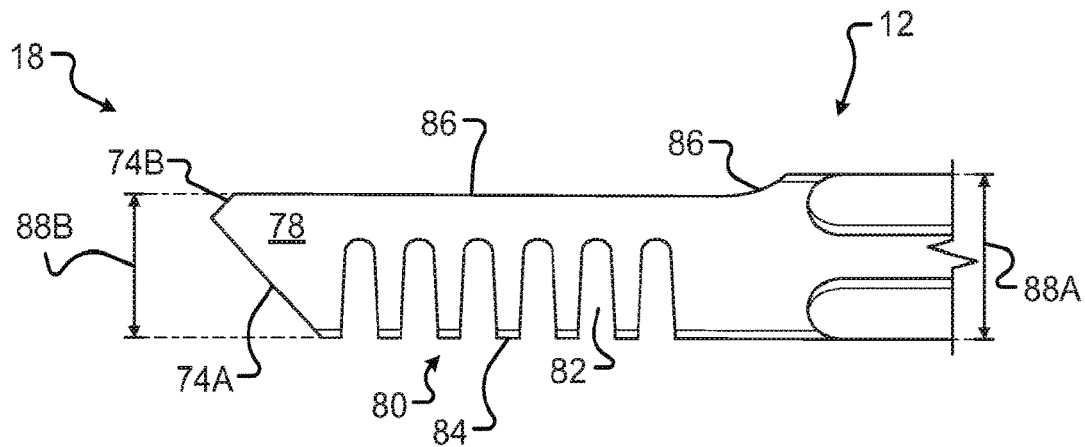
FIG. 15 is a top plan view of the distal portion of the plunger.

In various embodiments, the plunger distal end 18 has an area of flexibility 80 (see FIGS. 13-15). The area of flexibility 80 is configured to cause at least the distal end 18 to bend in a predetermined direction toward the opening 7. In one embodiment, the area of flexibility 80 comprises one or more relief areas 82 formed in the distal end 18. In one embodiment, the relief areas comprise notches 82. In one embodiment, the notches 82 are formed transverse to a longitudinal axis of the plunger 12. In one embodiment, the notches 82 are positioned to face the opening 7 when the plunger 12 is positioned within the hollow tube 2. Alternatively, the notches 82 can be oriented to face away from the opening 7.

In various embodiments, the notches 82 are formed such that walls between adjacent notches have outer ends 84 that are generally planar. In one embodiment, the notches 82 extend at least approximately halfway through the width 88 of the plunger. In one embodiment, the notches 82 are spaced substantially evenly along the distal end 18. In one embodiment, the notches 82 have a generally uniform size and shape. In an alternate embodiment, the notches 82 have different sizes and/or shapes.

In one embodiment, the area of flexibility 80 is back cut to decrease the width 88B of the plunger distal end 18. In one embodiment, the distal end 18 is back cut to form a rabbet 86. In another embodiment, the rabbet 86 is formed on a side of the plunger 12 that is opposite to the relief areas.

In one embodiment, the rabbet 86 extends generally parallel to a longitudinal axis of the plunger 12. Accordingly, in one embodiment, the distal end 18 can have a width 88B that is less than a width 88A of another portion of the plunger 12, as generally illustrated in FIG. 15. The rabbet 86 has a depth selected to form a gap 90 between the distal end 18 and an interior of the lumen 28 such as shown in FIG. 16. In one embodiment, the gap 90 beneficially prevents the plunger distal end 18 from contacting and binding against the interior of the lumen 28 as the distal end 18 bends toward the opening. For example, when the plunger 18 contacts the curved surface 10 of the hollow tube 2, the plunger 12 may buckle or bulge. The gap 90 provides clearance between the plunger 12 and the hollow tube 2 if the plunger 12 buckles.

In various embodiments, the plunger 12 can include a plurality of teeth and notches that are the same as, or similar to, the teeth and notches 27 of the plunger described in conjunction with FIG. 7A. The notches can be engaged by a means for advancing bone graft material described herein. In this manner, the advancing means can move the plunger 12 relative to the hollow tube 2. In various embodiments, the advancing means includes a ratchet, a gear, a worm gear with a helical thread and the like such as described herein.

In one embodiment, the funnel 30 is releasably interconnected to a proximal end 6 of the hollow tube 2 to facilitate loading of bone graft material into the opening 4. Thereafter, the funnel 30 is removed to improve visualization of the distal end 8 and opening 7 in a surgical site. The funnel 30 can be the same as other funnels 30 described herein.

In one embodiment, the graft delivery device 1 includes at least one vent port to release air from the lumen 28 as bone graft material is advanced to the distal end 8 for discharge out of the opening 7. Although the vent port is not illustrated in FIGS. 10-17 for clarity, the vent port can be as the same as described in other embodiments of the graft delivery device described herein. For example, the vent ports 21 described in conjunction with FIG. 7A can be used with the graft delivery device 1 illustrated in FIGS. 10-17.

In some embodiments, indicia is formed on one or more surface of the hollow tube 2. The indicia can be the same as or similar to the indicia 29 described in conjunction with FIG. 7. The indicia are configured to indicate a depth of insertion of the distal end 8 of the hollow tube 2 into a surgical site. The indicia can include markings and numerals. In various embodiments, one or more of the indicia is radiopaque. In various embodiments, the indicia extends along the entire length of the hollow tube 2, or along a predetermined portion of the length.

In one embodiment, the hollow tube 2 can receive a fusion cage 60 of an embodiment of the present invention. The fusion cage 60 can have a fixed height or be expandable after placement in a disc space. The fusion cage 60 can have an opening 65 to discharge bone graft material therethrough. The opening 65 can be alignable with the opening 7 of the hollow tube 2. The fusion cage 65 can have a distal end 64 that is blunt, tapered, or wedge shaped. The hollow tube 2 can be configured to interconnect to other fusion cages.

In various embodiments, the hollow tube 2 is made of a flexible, semi-rigid, or rigid material including, but not limited to, one or more of a plastic, a composite, a metal. In one embodiment, the hollow tube 2 is formed of polycarbonate resin thermoplastic. In one embodiment, at least a portion of the hollow tube 2 is radiopaque. In one embodiment, at least the distal end 8 is radiopaque or includes radiopaque markers, such as indicia 29 describe herein. In one embodiment, the hollow tube 2 is substantially rigid. In one embodiment, at least a portion of the hollow tube 2 is flexible. For example, in one embodiment, at least about one-half of the hollow tube 2 comprising the distal end 8 is flexible. In one embodiment, the hollow tube 2 is generally linear.

In one embodiment, the hollow tube 2 is made of a substantially transparent or translucent material, and the hollow tube is not opaque. In one embodiment, at least a portion of the hollow tube 2 is transparent or translucent. In one embodiment, the hollow tube 2 includes windows of a transparent or translucent material. Accordingly, in some embodiments, the plunger 12 is at least partially visible within the lumen 28 of the hollow tube 2. In various embodiments, the hollow tube 2 includes one or more image sensing device(s), such as an endoscope, camera, and/or an image sensor. The image sensing device(s) can be the same as or similar to the image sensing device(s) 36 described in conjunction with FIG. 7D. In various embodiments, the image sensing device(s) is removably or permanently coupled to the hollow tube 2. In one embodiment, the image sensing device(s) is oriented to view at least the distal end 8 of the hollow tube 2. Additionally, or alternatively, the image sensing device(s) is configured to view an internal aspect of a disc space 172A. Embodiments of the graft delivery device 1 illustrated in FIGS. 10-17 can also be used by a surgeon to repair a collapsed/injured vertebrae, in the same ways as discussed above in connection with the graft delivery device of FIGS. 1-7G. Referring now to FIGS. 18-25, a graft delivery device 1 of another embodiment of the present disclosure is generally illustrated. The graft delivery device 1 includes features that are the same as or similar to other graft delivery devices described herein including those described in conjunction with FIGS. 1-7G, 9A, 9B and 10-17. Notably, the graft delivery device generally includes a cannular or hollow tube 2, a plunger 12, and a detachable funnel 30.

The hollow tube 2 is the same as, or similar to, other embodiments of hollow tubes of the present disclosure. Accordingly, the hollow tube 2 generally includes an opening 4 at a proximal end 6. The opening 4 provides access to a substantially hollow interior formed between the proximal end 6 and the distal end 8. The hollow interior defines a lumen 28 that extends through the hollow tube 2.

The lumen 28 has a predetermined cross-sectional shape. In various embodiments, the cross-sectional shape of the lumen is round, ovoid, square, or rectangular. In another embodiment, the interior of the lumen is not round and is, for example, rectangular. In one embodiment the cross-sectional shape of the lumen 28 is substantially uniform along the length of the hollow tube 2. In one embodiment, the lumen 28 has a uniform cross-sectional size along its length. In various embodiments, the exterior of the hollow tube 2 has a shape that is one of round, ovoid, square, and rectangular.

In various embodiments, the distal end 8 of the hollow tube 2 is rounded or smooth. In one embodiment, the distal end has a wedge-shape.

In various embodiments, two discharge openings 7 are formed in the distal end 8 of the hollow tube 2. In one embodiment, the discharge openings 7 are positioned transverse to a longitudinal axis of the hollow tube 2. More specifically, in one embodiment a first discharge opening 7A can be formed in a first side 3A of the hollow tube 2 and a second discharge opening 7B can be formed in a second side 3B. In one embodiment, the openings 7 can extend to top and bottom surfaces 5A, 5B of the hollow tube 2 as generally illustrated in FIGS. 19-20. In one embodiment, generally illustrated in FIG. 20, the sides 3A, 3B of the hollow tube 2 do not extend past a proximal portion of the openings 7A, 7B. As shown in FIG. 20, because the openings 7A, 7B of one embodiment extend to the top and bottom surfaces 5A, 5B, the distal end 8 can have a width 70B that is less than a width 70A of a proximal portion of the hollow tube 2.

Forming the openings 7A, 7B in this manner can facilitate the movement of bone graft material laterally out of the hollow tube 2. More specifically, by extending the openings in the inferior and superior directions to the top and bottom surfaces 5A, 5B, the size of each of the openings 7A, 7B is increased. This feature minimizes the amount of horizontal travel (or turning) of bone graft as it moves from the lumen 28 and is discharged out of the openings 7A, 7B. Further, bone graft material flowing in the lumen 28 to the openings 7A, 7B does not have to change direction or move vertically around an edge of the openings, such as would occur if the openings were only formed in the first and second sides 3A, 3B. For example, the openings 7A, 7B of the embodiment generally illustrated in FIGS. 19-20 does not include any obstructions formed by portions of the first or second sides 3A, 3B extending inwardly from at least one of the top surface 5A and the bottom surface 5B. Because of this, one or more of the openings 7A, 7B can extend the entire height of lumen 28 from the top surface 5A to the bottom surface 5B. Accordingly, there are no obstructions extending from the top and bottom surfaces 5A, 5B around which the bone graft material must flow or against which the bone graft material could become compacted or compressed thereby impeding the flow of bone graft material from the openings 7A, 7B.

The applicant has found that in this manner, less dense bone graft material, such as bone graft that has a fibrous composition similar to the consistency of a cotton ball, can be discharged laterally out of the openings 7A, 7B. In contrast, some prior art bone graft delivery devices cannot be used to discharge fibrous bone graft laterally because the fibrous bone graft will compact and does not move out of the prior art delivery devices. Additionally, the fibrous bone graft can catch on edges of openings of some prior art delivery devices.

The hollow tube 2 is configured to receive the plunger 12 of the present disclosure within the lumen 28, as illustrated in FIG. 18. The plunger 12 can be used to push bone graft material positioned in the lumen 28 out of the openings 7A, 7B at the distal end 8. In one embodiment, a stop 16A can be formed on the plunger 12 to engage the proximal end 6 of the hollow tube 2. In this manner, the stop 16A prevents the over-insertion of the plunger 12 within the lumen 28.

The plunger 12 is generally configured to substantially conform to inner walls of the lumen 28. Specifically, in one embodiment, at least a portion of plunger 12 has a cross-sectional shape which generally corresponds to the interior shape of the lumen 28. In various embodiments, the plunger 12 has a cross section that is round, ovoid, square, or rectangular. In one embodiment, a cross section of the plunger 12 is not round. In another embodiment, at least a portion of the plunger 12 is configured to contact the inner walls of the lumen 28 about an entire outer periphery of the plunger 12.

Figure 21:
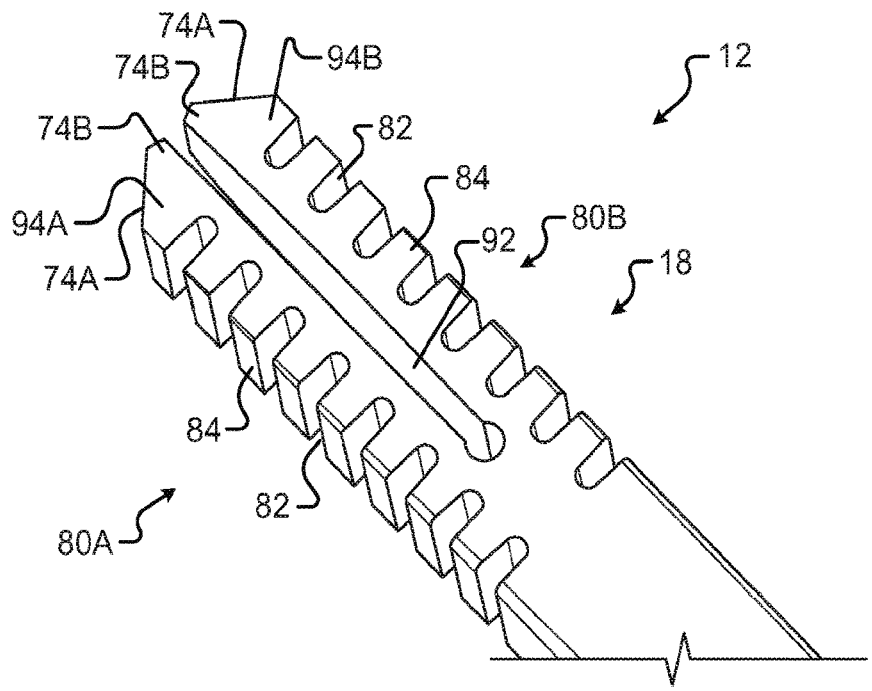
FIG. 21 is a perspective view of a distal portion of a plunger of the graft delivery device of FIG. 18.
Figure 22:
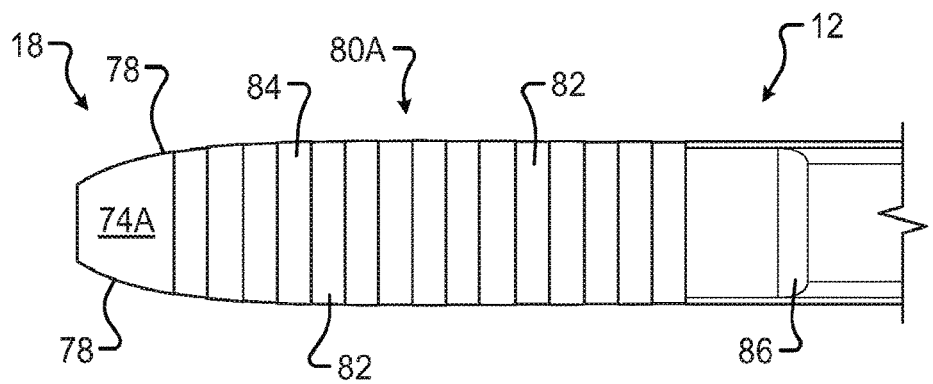
FIG. 22 is a side elevation view of the distal portion of the plunger.
Figure 23:
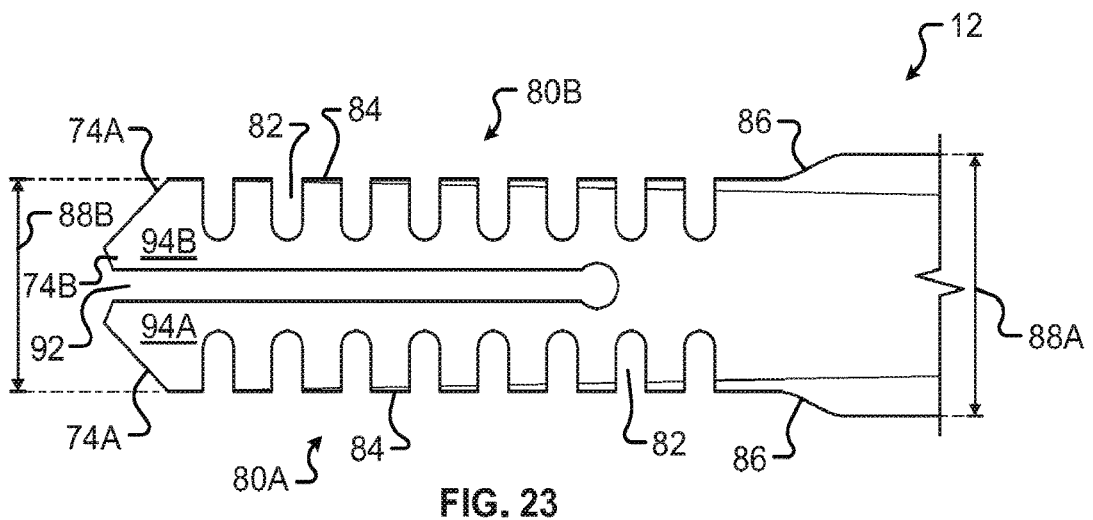
FIG. 23 is a top plan view of the distal portion of the plunger.
Figure 25:
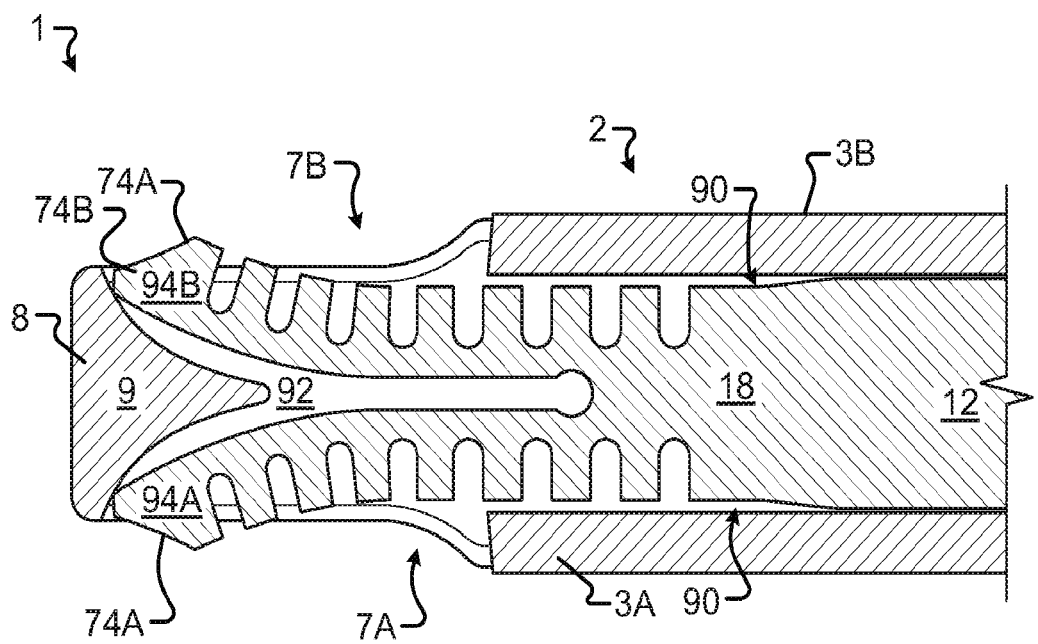
FIG. 25 is another cross-section view of the distal portion of the graft delivery device illustrating the arms of the plunger in a second state after bending transverse to the longitudinal axis.

Referring now to FIGS. 21-23, the plunger 12 includes a distal end 18. The distal end 18 can include one or more blunt surfaces 74. In one embodiment, the blunt surfaces 74 are generally planar at least before the distal end 18 contacts a curved surface 10 of the hollow tube 2. In various embodiments, the blunt surfaces 74 are angled transverse to the longitudinal axis of the plunger 12. For example, in one embodiment, one or more of the blunt surfaces 74 are oriented at an angle of between approximately 30° and 60° relative to the longitudinal axis of the plunger 12. In one embodiment, and referring now to FIG. 23, the distal end 18 includes first blunt surfaces 74A and second blunt surfaces 74B. In one embodiment, the first blunt surfaces 74A have a greater surface area than the second blunt surfaces 74B. Additionally, or alternatively, the first blunt surfaces 74A can be oriented toward the openings 7 of the hollow tube 2. In one embodiment, the first blunt surfaces are substantially orthogonally arranged to the second blunt surfaces. Referring now to FIG. 22, in one embodiment, opposing surfaces 78 of the plunger distal end 18 are tapered to form a rounded or bullet shaped distal end 18. In one embodiment, the opposing surfaces 78 are substantially symmetric. The opposing surfaces 78 facilitate movement of bone graft material out of the lumen 28 of the hollow tube. Additionally, the opposing surfaces 78 allow the distal end 18 to move at least partially out of the openings 7A, 7B of the hollow tube 2 during bone graft delivery to a surgical site, as generally illustrated in FIG. 25.

In one embodiment, the distal end 18 of the plunger 12 (or portions of the plunger 12) are adapted to bend or flex as the plunger is advanced proximate to the distal end 8 of the hollow tube 2. More specifically, in one embodiment, the plunger distal end 18 is bifurcated into a first arm 94A and a second arm 94B by a groove 92 (see FIG. 24). The arms 94 are configured to bend relative to a longitudinal axis of the plunger as generally illustrated in FIG. 25. In this manner, the distal end 18 of the plunger is configured to push substantially all of the bone graft material out of the openings 7A, 7B of the hollow tube 2.

In one embodiment, the arms 94 are configured to bend in response to contact with an interior surface of the hollow tube 2. For example, in one embodiment, the hollow tube 2 has a geometry configured to bend at least the arms 94 of the distal end 18 of the plunger 12 toward the openings 7A, 7B of the hollow tube 2.

Figure 24:
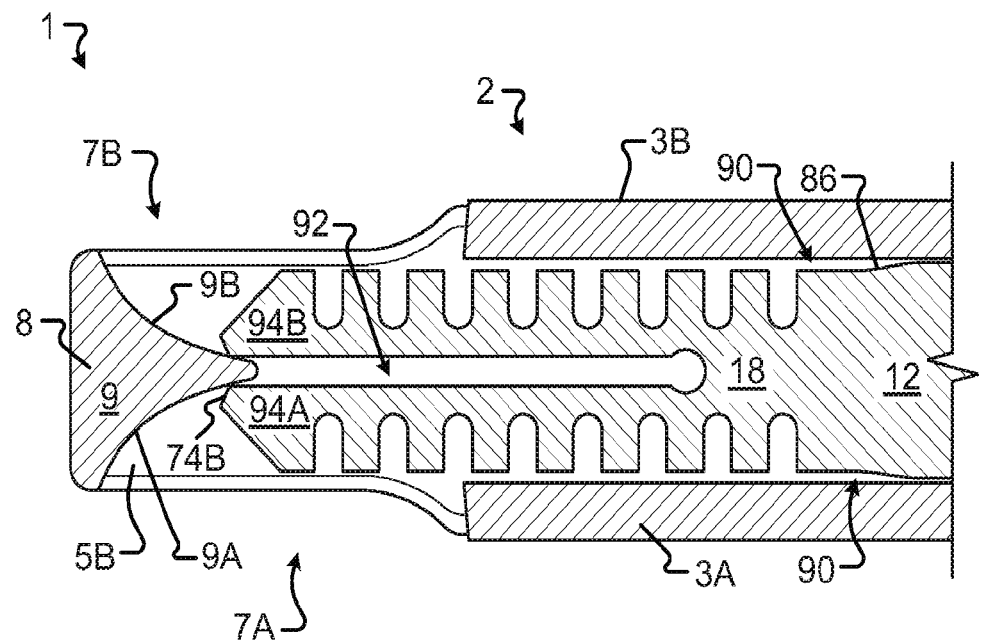
FIG. 24 is a cross-sectional view of a distal portion of the graft delivery device of FIG. 18 illustrating arms of the distal end of the plunger in a first state generally parallel to a longitudinal axis of the plunger.

In one embodiment, the hollow tube 2 includes an interior ramp 9. The ramp 9 is configured to interface with the distal end 18 to alter the path of the plunger arms 94. More specifically, the ramp 9 includes surfaces 9A, 9B configured to deflect or bend the plunger arms 94 from an alignment generally parallel to a longitudinal axis of the plunger (as generally illustrated in FIG. 24) to a bent or deflected position generally transverse to the longitudinal axis and toward the respective first and second openings 7A, 7B (as generally illustrated in FIG. 25). Additionally, the ramp 9 can be used to direct the bone graft material away from the openings 7A, 7B into a surgical site, such as a disc space. In this manner, the ramp 9 can function as a reverse funnel to disperse bone graft material ejected from the opening(s) 7 as generally illustrated in FIG. 9A.

In one embodiment, the ramp 9 comprises ramp surfaces 9A, 9B. In one embodiment, the ramp surfaces 9A, 9B are symmetrically positioned about a longitudinal axis of the hollow tube 2. In various embodiments, the ramp surfaces 9A, 9B are of curvilinear or a arcuate shape. The ramp surfaces 9A, 9B beneficially urge bone graft material, when disposed within the hollow tube 2, to substantially exit the openings 7A, 7B.

Further, the ramp surfaces 9A, 9B are configured to engage one or more blunt surfaces 74A, 74B of the plunger 12 to deflect or bend the arms 94 away from the longitudinal axis of the plunger 12 and toward the openings 7A, 7B of the hollow tube 2. In one embodiment, the blunt surfaces 74A, 74B of the plunger 12 are configured to advance along the ramp surfaces 9A, 9B without catching or sticking. In one embodiment, the second blunt surfaces 74B are configured to contact respective ramp surfaces. Accordingly, the second blunt surfaces 74B can be oriented to slide along the ramp surfaces 9A, 9B. Additionally, or alternatively, the first blunt surface 74A may not contact the ramp surfaces 9A, 9B. In contrast, a plunger with a distal end 18 perpendicular to the plunger longitudinal axis would be stopped by the ramp 9 which would prevent efficient discharge of bone graft from the hollow tube 2.

In one embodiment, the ramp 9 extends from a closed portion of the distal end 8 of the hollow tube 2 toward the proximal end 6 of the hollow tube 2. In one embodiment, the ramp 9 has a length parallel to the longitudinal axis of the hollow tube 2. In various embodiments, the length of the ramp 9 is at least approximately one-third, or about one-half, a length of the openings 7A, 7B. The ramp 9 can also provide structural support for the hollow tube 2. More specifically, by extending the ramp 9 toward the proximal end 6 of the hollow tube 2, the ramp 9 provides support for the top and bottom surface 5A, 5B of the hollow tube 2. In various embodiments, the plunger 12 is made of a flexible material, including, but not limited to a rubber, an elastomeric material, other suitable flexible materials and/or a combination of such materials. In one embodiment, the distal end 18 is made of a material different than the rest of the plunger 12. In one embodiment at least the distal end 18 of the plunger 18 is made of the flexible material.

In various embodiments, the plunger distal end 18 has one or more areas of flexibility 80 (i.e., 80A, 80B) (see FIGS. 21-23). The areas of flexibility 80 are configured to allow at least the arms 94 to bend in a predetermined direction toward the openings 7A, 7B. In one embodiment, the areas of flexibility 80 comprise relief areas 82 formed in the distal end 18. In one embodiment, the relief areas comprise notches 82. In one embodiment, the notches 82 are formed transverse to a longitudinal axis of the plunger 12. In one embodiment, the notches 82 are positioned to face the openings 7 when the plunger 12 is positioned within the hollow tube 2. Alternatively, the notches 82 can be oriented to face away from the openings, such as toward the groove 92 between the arms 94. In various embodiments, the notches 82 are formed such that walls between adjacent notches have outer ends 84 that are generally planar. Additionally, or alternatively, the notches 82 extend at least approximately halfway through the width of the arms 94. In one embodiment, the notches 82 are spaced substantially evenly along the distal end 18. In one embodiment, the notches 82 have a generally uniform size and shape. In an alternate embodiment, the notches 82 have different sizes and/or shapes.

In one embodiment, the area of flexibility 80 is back cut to decrease the width 88B of the plunger distal end 18. In one embodiment, the distal end 18 is back cut to form one or more rabbets 86. In another embodiment, the rabbet 86 is formed on sides of the plunger 12 with the relief areas.

In one embodiment, the rabbets 86 extend generally parallel to a longitudinal axis of the plunger 12. Accordingly, in one embodiment, the distal end 18 can have a width 88B that is less than a width 88A of another portion of the plunger 12 as generally illustrated in FIG. 23. The rabbets 86 can have a depth selected to form gaps 90 between the distal end 18 and an interior of the lumen 28 such as shown in FIG. 24. More specifically the width 88B of the distal end can be less than an interior width of the lumen 28. In one embodiment, the gaps 90 beneficially prevent the plunger arms 94 from contacting and binding against the interior of the lumen 28 as the arms bend toward the openings. For example, when the plunger 18 contacts the curved surfaces of the ramp 9 of the hollow tube 2, the arms 94A, 94B may buckle or bulge at least slightly. The gaps 90 provides clearance between the plunger 12 and the hollow tube 2 if the arms 94A, 94B buckle.

In various embodiments, the plunger 12 includes a plurality of teeth and notches that are the same as, or similar to the teeth and notches 27 of the plunger described in conjunction with FIG. 7A. The notches can be engaged by a means for advancing bone graft material described herein. In this manner, the advancing means can move the plunger 12 relative to the hollow tube 2. In various embodiments, the advancing means comprise a ratchet, a gear, a worm gear with a helical thread and the like, such as described herein.

In one embodiment, the funnel 30 is releasably interconnected to a proximal end 6 of the hollow tube 2 to facilitate loading of bone graft material into the opening 4. Thereafter, the funnel 30 can be removed to improve visualization of the distal end 8 and opening 7 in a surgical site. The funnel 30 can be the same as one or more other funnels 30 of the present disclosure.

In various embodiments, the graft delivery device 1 includes at least one vent port to release air from the lumen 28 as bone graft material is advanced to the distal end 8 for discharge out of the openings 7. Although the vent port is not illustrated in FIGS. 18-25 for clarity, the vent port can be as described in other embodiments of the graft delivery device described herein. For example, the vent ports 21 described in conjunction with FIG. 7A can be used with the graft delivery device 1 illustrated in FIGS. 18-25.

In various embodiments, indicia is formed on one or more surface of the hollow tube 2. The indicia can be the same as or similar to the indicia 29 described in conjunction with FIG. 7. The indicia are configured to indicate a depth of insertion of the distal end 8 of the hollow tube 2 into a surgical site. The indicia can include markings and numerals. In various embodiments, one or more of the indicia is radiopaque. In various embodiments, the indicia extends along the entire length of the hollow tube 2, or along a predetermined portion of the length.

In one embodiment, the hollow tube 2 can receive a fusion cage 60 of an embodiment of the present invention. The fusion cage 60 can have a fixed height or be expandable after placement in a disc space. The fusion cage 60 can have at least one opening 65 to discharge bone graft material therethrough. The opening 65 can be alignable with the openings 7 of the hollow tube 2. The fusion cage 65 can have a distal end 64 that is blunt, tapered, or wedge shaped. The hollow tube 2 can be configured to interconnect to other fusion cages.

In various embodiments, the hollow tube 2 is made of a flexible, semi-rigid, or rigid material including one or more of a plastic, a composite, a metal. In one embodiment, the hollow tube 2 is formed of polycarbonate resin thermoplastic. In various embodiments, at least a portion of the hollow tube 2 is radiopaque. In one embodiment, at least the distal end 8 is radiopaque or includes radiopaque markers, such as indicia 29 describe herein.

In one embodiment, the hollow tube 2 is substantially rigid. Optionally, at least a portion of the hollow tube 2 may be flexible. For example, in one embodiment, at least about one-half of the hollow tube 2 comprising the distal end 8 is flexible. In one embodiment, the hollow tube 2 is generally linear.

In one embodiment, the hollow tube 2 is made of a substantially transparent or translucent material, and the hollow tube is not opaque. In one embodiment, at least a portion of the hollow tube 2 is transparent or translucent. In one embodiment, the hollow tube 2 includes windows of a transparent or translucent material. Accordingly, in some embodiments, the plunger 12 is at least partially visible within the lumen 28 of the hollow tube 2

In various embodiments, the hollow tube 2 includes one or more image sensing device(s), such as an endoscope, camera, and/or an image sensor. The image sensing device(s) can be the same as or similar to the image sensing device(s) 36 described in conjunction with FIG. 7D. In various embodiments, the image sensing device(s) is removably or permanently coupled to the hollow tube 2. In one embodiment, the image sensing device(s) is oriented to view at least the distal end 8 of the hollow tube 2. Additionally, or alternatively, the image sensing device(s) is configured to view an internal aspect of a disc space 172A.

Figure 26:
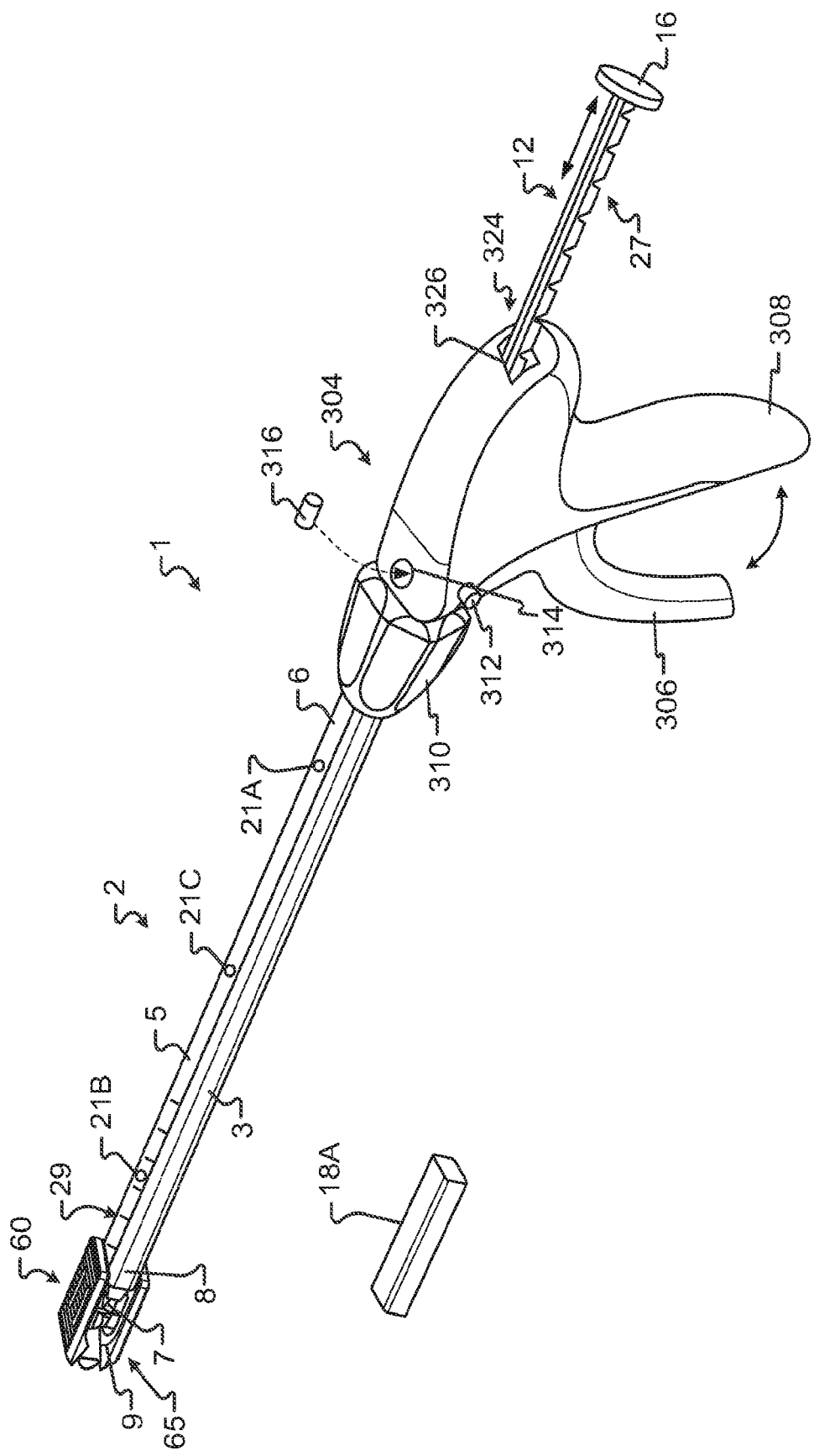
FIG. 26 is a top perspective view of another embodiment of a device for delivering bone graft.

Embodiments of the graft delivery device 1 illustrated in FIGS. 18-25 can also be used by a surgeon to repair a collapsed/injured vertebrae, in the same ways as discussed above in connection with the graft delivery device of FIGS. 1-7G. Referring now to FIG. 26, another embodiment of an integrated fusion cage 60 and graft delivery device 1 of the present disclosure is illustrated. The integrated device 1 generally includes a hollow tube 2, a fusion cage 60, and a means for advancing bone graft material through the hollow tube. In various embodiments, the advancing means includes the use of manual force, mechanical force, electric force, pneumatic force, or any other force to advance bone graft material through the hollow tube 2. In one embodiment, a user can manipulate the integrated device 1 with a single hand. This beneficially frees the user's other hand for other action.

In one embodiment, the advancing means includes a handle or grip 304. The grip 304 is operable to selectively move bone graft material through the lumen of the hollow tube 2 for discharge from an opening 7 at the tube distal end 8.

The hollow tube 2 includes a proximal end 6 configured to releasably interconnect to the grip 304. Bone graft material can be positioned within the lumen of the hollow tube 2, such as with a funnel 30 (illustrated in FIG. 7B). The funnel 30 may then be removed from the proximal end 6. The proximal end 6 can then be interconnected to the grip 304. Optionally, the hollow tube 2 can be used to eject bone graft material into a surgical site without being affixed to the grip 304.

In various embodiments, the grip 304 frictionally engages the tube proximal end 6. In various embodiments, the hollow tube 2 or the grip 304 includes a lock or a latch to secure the hollow tube 2 to the grip 304. In another embodiment, a portion of the hollow tube 2 can threadably engage the grip 304. In another embodiment, the proximal end 6 and grip 304 are interconnected with a bayonet mount. In still another embodiment, the grip 304 includes a knob 310 such that the hollow tube 2 can be selectively interconnected to the grip 304. Other means of interconnecting the hollow tube 2 to the grip 304 are contemplated.

A channel 324 is formed through the grip 304. The channel 324 includes a proximal opening 326 and extends through the grip 304 and the knob 310. In one embodiment, the opening 326 is configured to receive a plunger 12. The plunger 12 can extend through the channel 324 into a hollow tube 2 interconnected to the grip 304.

The grip 304 includes a means for advancing bone graft material through the lumen 28 of the hollow tube 2 (i.e., the lumen 28 as shown in FIGS. 12 and 20). In one embodiment, the advancing means comprises a compressed fluid. Specifically, in one embodiment, the grip 304 is configured to advance the bone graft material using the compressed fluid, such as air. Manipulating the grip trigger 306 can release compressed fluid into the proximal end 6 of the lumen. In one embodiment, the hollow tube includes a single vent port 21B at the distal end. When a proximal end of bone graft material within the lumen reaches the vent port 21B, the compressed fluid is released from the lumen. In this manner, the fluid is not introduced into the surgical site.

In one embodiment, a pusher 18A is positioned in the lumen 28 of the hollow tube 2 after the lumen is loaded with bone graft material. The pusher 18A may be similar to the distal end 18 of a plunger 12, such as generally illustrated in FIG. 7A. Regardless, the pusher 18A is configured to substantially conform to interior surfaces of the lumen 28. In this manner, the pusher 18A prevents the fluid from being discharged from the opening 7 into the surgical site.

When a pressurized fluid is introduced into the lumen 28 behind the pusher 18A, the pusher advances toward the distal end 8. The bone graft material is urged toward the distal end 8 and through the opening 7 by the pusher 18A. In one embodiment, when a proximal end of the pusher 18A advances past the vent port 21B, the compressed fluid is released from the lumen 28 and the pusher 18A stops. Alternatively, the pusher may stop advancing by contact with an interior ramp 9 within the hollow tube 2.

In another embodiment, the means for advancing the bone graft material comprises a plunger 12. Accordingly, in one embodiment, the grip 304 is configured to selectively advance a plunger 12 through the lumen 28 to advance the bone graft material. The grip 304 is configured to advance the plunger 12 axially with respect to the lumen 28 of the hollow tube 2. Specifically, the grip 304 can manipulate the plunger 12 such that a distal end of the plunger 12 opposite the plunger handle 16 moves towards the distal end 8 of the hollow tube 2. The grip 304 is configured to manually or automatically apply a force to the plunger 12. In various embodiments, the force is generated by one or more of a user, a motor, a compressed fluid, or any other means of generating a force.

In various embodiments, the plunger 12 includes teeth, notches 27, or depressions which are engageable by the grip 304 to axially adjust the position of the plunger 12. The notches 27 can be substantially evenly spaced along the plunger 12.

In one embodiment, a motor is positioned within the grip 304 to advance the plunger 12. In one embodiment, the motor is operable to rotate a shaft. The shaft may include a gear to translate the rotational movement into a linear movement of the plunger 12. In one embodiment, the gear includes teeth to engage the notches 27 or teeth of the plunger 12. A battery can provide power to the motor. In one embodiment, the battery is housed in the grip 304.

In various embodiments, the grip includes a gear or a ratchet configured to engage teeth, notches 27, or depressions on the plunger 12. Specifically, in one embodiment, the ratchet of the grip 304 is configured to engage the plurality of notches 27 formed in the plunger 12. In one embodiment, the channel 324 of the grip 304 includes an aperture or window through which a portion of the gear or ratchet can extend to engage the plunger 12.

In one embodiment, when activated, the ratchet engages a first notch and then a second notch to incrementally advance the plunger 12 distally within the hollow tube 2. Bone graft material within the hollow tube 2 is then pushed by the plunger 12 toward the distal end 8 of the hollow tube 2. Ratcheting mechanisms that can be used with the grip 304 are known to those of skill in the art. Some examples of ratcheting mechanisms are described in U.S. Pat. App. Pub. 2002/0049448, U.S. Pat. App. Pub. 2004/0215201, U.S. Pat. App. Pub. 2009/0264892, U.S. Pat. Nos. 7,014,640, 8,932,295, 9,655,748, and 9,668,881 which are each incorporated herein by reference in their entirety.

In various embodiments, the grip 304 is configured to discharge a predetermined amount of bone graft material each time the plunger 12 is incrementally advanced within the hollow tube 2. In one embodiment, between about 0.25 and 1.0 cc of bone graft material is discharged from the distal end 8 of the hollow tube 2 each time the plunger is advanced. In another embodiment, between about 0.25 and 1.0 cc of bone graft material is discharged is discharged each time the trigger 306 is actuated by a user.

In one embodiment, the grip 304 is configured to enable vision of a surgical sight by a user. Specifically, the grip 304 may be substantially even with one or more surfaces 3, 5 of the hollow tube 2. In this manner, in one embodiment, the grip 304 does not obstruct a line of sight along at least one surface 3, 5. In another embodiment, an exterior surface of the grip 304 is about even with a plane defined by one of the side surfaces 3. Additionally, or alternatively, an upper portion of the grip 304 does not extend beyond a plane defined by a top surface 5 of the hollow tube. Optionally, a window or view port is formed in the grip 304 to allow view of the distal end 8 of the hollow tube 2.

In various embodiments, the integrated fusion cage and graft delivery device 1 includes a visualization system. In various embodiments, the visualization system includes (but is not limited to) one or more of a camera, a light, an endoscope, and a display. In various embodiments, the visualization system is permanently or removably affixed to the integrated fusion cage and graft delivery device 1. In one embodiment, the visualization system is affixed to the hollow tube 2.

In one embodiment, the grip 304 includes a motor or other actuator which can be manipulated by a user to advance or withdraw the plunger in the hollow tube 2. The motor or actuator can operate the ratchet.

In various embodiments, the grip 304 is manually manipulated by a user to move the plunger 12. In one embodiment, the grip 304 includes a trigger 306. In various embodiments, the trigger 306 is hinged or pivotally interconnected to the grip 304. When the trigger 306 is actuated by a user, the plunger 12 is advanced in the hollow tube 2.

In one embodiment, actuating the trigger 306 included pulling the trigger toward a handle 308 of the grip. In one embodiment, the trigger 306 is biased away from the handle 308, as generally illustrated in FIG. 26. Pulling the trigger 306 toward the handle 308 causes the ratchet to engage the plunger 12. The ratchet engages a notch 27 of the plunger 12 and moves the plunger toward the distal end 8 of the hollow tube. Successively pulling the trigger 306 incrementally advances the plunger 12 forward in the hollow tube 2.

In one embodiment, the ratchet is operably connected to an upper end of the trigger 306. In this embodiment, pulling the trigger 306 causes the ratchet to move toward the hollow tube 2. In one embodiment, a lock pawl (not illustrated) is operably connected to the grip 304. The lock pawl can engage a notch of the plunger 12 to prevent inadvertent movement of the plunger 12 distally.

The grip 304 is used to advance or withdraw the plunger 12. In one embodiment, the grip 304 includes a switch 312 operable to change the direction of movement of the plunger 12. By manipulating the switch 312, a user can cause the plunger 12 to advance into the hollow tube 2 or, alternatively, withdraw from the hollow tube 2. In one embodiment, to withdraw the plunger 12, the plunger handle 16 can be pulled away from the grip 304. In one embodiment, the switch 312 comprises a button.

In various embodiments, the grip 304 includes a loading port 314, as illustrated in FIG. 26. The loading port 314 provides access to the lumen of the hollow tube 2. In one embodiment, the loading port 314 is in fluid communication with the channel 324 through the grip 304. Accordingly, bone graft material can be added to the hollow tube through the loading port 314. In one embodiment, the loading port 314 is configured to engage a funnel 30 of any embodiment of the present disclosure. Additionally, or alternatively, a syringe 42 may interconnect to the grip 304 to discharge bone graft material 42 into the lumen through the loading port.

Additionally, or alternatively, a capsule or package 316 of bone graft material can be loaded into the lumen 28 through the loading port 314. The package 316 can include any type of bone graft material, including one or more of: autogenous (harvested from the patient's own body), allogeneic (harvested from another person), and synthetic. A predetermined amount of bone graft material can be included in the package 316. In one embodiment, each package includes between about 0.25 and 1.0 cc of bone graft material. One or more packages 316 may be loaded into the lumen 28 to deliver a desired amount of bone graft material to a surgical site.

Embodiments of the integrated infusion cage 60 and graft delivery device 1 illustrated in FIG. 26 can also be used by a surgeon to repair a collapsed/injured vertebrae, in the same ways as discussed above in connection with the graft delivery device of FIGS. 1-7G.

Figure 27:
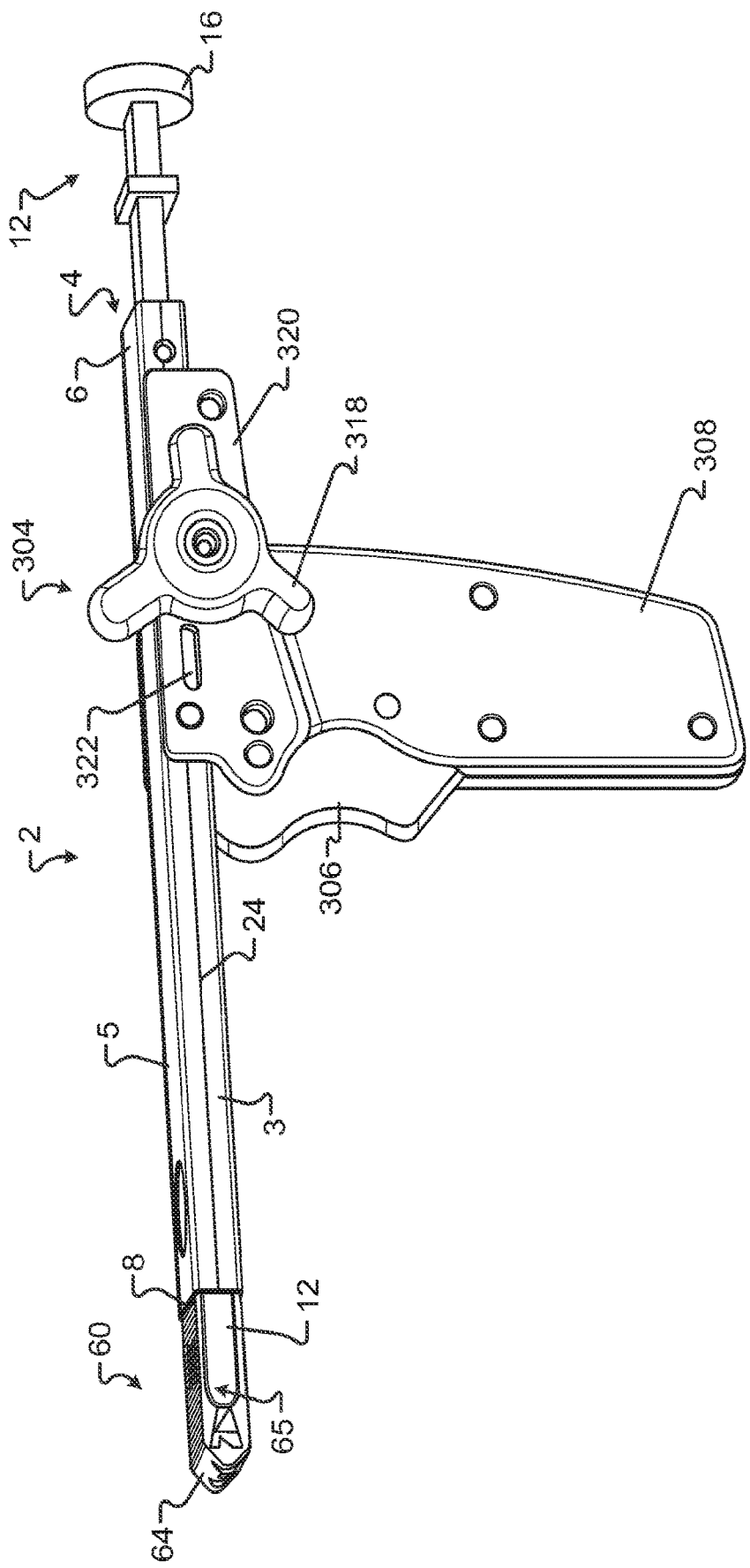
FIG. 27 is a top perspective view of still another integrated fusion cage and graft delivery device of the present disclosure.

Referring now to FIG. 27, still another embodiment of an integrated fusion cage 60 and graft delivery device 1 of the present disclosure is illustrated. The device 1 illustrated in FIG. 27 is similar to the device 1 described in conjunction with FIG. 26 and includes many of the same, or similar features. The integrated device 1 generally includes a hollow tube 2 configured to receive a fusion cage 60 and a means for advancing bone graft material through the hollow tube for discharge out of an opening 65 of the fusion cage 60.

In one embodiment, the advancing means includes a grip 304. The grip 304 is configured to interconnect to a hollow tube 2 of any embodiment of the present disclosure. The grip 304 is operable to selectively move bone graft material through the lumen 28 (not shown) of the hollow tube 2 for discharge from the tube distal end 8. Bone graft material can be positioned within the lumen while the hollow tube 2 is interconnected to the grip 304.

In one embodiment, the grip 304 frictionally engages a predetermined portion of the hollow tube 2. In various embodiments, the hollow tube 2 or the grip 304 include a lock or a latch to secure the hollow tube 2 to the grip 304. In one embodiment, the grip 304 engages at least the two side surfaces 3 of the hollow tube 2. In one embodiment, the grip 304 includes opposing flanges 320. One or more of the flanges 320 can be moved inwardly toward the hollow tube 2, similar in operation to a clamp. In this manner, the flanges 320 can apply a compressive force to the side surfaces 3 to interconnect the hollow tube 2 to the grip. Other means of interconnecting the hollow tube 2 to the grip 304 are contemplated.

The grip 304 includes a means for advancing bone graft material through the lumen of the hollow tube 2. In one embodiment, the advancing means comprises a compressed fluid. Specifically, in one embodiment, the grip 304 is configured to advance the bone graft material using the compressed fluid, such as air. Manipulating the grip trigger 306 can release compressed fluid into the proximal end 6 of the lumen. When a pressurized fluid is introduced into the lumen, the plunger 12 advances toward the distal end 8. The bone graft material is urged toward the distal end 8 and through the opening 65 by the plunger 12. In one embodiment, the plunger 12 stops advancing by contact with an interior ramp within the hollow tube 2.

In another embodiment, the means for advancing the bone graft material is configured to selectively advance the plunger 12 through the lumen to advance the bone graft material. Specifically, the grip 304 is configured to manually or automatically apply a force to the plunger 12. In various embodiments, the force is generated by one or more of a user, a motor, a compressed fluid, or any other means of generating a force.

In one embodiment, a motor is positioned within the grip 304 to advance the plunger 12. In one embodiment, the motor is operable to rotate a shaft. In one embodiment, the shaft includes a gear to translate the rotational movement of the shaft into a linear movement of the plunger 12. In one embodiment, the plunger includes notches to engage the gear of the shaft. In one embodiment, a battery provides power to the motor. In one embodiment, the battery is housed in the grip 304.

In various embodiments, the plunger 12 includes teeth, notches, or depressions which are engageable by the grip 304 to axially adjust the position of the plunger 12. In various embodiments, the grip includes a gear or a ratchet configured to engage teeth or notches on the plunger 12. Specifically, in one embodiment, the ratchet of the grip 304 is configured to engage a plurality of notches formed in the plunger. In one embodiment, the notches are substantially evenly spaced along the plunger. The ratchet engages a first notch and then a second notch to incrementally advance the plunger distally within the hollow tube 2. Bone graft material within the hollow tube 2 is then pushed by the plunger 12 toward the distal end 8 of the hollow tube.

In one embodiment, the grip 304 is configured to enable vision of a surgical sight by a user. Specifically, in one embodiment, the grip 304 does not extend above a top surface 5 of the hollow tube. In this manner, in one embodiment, the grip 304 does not obstruction a line of sight along at least the top surface 5. In another embodiment, lateral surfaces of the grip are about even with a plane defined by one of the side surfaces 3 of the hollow tube.

In various embodiments, the grip 304 includes a motor or other actuator which can be manipulated by a user to advance or withdraw the plunger 12 in the hollow tube 2. The motor or actuator can operate the ratchet.

In various embodiments, the grip 304 is manually manipulated by a user to move the plunger 12. In one embodiment, the grip 304 includes a trigger 306. In various embodiments, the trigger 306 is hinged or pivotally interconnected to the grip 304. When the trigger 306 is actuated by a user, the plunger 12 advances in the hollow tube 2. Specifically, in one embodiment, the trigger 306 is functionally interconnected to the plunger 12.

In one embodiment, actuating the trigger 306 includes pulling the trigger 306 toward a handle 308 of the grip 304. In one embodiment, the trigger 306 is biased away from the handle 308, as generally illustrated in FIG. 27. In one embodiment, pulling the trigger 306 toward the handle 308 causes the ratchet to engage the plunger 12. The ratchet engages a notch of the plunger 12 and moves the plunger 12 toward the distal end 8 of the hollow tube 2. Successively pulling the trigger 306 incrementally advances the plunger 12 forward in the hollow tube 2.

In one embodiment, the ratchet is associated with an upper end of the trigger 306. In this embodiment, pulling the trigger 306 causes the ratchet to move toward the distal end of the hollow tube 2. In one embodiment, a lock pawl (not illustrated) is operably connected to the grip 304. In one embodiment, the lock pawl engages a notch of the plunger 12 to prevent the plunger 12 from moving distally.

The grip 304 is used to advance or withdraw the plunger 12. In one embodiment, the grip 304 includes a switch operable to change the direction of movement of the plunger 12. By manipulating the switch, a user can cause the plunger 12 to advance into the hollow tube 2 or, alternatively, withdraw from the hollow tube 2. In one embodiment, to withdraw the plunger 12, the plunger handle 16 is pulled away from the grip 304.

In various embodiments, the grip 304 includes a knob 318. In one embodiment, the knob 318 is configured to advance or withdraw the plunger 12 within the hollow tube 2. Specifically, rotating the knob 318 in a first direction causes the plunger 12 to advance toward the distal end 8. Rotating the knob 318 in a second direction causes the plunger 12 to withdraw away from the distal end 8.

In one embodiment, the knob 318 includes a gear, such as a pinion. The gear includes teeth that engage notches or teeth extending linearly along the plunger 12, similar to a rack. Rotational movement of the knob 318 is converted into linear motion of the plunger 12 by interaction between the knob pinion with the plunger rack.

In various embodiments, the hollow tube 2 discharges a predetermined amount of bone graft material associated with each rotation, or partial rotation of the knob 318. Specifically, a calibrated amount of bone graft material may be discharged from the hollow tube 2 for each quarter, half, or full rotation of the knob 318. In one embodiment, the hollow tube 2 is configured to discharge approximately 1 cc of bone graft material for each half turn of the knob 318.

In one embodiment, the knob 318 is configured to provide tactile feedback to a user after a predetermined amount of rotation. For example, when the knob 318 is rotated one or more of ⅛, ¼, ½, and 1 turn, the knob 318 and/or the grip 304 may vibrate or provide other tactile feedback to the user.

The grip 304 is also operable to expand the fusion cage 60 and separate the fusion cage 60 from the hollow tube 2. In one embodiment, the knob 318 slides within a slot 322 to release the fusion cage 60. In one embodiment, pulling the knob 318 away from the distal end 8 of the hollow tube 2 detaches the fusion cage 60.

Embodiments of the integrated infusion cage 60 and graft delivery device 1 illustrated in FIG. 27 can also be used by a surgeon to repair a collapsed/injured vertebrae, in the same ways as discussed above in connection with the graft delivery device of FIGS. 1-7G.

In one embodiment, a bone graft tamping device (not shown) is provided, and is adapted to be inserted into the hollow tube 2 after the plunger 12 is removed from the hollow tube 2. The bone graft tamping device, according to this embodiment, may include one or more longitudinal channels along the outer circumference of the bone graft packer for permitting any trapped air to flow from the bone graft receiving area to the graspable end of the hollow tube during packing of bone graft. The bone graft packer may further include a handle at one end designed ergonomically for improving ease of use. The bone graft packer in this embodiment thereby facilitates packing of bone graft within the hollow tube.

In one embodiment, the hollow tube 2 is fitted with a passageway wherein a surgical tube or other device may be inserted, such as to deliver a liquid to the surgical area or to extract liquid from the surgical area. In such an embodiment, the plunger 12 is adapted in cross-section to conform to the hollow tube's cross-section.

In another embodiment of the present invention, a kit of surgical instruments comprises a plurality of differently sized and/or shaped hollow tubes 2 and a plurality of differently sized and/or shaped plungers 12. Each of the plungers correspond to at least one of the hollow tubes, whereby a surgeon may select a hollow tube and a plunger which correspond with one another depending upon the size and shape of the graft receiving area and the amount or type of bone graft to be implanted at such area. The corresponding hollow tubes and plungers are constructed and arranged such that bone graft can be placed within the hollow tubes with the plungers, and inserted nearly completely into the hollow tubes for removing substantially all of the bone graft material from the hollow tubes, such as in the preferred embodiments for the plunger described above. The use of more than one hollow tube/plunger combination permits at least two different columns of material to be selectively delivered to the targeted site, e.g. one of bone graft material from the patient and another of Bone Morphogenetic Protein (BMP), or e.g. two different types of bone graft material or one delivering sealant or liquid. Also, one or both hollow tubes could be preloaded with bone graft material.

In various embodiments, the kit of surgical instruments comprises a plurality of differently sized and/or shaped graft retaining structures, each corresponding to at least one hollow tube and at least one plunger.

The bone graft receiving area can be any area of a patient that requires delivery of bone graft. In the preferred embodiment, the bone graft is delivered in a partially formed manner, and in accordance with another aspect of the present invention, requires further formation after initial delivery of the bone graft.

Another embodiment of the present invention provides a method by which a hollow tube and a plunger associated with the hollow tube are provided to facilitate delivery of the bone graft to a bone graft receiving area.

According to one embodiment, the present invention provides a bone graft delivery system, by which a hollow tube and/or plunger assembly are prepared prior to the surgical procedure on the patient begins, thus minimizing the overall impact of the grafting aspect of a surgical implantation or other procedure. In various embodiments, the hollow tube 2 is made to be stored with bone graft in it for a period of time, whether the tube is made of plastic, metal or any other material. Depending upon the surgical application, it may be desirable to only partially fill the tube for storage, so that a plunger can be at least partially inserted at the time of a surgery.

In various embodiments, the integrated fusion cage 60 and graft delivery device 1 come with a pre-filled hollow tube 2 (i.e., with bone graft), or a non-filled hollow tube 2, in which the surgeon will insert bone graft received from the patient (autograft), or from another human source (allograft). In either case, the surgeon may first remove any wrapping or seals about the hollow tube 2, and/or the pre-filled bone graft, and insert the hollow tube 2 into the patient such that the second end of the hollow tube is adjacent the bone graft receiving area. Once the hollow tube 2 is in place, and the opening at the second end of the hollow tube is oriented in the direction of the desired placement of bone graft, the surgeon inserts the second end of the plunger 12 into the opening at the first end of the hollow tube, and begins pressing the second end of the plunger against the bone graft material in the hollow tube. In this fashion, the plunger 12 and hollow tube 2 cooperate similar to that of a syringe, allowing the surgeon to steadily and controllably release or eject bone graft from the second end of the hollow tube as the plunger is moved farther and farther into the opening in the hollow tube. Once the desired amount of bone graft has been ejected from the hollow tube 2 (in some instances all of the bone graft has been ejected from the hollow tube) the surgeon removes the plunger 12 from the hollow tube, and completes the surgery. In certain operations, the surgeon may elect to place additional bone graft into the hollow tube, and repeat the steps described above. In one embodiment, the pre-filled bone graft elements are color-coded to readily identify the type of bone graft material contained therein.

According to the embodiment described in the preceding paragraph, the present invention may be carried out by a method in which access is provided to a graft receiving area in a patient's body, bone graft is placed into a hollow tube 2 having a first end and a second end, the hollow tube, together with the bone graft, is arranged so that the first end of the hollow tube is at least adjacent to the graft receiving area and permits lateral or nearly lateral (in relation to the longitudinal axis of the hollow tube and plunger assembly) introduction of bone graft to the graft receiving area. This method prevents loss of bone graft due to improper or limited orientation of the integrated fusion cage and graft delivery device, and further allows a user to achieve insertion of a desired quantity of bone graft by way of the contoured plunger and hollow tube configuration described according to preferred embodiments herein.

In another embodiment, the method of the present invention is carried out by providing a hollow tube 2 having a first end and a second end. The tube 2 is constructed so that it may receive a measurable quantity of bone graft, and so that the first end may be arranged at least adjacent to a bone graft receiving area, and so that bone graft can be delivered from the first end of the hollow tube through the second end of the hollow tube and eventually to the bone graft receiving area upon movement of the plunger 12 in a generally downward direction through the hollow tube (i.e., in a direction from the first end to the second end). In one embodiment, a graft retaining structure is also provided for use in connection with the contoured edge of the plunger 12, such that the graft retaining structure is positioned between the contoured edge of the plunger and the bone graft, but which is adhered to the bone graft and remains at the graft receiving area following removal from the hollow tube. In one embodiment, the bone graft is provided in discrete packages or containers. In another embodiment, this graft retaining structure is employed with another tool, such as a graft packer, which is employed either before or after the hollow tube is removed from the graft receiving area.

In another embodiment, the one or more plungers 12 corresponding to the one or more hollow tubes 2 are positioned with distal ends near the proximate end of the horizontal tube before use. In one embodiment, the plungers have a detent to retain the plunger in ready position without undesired movement before the surgeon chooses which one or more plungers to extend through one or more hollow horizontal tube and deliver bone graft material and/or desired material to the surgical area.

According to another embodiment of the present invention, a hollow tube and plunger assembly is provided in which the hollow tube and/or the plunger assembly is disposable. Alternatively, the tube may be made of a biocompatible material which remains at least partially in the patient without impairing the final implantation. Thus, the hollow tube may be formed from a material that is resorbable, such as a resorbable polymer, and remain in the patient after implantation, so as not to interfere with the growth of the bone or stability of any bone graft or implant.

The current design of the graft delivery device 1 of the present invention preferably comprises a hollow tubular member comprising a rounded edge rectangular shaft, which may be filled by the surgeon during surgery, or is pre-filled with grafting material. The loading is carried out by the plunger. The rectangular design is preferable as it allows the largest surface area device to be placed into the annulotomy site of a disc, but in other embodiments may be formed similar to conventional round shafts. The other preferred feature includes a laterally-mounted exit site for the graft material. The combination of this design feature allows direction-oriented dispersion of the graft material. This allows ejection of the graft material into an empty disc space as opposed to below the hollow tube, which would tend to impact the material and not allow its spread through a disc space.

Another feature of this design of the graft delivery device 1 of the present invention is that a rectangular design allows the user to readily determine the orientation of the device and thereby the direction of entry of the bone graft material into the surgical area. In other embodiments, this feature may be achieved by exterior markings or grooves on the exterior on the hollow tube. In various embodiments, such exterior grooves or markings allow the use of a range of cross-sections for the device, including a square, circle, or oval, while allowing a user to readily determine the orientation of the device relative to the direction of entry of the bone graft material into the surgical area.

A further feature of this design of the graft delivery device 1 of the present invention is that an anti-perforation footing or shelf is placed on the bottom of the hollow tube to prevent annular penetration and/or injury to the patient's abdomen or other anatomy adjacent the bone graft receiving area.

In another embodiment of the present invention, all or some of the elements of the device or sections of all or some of the device may be disposable. Disposable medical devices are advantageous as they typically have reduced recurring and initial costs of manufacture.

In another embodiment of the device, the distal tip or end of the plunger device is composed of a different material to the rest of the plunger, so as the material at the distal end of the plunger is sponge-like or softer-than or more malleable than the rest of the plunger so as upon engagement with the interior distal end of the hollow tube, the distal end of the plunger substantially conforms to the interior configuration of the hollow tube. Similarly, the plunger distal end may be made of a material that is adaptable to substantially conform to the interior shape of the distal end of the hollow tube. Such configurations enable substantially all of the material contained within the plunger to be delivered to the targeted site.

Another alterative embodiment of the design described herein includes navigation aiding indicia 29 on one or more surfaces of the hollow tube 2 (see, for example, FIG. 7B) to permit a surgeon to know how far the device 1 has been inserted or to ensure proper alignment relative to a transverse bone graft delivery site (i.e. disc space). Such capability is particularly important when the patient or surgical area is not positioned immediately below the surgeon, or multiple procedures are being performed. Navigation aiding indicia allows more immediate and reliable locating of the surgical area for receiving of bone graft material. In one embodiment, indicia 29 includes the hollow tube 2 being scored or marked, or otherwise providing some affirmative indication, actively or passively, to the surgeon to indicate degree of delivery of the material, e.g. bone graft material, to the delivery site, and/or position of the plunger 12. For example, the exterior of the hollow tube 2 could be color-coded and/or provided with bars as the indicia 29. In another embodiment, a computer and/or electro-mechanical sensor or device is used to provide feedback to the surgeon to indicate degree of delivery of the material, e.g. amount of cc's of bone graft material, to the delivery site, and/or position of the plunger element.

In another alterative embodiment to the design described herein, the plunger 12 includes an activation device, which is often in a liquid or semi-liquid state, and that is injected once the semi-solid portion of the morphogenic protein has been displaced by the movement of the plunger 12 through the hollow tube 2. That is, the plunger 12 pushes the dry material, and once completed, has a bulb or other device on the usable end to insert the liquid portion of the activating agent through the inner lumen 28 within the plunger 12 to evacuate the liquid from the plunger and out an opening at the non-usable end of the plunger so as to contact the dry material already inserted into the disc space.

In one embodiment of the device, all or portions of the device 1 are manufactured using 3-D printing techniques. In another embodiment, all or portions of the device are made by injection molding techniques.

In one embodiment, the ratio of the surface area of the bottom tip of the plunger 12 is approximately half the surface area of the two lateral openings at the distal portion of the hollow tube.

In one embodiment, the device 1 includes a supplemental means of gripping the device, such as a laterally extending cylindrically-shaped handle that engages the hollow tube 2.

In one embodiment, the material inserted into the hollow tube 2 is a non-Newtonian fluid. In one embodiment, the device 1 is adapted to accept and deliver compressible fluids. In another embodiment, the device is adapted to accept and deliver non-compressible fluids. The hollow tube 2 of one embodiment includes a rectangular lumen 28 which provides an increased cross-sectional footprint relative to a round lumen of other bone graft delivery devices. The increased cross-sectional footprint decreases friction of the non-Newtonian fluid material against the interior walls of the lumen, resulting in an improved flow of bone graft material through the lumen and eliminating (or reducing)

jamming due compression of the bone graft material. The increased cross-section of hollow tube 2 of the present disclosure improves the flow dynamics of a non-Newtonian fluid by 40% compared to a prior art tool with a diameter equal to the height of the rectangular lumen of embodiments of the present invention.

In one embodiment, the upper portion of plunger 12 is fitted with one or more protrusions, which extend from the surface of the plunger so as to engage the upper surface of the hollow tube, to prevent the plunger from engaging the distal interior portion of the hollow tube. In one embodiment, an upper portion of plunger 12 is fitted with one or more protrusions to prevent the plunger from engaging the apex of the hollow tube distal interior ramp surface.

In one embodiment, the funnel 30 attaches to the hollow tube 2 by a bayonet connection. In one embodiment, the funnel 30 attaches to the hollow tube 2 by an interference fit. In one embodiment, the funnel 30 attaches to the hollow tube 2 by a threaded connection. In one embodiment, the funnel 30 attaches to the hollow tube 2 by a slot/groove connection.

In one embodiment, the distal end 8 of hollow tube has one opening 7. In one embodiment, the hollow tube 8 has two distal openings 7A, 7B located on opposite sides. In one embodiment, the hollow tube has no more than two openings 7, the openings located on opposite sides.

In one embodiment, after bone graft material 44 is delivered to a surgical site 172, a cavity 174 approximately defined by the volume engaged by the device 1 when inserted into the surgical site is left in the surgical site upon removal of the device from the surgical site. In one embodiment, the cavity 174 is then used as the site for insertion of a fusion cage 60.

The integrated fusion cage 60 with expandable cage feature provides a number of unique and innovative features not provided by conventional or traditional integrated fusion cages. For example, the integrated fusion cage 60 with expandable cage feature of the present disclosure is intentionally and deliberately designed to receive bone graft material (or any material suitable for use in surgical applications, as known to those skilled in the art) at its proximal end (i.e. the end generally facing the surgeon and/or the end opposite the end initially directed into a surgical site), such that the bone graft material flows into the fusion cage and also flows out from the fusion cage into the surgical site. Such features as the interior ramps 9 of the fusion cage 60 (e.g. located within the interior of the hollow tube, and/or on the front and/or rear blocks of the fusion cage) function to direct received bone graft material into the surgical site. Additionally, the features of the hollow tube 2 and plunger 12 that enable a greater volume of bone graft material to be reliably (e.g. not prone to blockage as is typical with most convention e.g. round hollow tubes or lumen systems) and readily delivered to a surgical site and/or a fusion cage are unique and not found in the prior art. Among other things, such features encourage improved surgical results by delivering more volume and coverage of bone graft material to the surgical site. Also, such features minimize gaps in bone graft coverage to include gaps between the fusion cage area and the surrounding surgical site. Also, the features of the one or more apertures of the fusion cage of the disclosure enable and encourage delivery of bone graft material, as received by the fusion cage, into the surrounding surgical site.

In one embodiment of the fusion cage 60, no anti-torque structures or components are employed. In one embodiment of the invention, the lateral sides of the fusion cage 60 are substantially open to, among other things, allow egress of bone graft material as received to the fusion cage. In one embodiment, the fusion cage has an expansion screw configured with a locking mechanism, such that the fusion cage 60 may be locked at a set expansion state. In one embodiment, such a locking mechanism is provided through a toggle device operated at or on an installer/impactor handle.

In addition, it is contemplated that some embodiments of the fusion cage 60 can be configured to include side portions that project therefrom and facilitate the alignment, interconnection, and stability of the components of the fusion cage 60.

Furthermore, complementary structures can also include motion-limiting portions that prevent expansion of the fusion cage 60 beyond a certain height. This feature can also tend to ensure that the fusion cage is stable and does not disassemble during use.

In various embodiments, the aforementioned expansion screw can facilitate expansion of the fusion cage 60 through rotation, longitudinal contract of a pin, or other mechanisms. The expansion screw can also facilitate expansion through longitudinal contraction of an actuator shaft as proximal and distal collars disposed on inner and outer sleeves move closer to each other to in turn move the proximal and distal wedged block members closer together. It is contemplated that in other embodiments, at least a portion of the actuator shaft can be axially fixed relative to one of the proximal and distal wedge block members with the actuator shaft being operative to move the other one of the proximal and distal wedge members via rotational movement or longitudinal contraction of the pin.

Further, in embodiments wherein the engagement screw is threaded, it is contemplated that the actuator shaft can be configured to bring the proximal and distal wedged block members closer together at different rates. In such embodiments, the fusion cage 60 could be expanded to a V-configuration or wedged shape. For example, the actuator shaft can comprise a variable pitch thread that causes longitudinal advancement of the distal and proximal wedged block members at different rates. The advancement of one of the wedge members at a faster rate than the other could cause one end of the implant to expand more rapidly and therefore have a different height that the other end. Such a configuration can be advantageous depending on the intervertebral geometry and circumstantial needs.

In other embodiments, an upper plate of the fusion cage can be configured to include anti-torque structures. The anti-torque structures can interact with at least a portion of a deployment tool during deployment of the fusion cage implant to ensure that the implant maintains its desired orientation. For example, when the implant is being deployed and a rotational force is exerted on the actuator shaft, the anti-torque structures can be engaged by a non-rotating structure of the deployment tool to maintain the rotational orientation of the implant while the actuator shaft is rotated. The anti-torque structures can comprise one or more inwardly extending holes or indentations on the rear wedged block member. However, the anti-torque structures can also comprise one or more outwardly extending structures.

According to yet other embodiments, the fusion cage 60 is configured to include one or more additional apertures to facilitate osseointegration of the fusion cage 60 within the intervertebral space. In various embodiments, the fusion cage 60 contains one or more bioactive substances, including, but not limited to, antibiotics, chemotherapeutic substances, angiogenic growth factors, substances for accelerating the healing of the wound, growth hormones, antithrombogenic agents, bone growth accelerators or agents, and the like. Indeed, various biologics can be used with the fusion cage 60 and can be inserted into the disc space or inserted along with the fusion cage 60 The apertures can facilitate circulation and bone growth throughout the intervertebral space and through the implant. In such implementations, the apertures can thereby allow bone growth through the implant and integration of the implant with the surrounding materials.

In one embodiment, the fusion cage 60 comprises an expandable cage configured to move a first surface vertically from a second surface by rotation of at least one screw that rotates without moving transversely with respect to either said first or second surface, said first plate and second plate having perimeters that overlap with each other in a vertical direction and that move along a parallel line upon rotation of the screw.

Surprisingly, while conventional practice assumed that the amount of material that would be required, let alone desired, to fill a prepared disc space with bone paste (or BMP, etc.) would be roughly equivalent to the amount of material removed from such space prior to inserting a cage, a present inventor discovered that far more bone graft material can be—and should preferably be—inserted into such space to achieve desired fusion results. The reasons why this basic under appreciation for the volume of bone graft necessary to achieve optimal fusion results vary, but the clinical evidence arrived at via practice of the present invention compellingly demonstrates that more than doubling of the amount of bone graft material (and in some cases increasing the amount by 200%, 300% or 400% or more) than traditionally thought necessary or sufficient, is extremely beneficial to achieving desired results from fusion procedures.

The ramifications of this simple yet dramatic discovery (documented in part below) is part of the overall inventive aspect of the present invention, as it has been—to date—simply missed entirely by the practicing spine surgeons in the field. The prospect of reduced return surgeries, the reduction in costs, time, and physical suffering by patients, as well as the volume of legal complaints against surgeons and hospitals due to failed fusion results, is believed to be significant, as the evidence provided via use of the present invention indicates a vast reduction in the overall costs involved in both economic resources, as well as emotional capital, upon acceptance and wide-spread use of the present invention. Insurance costs should thus decrease as the present invention is adopted by the industry. While the costs of infusing increased amount of bone graft materials into the space of a patient's disc may at first appear to increase the costs of an individual operation, the benefits achieved thereby will be considerable, including the reduction of repeat surgeries to fix non-fused spines. Thus, regardless of the actual tools and devices employed to achieve the end result of attaining up to 100% more bone graft material being utilized in fusion operations, (as well as other surgeries where previously under-appreciated bone graft material delivery volumes have occurred) one important aspect of the present invention is directed to the appreciation of a previously unrecognized problem and the solution thereto, which forms part of the inventive aspects of the present invention described and claimed herein.

In one embodiment, at least twice the amount of disc material removed from a surgical site is replaced with bone graft material. In a preferred embodiment, at least three times the amount of disc material removed from a surgical site is replaced with bone graft material. In a most preferred embodiment, at least three and a half times the amount of disc material removed from a surgical site is replaced with bone graft material.

According to various embodiments of the present disclosure, and as illustrated at least by FIGS. 1-27, one aspect of the invention is to provide a graft delivery device that comprises a tubular member, which is substantially hollow or contains at least one inner lumen and that has a generally rectangular cross-sectional shape. This generally rectangular cross-sectional shape offers a larger amount of surface area through which bone graft material may be inserted and ejected from the hollow tubular member. Furthermore, this generally rectangular shape is more congruent with the size or shape of the annulotomy of most disc spaces, which frequently are accessed by a bone graft delivery device for delivery of bone graft. However, as one skilled in the art would appreciate, the tool cross-section need not be limited to a generally rectangular shape. For example, cross-sections of an oval shape or those with at least one defined angle to include obtuse, acute, and right angles can provide a shape in some situations that is more congruent with the size or shape of the annulotomy of a particular disc space. A substantially round shape may also be employed that provides the surgeon with an indication of directional orientation.

In embodiments, a distal end of the hollow tubular member may be at least partially closed, and/or may have a small aperture associated with the lumen. This partial closure and/or small aperture may help to create a consistent and clean break between bone graft material that has been ejected from the hollow tubular member and bone graft material held within the hollow tubular member.

In another embodiment of the present disclosure the distal end of the plunger is flexible to allow, for example, the user to maneuver the distal end and thereby any bone graft material in the hollow tube to the implantation site. One skilled in the art will appreciate that the flexible aspect of certain embodiments can be both passive and active in nature. Active flexibility and manipulation in the distal end of the plunger may incorporate, for example, the manipulative capabilities of an endoscope, including components for manipulation such as guidewires along the longitudinal axis of the shaft of the plunger.

Another embodiment for the bone graft insertion device comprises a hollow tube constructed to receive bone graft, where the hollow tube has a proximal and distal end, a plunger adapted for insertion at least partially within the hollow tube at the proximal end of the hollow tube, whereby the plunger is constructed and arranged with respect to the hollow tube so as to prevent rotation of the plunger during insertion into said hollow tube, whereby the plunger has a distal end that is contoured to an interior surface of the distal end of the hollow tube for removing substantially all of the bone graft received by the hollow tube and whereby the bone graft is delivered to the graft receiving area. Still another embodiment provides a rifling structure in the hollow tube interior that facilitates rotational movement of the plunger along a lengthwise axis of the hollow tube, therein delivering a substantially steady pressure and/or rate of delivery of the bone graft material as the plunger descends the hollow tube when the plunger is forced through the hollow tube. The rifling or screw-like movement may also translate to a predetermined delivery of material per full rotation, e.g. each 360 degree rotation of the plunger equates to 5 cc of bone graft material delivered to the bone graft site.

In embodiments, teeth may be formed along a longitudinal axis of the shaft of the plunger 12, which may be configured to engage with teeth of the grip 304 and/or knob 318 to facilitate advancement of the plunger 12 when the grip 304 and/or knob 318 is actuated. The engagement of the teeth of the plunger 12 with teeth of the grip 304 and/or knob 318 may thus, by way of non-limiting example, form a rack-and-pinion-type linear actuator that causes the plunger 12 to descend the hollow tube 2 and urge bone graft material through the hollow tube 2 to deliver bone graft material through an opening in a distal end of the hollow tube 2.

The indicia 29 may include one or more radiological or radiographic markers. Such radiological or radiographic markers may be made from known radiopaque materials, including platinum, gold, calcium, tantalum, and/or other heavy metals. At least one radiological or radiographic marker may be placed at or near the distal end of the hollow tube 2, to allow radiological visualization of the distal end within the targeted bone area.

In further embodiments, an actuating means may be provided for applying pressure to the plunger 12, and in particular to the shaft of the plunger 12. Upon actuation thereof, the actuating means may apply pressure against the plunger 12 to facilitate controlled movement of the plunger 12 and/or the hollow tube 2 relative to the plunger 12. The actuating means may, by way of non-limiting example, include a handle and a pivotally mounted trigger attached to a ratchet-type push bar (such as those commonly used with caulking guns) and/or a rack-and-pinion-type linear actuator.

According to a still further aspect of the present invention, the distal end of the spinal fusion implant may have a conical (bullet-shaped) shape including a pair of first tapered (angled) surfaces and a pair of second tapered (angled) surfaces. The first tapered surfaces extend between the lateral surfaces and the distal end of the implant, and function to distract the vertebrae adjacent to the target intervertebral space during insertion of the spinal fusion implant. The second tapered surfaces extend between the top and bottom surfaces and the distal end of the spinal fusion implant, and function to maximize contact with the anterior portion of the cortical ring of each adjacent vertebral body. Furthermore, the second tapered surfaces provide for a better fit with the contour of the vertebral body endplates, allowing for a more anterior positioning of the spinal fusion implant and thus advantageous utilization of the cortical rings of the vertebral bodies.

In other embodiments discussed above, the spinal fusion implant may be inserted into or through other sites including, but not limited to, a collapsed vertebra, or other appropriate sites known in the art. In such embodiments, the implant can be used to create a void in the vertebrae, which is then filled with bone cement or other appropriate material.

While various embodiment of the present disclosure have been described in detail, it is apparent that modifications and alterations of those embodiments will occur to those skilled in the art. However, it is to be expressly understood that such modifications and alterations are within the scope and spirit of the present disclosure, as set forth in the following claims.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

Moreover, though the present disclosure has included description of one or more embodiments and certain variations and modifications, other variations and modifications are within the scope of the disclosure, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

The invention claimed is:

1. A bone graft insertion apparatus comprising:
a hollow tube constructed to receive bone graft, said hollow tube having a longitudinal axis, a proximal end, a distal end, a rectangular cross-section taken perpendicular to said longitudinal axis, wherein an interior of said hollow tube is uniform from said proximal end to said distal end, a ramp formed within said hollow tube proximate to said distal end, and said ramp having a first ramp surface oriented toward a first lateral opening and a second ramp surface oriented toward a second lateral opening; and
a plunger adapted for inserting into said proximal end of said hollow tube along said extended axis, said plunger having a shaft and a distal portion with a first arm and a second arm, said first arm configured to deliver bone graft material through said first lateral opening and said second arm configured to deliver bone graft material through said second lateral opening.

2. The apparatus of claim 1, wherein said first lateral opening of said hollow tube is formed in a first side of said hollow tube and extends into upper and lower sides of said hollow tube.

3. The apparatus of claim 1, wherein said first arm of said plunger is configured to bend toward said first lateral opening after contacting said first ramp surface, and wherein said second arm of said plunger is configured to bend toward said second lateral opening after contacting said second ramp surface.

4. The apparatus of claim 1, wherein said first arm of said plunger is separated from said second arm of said plunger by a groove that extends generally parallel to a longitudinal axis of said plunger.

5. The apparatus of claim 4, wherein a plurality of notches are formed in said first and second arms of said plunger, the plurality of notches extending inwardly into said first and second arms of said plunger toward said groove.

6. The apparatus of claim 1, further comprising a first rabbet formed on said first arm of said plunger and a second rabbet formed on said second arm of said plunger, wherein said distal portion of said plunger has an exterior width that is less than an exterior width of a proximal portion of said plunger.

7. The apparatus of claim 1, wherein said plunger is operable to deliver bone graft material having a fibrous composition through the first and second lateral openings of said hollow tube.

* * * * *